US008415147B2

(12) United States Patent
Dolja et al.

(10) Patent No.: US 8,415,147 B2
(45) Date of Patent: Apr. 9, 2013

(54) CLOSTEROVIRUS VECTORS AND METHODS

(75) Inventors: Valerian V. Dolja, Corvallis, OR (US); Valera V. Peremyslov, Corvallis, OR (US)

(73) Assignee: State of Oregon Acting By and Through the State Board of Higher Education on Behalf of Oregon State University, Corvallis, OR (US)

( * ) Notice: Subject to any disclaimer, the term of this patent is extended or adjusted under 35 U.S.C. 154(b) by 0 days.

(21) Appl. No.: 12/865,708

(22) PCT Filed: Jan. 29, 2009

(86) PCT No.: PCT/US2009/032380

§ 371 (c)(1),
(2), (4) Date: Jul. 30, 2010

(87) PCT Pub. No.: WO2009/099877

PCT Pub. Date: Aug. 13, 2009

(65) Prior Publication Data

US 2010/0333230 A1 Dec. 30, 2010

Related U.S. Application Data

(60) Provisional application No. 61/063,305, filed on Jan. 31, 2008, provisional application No. 61/083,504, filed on Jul. 24, 2008.

(51) Int. Cl.
*C12N 15/83* (2006.01)
*C12N 5/14* (2006.01)
*C12N 15/33* (2006.01)

(52) U.S. Cl.
USPC ......... 435/320.1; 435/419; 800/280; 800/294

(58) Field of Classification Search ................... 800/280
See application file for complete search history.

(56) References Cited

U.S. PATENT DOCUMENTS

2002/0104126 A1 8/2002 Pogue et al.
2005/0091706 A1 4/2005 Klimyuk et al.
2005/0183165 A1* 8/2005 Zhu et al. ...................... 800/286
2006/0228800 A1 10/2006 Lin et al.

FOREIGN PATENT DOCUMENTS

WO WO 98/52964 11/1998

OTHER PUBLICATIONS

Peremyslov et al. Genes required for replication of the 15.5-kilobase RNA genome of a plant closterovirus (1998) J. of Virol. 72: 5870-5876.*

Chiba et al. Diverse suppressors of RNA silencing enhance agroifection by a viral replicon (2006) Virology 346: 7-14.*

Berglund et al. Semliki forest virus expression system: production of conitionally infectious recombinant particles (1993) Nat. Biotechnol. 11: 916-920.*

Peremyslov et al. Hsp70 homolog functions in cell-to-cell movement of a plant virus (1999) PNAS 96: 14771-14776.*

UniProtKB/TrEMBL submission Q491G4 (Online) Sep. 2005 (retrieved on May 28, 2009); www.uniprot.org/uniprot/Q49IG4, 3 pages.

Sabanadzovic et al., "Complete nucleotide sequence and genome organization of Grapevine fleck virus," *J. General Virology*, 82:2009-2015, 2001.

Leiser et al., "Agroinfection as an alternative to insects for infecting plants with beet western yellows luteovirus," *Proc. Natl. Acad. Sci. USA*, 89: 9136-9140, 1992.

Li et al., "Stable expression of foreign proteins in herbaceous and apple plants using Apple latent spherical virus RNA2 vectors," *Arch. Virol.*, 149: 1541-1558, 2004.

Lindner, "Deubiquitination in virus infection," *Virology*, 362: 245-256, 2007.

Liu et al., "Tandem leader proteases of Grapevine leafroll-associated virus-2: host-specific functions in the infection cycle," *Virology*, 383: 291-299, 2009.

Lu et al., "Three distinct suppressors of RNA silencing encoded by a 20-kb viral RNA genome," *Proc. Natl. Acad. Sci. USA*, 101: 15742-15747, 2004.

Marillonnet et al., "Systemic *Agrobacterium tumefaciens*-mediated transfection of viral replicons for efficient transient expression in plants," *Nat. Biotechnol.*, 23: 718-723, 2005.

Martin et al., "Expression of an *Arabidopsis* sucrose synthase gene indicates a role in metabolization of sucrose both during phloem loading and in sink organs," *Plant J.*, 4: 367-377, 1993.

Medina et al., "Subcellular localization of the HSP70-homolog encoded by beet yellows closterovirus ," *Virology*, 260(1): 173-181, 1999.

Meng et al., "Genome sequences and structures of two biologically distinct strains of Grapevine leafroll-associated virus 2 and sequence analysis," *Virus Genes*, 31: 31-41, 2005.

Napuli et al., "Interaction between HSP70 homolog and filamentous virions of the Beet yellows virus," *Virology*, 274(1): 232-239, 2000.

Napuli et al., "The 64-kilodalton capsid protein homolog of Beet yellows virus is required for assembly of virion tails," *J. Virol.*, 77: 2377-2384, 2003.

Ng & Falk, "Virus-vector interactions mediating nonpersistent and semipersistent transmission of plant viruses," *Ann. Rev. Phytopathol.*, 44: 183-212, 2006.

Peng & Dolja, "Leader proteinase of the beet yellows closterovirus: mutation analysis of the function in genome amplification," *J. Virol.*, 74: 9766-9770, 2000.

Peng et al., "A replication-competent chimera of plant and animal viruses," *Virology*, 294: 75-84, 2002.

Peng et al., "Functional specialization and evolution of leader proteinases in the family Closteroviridae," *J. Virol.*, 75(24): 12153-12160, 2001.

Peng et al., "Leader proteinase of beet yellows virus functions in long-distance transport," *J. Virol.*, 77: 2843-2849, 2003.

Peremyslov and Dolja, *Curr. Protocols Microbiol.*, "Cloning of Large Positive-Strand RNA Viruses" Suppl. 7., Coico, ed., Nov. 2007.

Peremyslov et al., "Complex molecular architecture of beet yellows virus particles," *Proc. Natl. Acad. Sci. USA*,, 101: 5030-5035, 2004.

Peremyslov et al., "Genes required for replication of the 15.5-kilobase RNA genome of a plant closterovirus," *J. Virol.*, 72: 5870-5876, 1998.

(Continued)

*Primary Examiner* — David H Kruse
*Assistant Examiner* — Steven Bernacki
(74) *Attorney, Agent, or Firm* — Klarquist Sparkman, LLP

(57) ABSTRACT

The present disclosure relates to the development and use of Closterovirus-based vectors for the delivery of nucleotides to plants. Specifically, the present disclosure provides viral vectors based on Grapevine leafroll-associated virus-2 for the delivery and expression of genes in plants, particularly grape plants. Methods of making and using these vectors, as well as the plants transformed by these vectors, are also contemplated.

17 Claims, 22 Drawing Sheets

OTHER PUBLICATIONS

Peremyslov et al., "HSP70 homolog functions in cell-to-cell movement of a plant virus," *Proc. Natl. Acad. Sci. USA*, 96: 14771-14776, 1999.

Peretz et al., "A universal expression/silencing vector in plants," *Plant Physiol.*, 145(4): 1251-1263, 2007.

Pogue et al., "Making an ally from an enemy: plant virology and the new agriculture," *Ann. Rev. Phytopathol.*, 40: 45-74, 2002.

Prokhnevsky et al., "Interaction between long-distance transport factor and Hsp70-related movement protein of Beet yellow virus," *J. Virol.*, 76: 11003-11011, 2002.

Reed et al., "Suppressor of RNA silencing encoded by Beet yellows virus," *Virology*, 306: 203-209, 2003.

Satyanarayana et al., "Closterovirus bipolar virion: evidence for initiation of assembly by minor coat protein and its restriction to the genomic RNA 5' region," *Proc. Natl. Acad. Sci. USA.*, 101: 799-804, 2004.

Satyanarayana et al., "Closterovirus encoded HSP70 homolog and p61 in addition to both coat proteins function in efficient virion assembly," *Virology*, 278(1): 253-265, 2000.

Segers et al., "Hypovirus papain-like protease p29 suppresses RNA silencing in the natural fungal host and in a heterologous plant system," *Eukaryot. Cell*, 5: 896-904, 2006.

Susaimuthu et al., "A member of a new genus in the Potyviridae infects Rubus," *Virus Res.*, 131: 145-151, 2008.

Tian et al., "Lettuce infectious yellows virus: in vitro acquisition analysis using partially purified virions and the whitefly *Bemisia tabaci*," *J. Gen. Virol.*, 80: 1111-1117, 1999.

Tijms et al., "Arterivirus subgenomic mRNA synthesis and virion biogenesis depend on the multifunctional nsp 1 autoprotease," *J. Virol.*, 81: 10496-10505, 2007.

Torrance et al., "An unusual structure at one end of potato potyvirus particles," *J. Mol. Biol.*, 357: 1-8, 2005.

Truernit and Sauer, "The promoter of the *Arabidopsis thaliana* SUC2 sucrose-H+ symporter gene directs expression of beta-glucuronidase to the phloem: evidence for phloem loading and unloading by SUC2," *Planta*, 196: 564-570, 1995.

Tzanetakis & Martin, "Strawberry chlorotic fleck: identification and characterization of a novel Closterovirus associated with the disease," *Virus Res.*, 124: 88-94, 2007.

Tzanetakis et al., "Identification and characterization of Raspberry mottle virus, a novel member of the Closteroviridae," *Virus Res.*, 127: 26-33, 2007.

Valli et al., "RNA silencing suppression by a second copy of the P1 serine protease of Cucumber vein yellowing ipomovirus, a member of the family Potyviridae that lacks the cysteine protease HCPro," *J. Virol.*, 80: 10055-10063, 2006.

Zhu et al., "Nucleotide sequence and genome organization of grapevine leafroll-associated virus-2 are similar to beet yellows virus, the closterovirus type member," *J. Gen. Virol.*, 79: 1289-1298, 1998.

Ziebuhr et al., "Human coronavirus 229E papain-like proteases have overlapping specificities but distinct functions in viral replication," *J. Virol.*, 81: 3922-3932, 2007.

Ziebuhr et al., "Virus-encoded proteinases and proteolytic processing in the Nidovirales," *J. Gen. Virol.*, 81: 853-879, 2000.

University of California Pest Management Guidelines, Statewide Integrated Pest Management Systems, available on the World Wide Web at.ipm.ucdavis.edu/PMG/r302101211.html (3 pages; last accessed Jan. 27, 2008).

Agranovsky et al., "'Rattlesnake' structure of a filamentous plant RNA virus built of two capsid proteins," *Proc. Natl. Acad. Sci. USA*, 92(7): 2470-2473, 1995.

Agranovsky et al., "Nucleotide sequence of the 3'-terminal half of beet yellows closterovirus RNA genome: unique arrangement of eight virus genes," *J. Gen. Virol.*, 72: 15-23, 1991.

Alzhanova et al., "Genetic analysis of the cell-to-cell movement of beet yellows closterovirus," *Virology*, 268(1): 192-200, 2000.

Alzhanova et al., "Virion tails of Beet yellows virus: Coordinated assembly by three structural proteins," *Virology*, 359: 220-226, 2007.

Alzhanova, "Cell-to-cell movement and assembly of a plant closterovirus: roles for the capsid proteins and Hsp70 homolog," *EMBO J.*, 20: 6997-7007, 2001.

Barker et al., "Genetic and physical mapping of the grapevine powdery mildew resistance gene, Run1, using a bacterial artificial chromosome library," *Theor. Appl. Genet.*, 111: 370-377, 2005.

Barrett & Rawlings, "Evolutionary lines of cysteine peptidases," *Biol. Chem.*, 382: 727-733, 2001.

Bieniawska et al., "Analysis of the sucrose synthase gene family in *Arabidopsis*," *The Plant Journal*, 49: 810-828, 2007.

Bouquet et al., "Grapevine (*Vitis vinifera* L.)," *Methods Mol. Biol.*, 344: 273-285, 2006.

Boyko et al., "Coat protein gene duplication in a filamentous RNA virus of plants," *Proc. Natl. Acad. Sci. USA*, 89: 9156-9160, 1992.

Chapman et al., "Potato virus X as a vector for gene expression in plants," *Plant J.*, 2: 549-557, 1992.

Chiba et al., "Diverse suppressors of RNA silencing enhance agroinfection by a viral replicon," *Virology*, 346: 7-14, 2006.

de los Santos et al., "The leader proteinase of foot-and-mouth disease virus inhibits the induction of beta interferon mRNA and blocks the host innate immune response," *J. Virol.*, 80: 1906-1914, 2006.

DeWitt et al., "Evidence for a plasma membrane proton pump in phloem cells of higher plants," *Plant J.*, 1: 121-128, 1991.

Ding & Voinnet, "Antiviral immunity directed by small RNAs," *Cell*, 130: 413-426, 2007.

Dolja et al., "Comparative and functional genomics of closteroviruses," *Virus Res.*, 117: 38-51, 2006.

Dolja et al., "Isolation and stability of histidine-tagged proteins produced in plants via potyvirus gene vectors," *Virology*, 252: 269-274, 1998.

Dolja et al., "Tagging of plant potyvirus replication and movement by insertion of β- glucuronidase into the viral polyprotein," *Proc. Natl. Acad. Sci., USA*, 89: 10208-10212, 1992.

Donson et al., "Systemic expression of a bacterial gene by a tobacco mosaic virus-based vector," *Proc. Natl. Acad. Sci. USA*, 88: 7204-7208, 1991.

Dougherty & Semler, "Expression of virus-encoded proteinases: functional and structural similarities with cellular enzymes," *Microbiol. Rev.*, 57(4): 781-822, 1993.

Folimonov et al., "A stable RNA virus-based vector for citrus trees," *Virology*, 368(1): 205-216, 2007.

Gabrenaite-Verkhovskaya et al., "Cylindrical inclusion protein of potato virus A is associated with a subpopulation of particles isolated from infected plants," *J. Gen. Virol.*, 89: 829-838, 2008.

Gleba et al., "Viral vectors for the expression of proteins in plants," *Curr. Opin. Biotechnol.*, 18: 134-141, 2007.

Godge et al., "Virus-induced gene silencing for functional analysis of selected genes," *Plant Cell. Rep.*, 27(2): 209-219, 2008; e-pub ahead of print, 2007.

Gorbalenya et al., "Cysteine proteases of positive strand RNA viruses and chymotrypsin-like serine proteases. A distinct protein superfamily with a common structural fold," *FEBS Lett.*, 243: 103-114, 1989.

Gorbalenya et al., "Nidovirales: evolving the largest RNA virus genome," *Virus Res.*, 117(1): 17-37, 2006.

Gorbalenya et al., "Putative papain-related thiol proteases of positive-strand RNA viruses. Identification of rubi- and aphthovirus proteases and delineation of a novel conserved domain associated with proteases of rubi-, α- and coronaviruses," *FEBS Lett,*. 288(1-2): 201-205, 1991.

Goszczynski et al., "Detection of two strains of grapevine leafroll-associated virus 2," *Vitis*, 35: 133-135, 1996.

Hagiwara et al., "Regulation of Closterovirus Gene Expression Examined by Insertion of a Self-Processing Reporter and by Northern Hybridization," *J. Virol.*, 73: 7988-7993, 1999.

Haviv et al., "Engineering the genome of Grapevine virus A into a vector for expression of proteins in herbaceous plants," *J. Virol. Meth.*, 132: 227-231, 2006.

HongYu et al., "Isolation and characterization of 4 gametophytic male sterile mutants in *Arabidopsis thaliana," Chinese Science Bulletin*, 52: 1949-1956, 2007.

Imlau et al., "Cell-to-Cell and Long-Distance Trafficking of the Green Fluorescent Protein in the Phloem and Symplastic Unloading of the Protein into Sink Tissues," *Plant Cell*, 11: 309-322, 1999.

Karasev et al., "Complete sequence of the citrus tristeza virus RNA genome," *Virology*, 208: 511-520, 1995.

Karasev, "Genetic Diversity and Evolution of Closteroviruses," *Ann. Rev. Phytopathol.*, 38: 293-324, 2000.

Kasschau et al., "Genome amplification and long-distance movement functions associated with the central domain of tobacco etch potyvirus helper component-proteinase," *Virology*, 228(2): 251-262, 1997.
Koonin & Dolja, "Evolution and taxonomy of positive-strand RNA viruses: implications of comparative analysis of amino acid sequences," *Crit. Rev. Biochem. Mol. Biol.*, 28(5): 375-430, 1993.
Koonin & Dolja, "Evolution of complexity in the viral world: the dawn of a new vision," *Virus Res.*, 117: 1-4, 2006.
Lakatos et al., "Small RNA binding is a common strategy to suppress RNA silencing by several viral suppressors," *EMBO J.*, 25: 2768-2780, 2006.

* cited by examiner

LEAVES STEMS PETIOLES

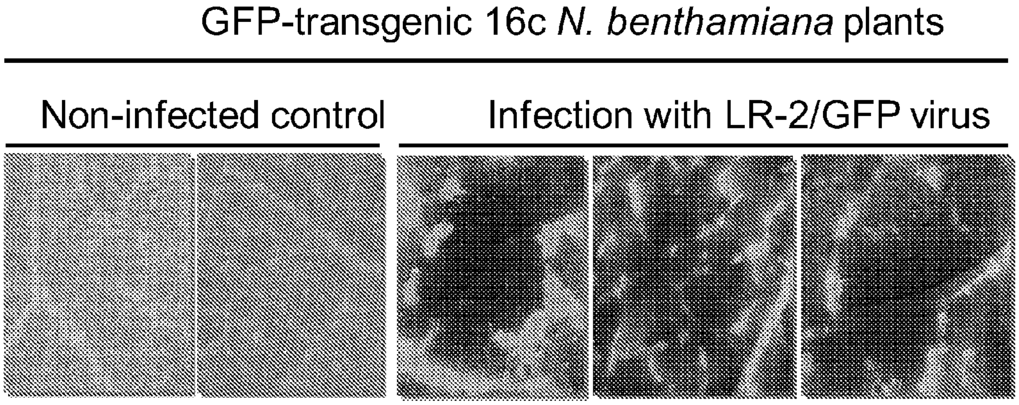
FIG. 6
FIG. 7A
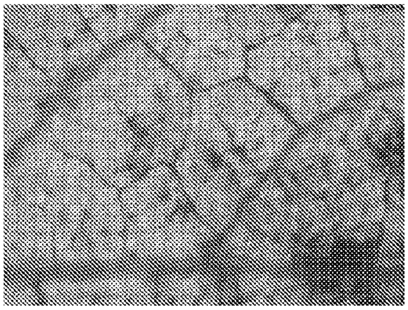
FIG. 7B
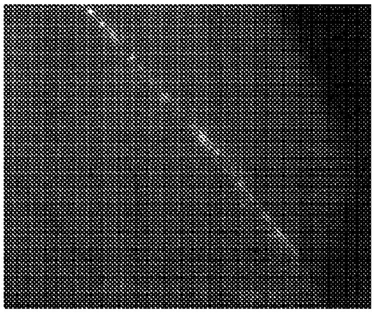
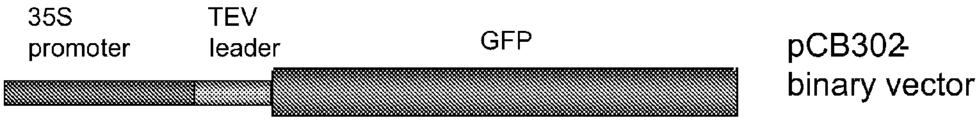
FIG. 7C

```
NB    ATATTCTGTTGGCTTTCATCTGTGCTTGTGCTTCGGTTCAATCACACTCTGAAAGTTTCA
VV    ATATTCTGTTGGCTTTCATCTGTGCTTGTGCTTCGGTTCAATCACACTCTGAAAGTTTCA

NB    GTTCCCCGGAATTTCGGTTTTCTTCATAAGCCTTATTCCTACAGGATGTCTAGCCTTGCT
VV    GTTCCCCGGAATTTCGGTTTTCTTCATAAGCCTTATTCTTACAGGATGTCTAGCCTTGCT

NB    ATCTCTGCCCTTCCCTGTTCAGTCGCTCAACTGAGCGTTGGTCAGCCTGTTGCCACGGTT
VV    ATCTCTGCCCTTCCCTGTTCAGTCGCTCAACTGAGCGTTGGTCAGCCTGTTGCCACGGTT

NB    GCCAGGTCATTTTTGATGACTTCCCTTCCGTCCCTTCAGACTTACCCATCTTCGTCTGAG
VV    GCCAGGTCATTTTTGATGACTTCCCTTCCGTCCCTTCAGACTTACCCATCTTCGTCTGAG

NB    TTGACTTCCTTTTTATTTTGTTTTGGTGCTTTCCAAAAAATAAAAATGTTTTTATCTTTC
VV    TTGACTTCCTTTTTATTTTGTTTTGGTGCTTTCCAAAAAATAAAAATGTTTTTATCTTTC

NB    CTACGTTCGGTGCACGTCTTTGCGCCTTTTTCTGAAATTTCCACGATTGGTTCATGCTAT
VV    CTACGTTCGGTGCACGTCTTTGCGCCTTTTTCTGAAATTTCCACGATTGGTTCATGCTAT

NB    GAATTCATTCGGTTGGGAGGTGGTGCTTACCCTCTCTTTTTCTGTTCCTTCCAATGCGGA
VV    GAATTCATTCGGTTGGGAGGTGGTGCTTACCCTCTCTTTTTCTGTTCCTTCCAATGCGGA

NB    CCTTTGTCCGTTTCTTTGGGTTTTGTTAACGGCGTTTTTGCTGTTTTAAACATGTCATTT
VV    CCTTTGTCCGTTTCTTTGGGTTTTGTTAACGGCGTTTTTGCTGTTTTAAACATGTCATTT

NB    CCTTTCTTAAGCAACGCATCTCTTTTGACGGGCGTCGGAAAAAATGTTGTTCAAGAGAAA
VV    CCTTTCTTAAGCAACGCATCTCTTTTGACGGGCGTCGGAAAAAATGTTGTTCAAGAGAAA

NB    ATAAAAATTTCCAAATTTGAGAAGAAACAGAAGAAGCGCGTTTTTTCGATAGCTCGCGCT
VV    ATAAAAATTTCCAAATTTGAGAAGAAACAGAAGAAGCGCGTTTTTTCGATAGCTCGCGCT

NB    ACCGCGCGTCATGTGCCTTCCCGTCGCAATCCTAAGGAGAAGCGTGTTGTCCATGTACAG
VV    ACCGCGCGTCATGTGCCTTCCCGTCGCAATCCTAAGGAGAAGCGTGTTGTCCATGTACAG

NB    CATCTCCCTAGTGGTTCTTTACGCTTTTCCCAAAACAAAAACAAAACAGAACTGCTCATC
VV    CATCTCCCTAGTGGTTCTTTACGCTTTTCCCAAAACAAAAACAAAACAGAACTGCTCATC

NB    TTAAAAGAGGAAGTCGGAATTGTCGCGCGCGTTAAGTGTTCGGCAAGCGTCGTGCGCCGT
VV    TTAAAAGAGGAAGTCGGAATTGTCGCGCGCGTTAAGTGTTCGGCAAGCGTCGTGCGCCGT

NB    CGCGTTTGTGGCGGTGTGGTTAAGTGCAAACCCCTAATAGCCGTTTCTCCCTCTGGCGTG
VV    CGCGTTTGTGGCGGTGTGGTTAAGTGCAAACCCCTAATAGCCGTTTCTCCCTCTGGCGTG

NB    AAATTCCGTTGTTTCGCGCCGTCTTGCAGCACGTCCGCTTGTTTAAAGCTCAAAATCATG
VV    AAATTCCGTTGTTTCGCGCCGTCTTGCAGCACGTCCGCTTGTTTAAAGCTCAAAATCATG

NB    CGCCGTGTTGCCGTCGGTGACTGCCGAGGTGAGAAGATAATCGCGGCACGACGTGCGGCG
VV    CGCCGTGTTGCCGTCGGTGACTGCCGAGGTGAGAAGATAATCGCGGCACGACGTGCGGCG

NB    CTGCAGAAGCAGGCTTTCAACAGCCGCACACCGAAGAAAGTGCGAGAGAACCCCATTAGC
VV    CTGCAGAAGCAGGCTTTCAACAGCCGCACACCGAAGAAAGTGCGAGAGAACCCCATTAGC

NB    GTCTCCGGGGTGAACTTGGGAAGGTCTGCCGCCGCTCAGGTTATTTATTTCGGCAGTTTC
VV    GTCTCCGGGGTGAACTTGGGAAGGTCTGCCACCGCTCAGGTTATTTATTTCGGCAGTTTC

NB    ACGCAGCCCTTCGCGTTGTATCCGCGCCAAGAGAGCGCGATCGTAAAAACGCAACCTCCA
VV    ACGCAGCCCTTCGCGTTGTATCCGCGCCAAGAGAGCGCGATCGTAAAAACGCAACCTCCA

NB    CCGGTCAGTGTAGTGAAGGTGGAGTGCGTAGCTGCGGAGGTAGCTCCCGACAGGGGCGTG
VV    CCGGTCAGTGTAGTGAAGGTGGAGTGCGTAGCTGCGGAGGTAGCTCCCAACAGGGGCGTG
```

FIG. 14A

```
NB    GTCGACAAGAAACCTACGTCTGTTGGCGTTCCCCCGCAGCGCGGTGTGCTTTCTTTTCCG
VV    GTCGACAAGAAACCTACGTCTGTTGGCGTTCCCCCGCAGCGCGGTGTGCTTTCTTTTCCG

NB    ACGGTGGTTCGGAACCGCGGCGACGTGATAATCACAGGGGTGGTGCATGAAGCCCTGAAG
VV    ACGGTGGTTCGGAACCGCGGCGACGTGATAATCGCAGGGGTGGTGCATGAAGCCTTGAAG

NB    AAAATTAAAGACGGGCTCTTACGCTTCCGCGTAGGCGGTGACATGCGTTTTTCGAGATTT
VV    AAAATTAAAGACGGGCTCTTACGCTTCCGCGTAGGCGGTGACATGCGTTTTTCGAGATTT

NB    TTCTCATCGAACTACGGCTGCAGATTCGTCGCGAGCGTGCGTACGAACACTACAGTTTGG
VV    TTCTCATCGAACTACGGCTGCAGATTCGTCGCGAGCGTGCGTACGAACACTACAGTTTGG

NB    CTAAATTGCACGAAAGCGAGTGGTGAGAAATTCTCACTCGCCGCCGCGTGCACGGCGGAT
VV    CTAAATTGCACGAAAGCGAGTGGTGAGAAATTCTCACTCGCCGCCGCGTGCACGGCGGAT

NB    TACGTGGCGATGCTGCGTTATGTGTGTGGCGGGAAATTTCCTCTCGTCCTCATGAGTAGA
VV    TACGTGGCGATGCTGCGTTATGTATGTGGCGGGAAATTTCCTCTCGTCCTCATGAGTAGA

NB    GTTATTTACCCGGATGGGCGCTGTTACTTGGCCCATATGAGGTATTTGTGCGCCTTTTAC
VV    GTTATTTACCCGGAAGGGCGCTGTTACTTGGCCCATATGAGGTATTTGTGCGCCTTTTAC

NB    TGTCGCCCGTTTAGAGAGTCGGATTATGCCCTCGGAATGTGGCCTACGGTGGCGCGTCTC
VV    TGTCGCCCGTTTAGAGAGTCGGATTATGCCCTCGGAATGTGGCCTACGGTGGCGCGTCTC

NB    AGGGCATGCGTTGAGAAGAACTTCGGTGTCGAAGCTTGTGGCATAGCTCTTCGTGGCTAT
VV    AGGGCATGCGTTGAGAAGAACTTCGGTGTCGAAGCTTGTGGCATAGCTCTTCGTGGCTAT

NB    TACACCTCTCGCAATGTTTATCACTGTGATTATGACTCTGCTTATGTAAAATATTTTAGA
VV    TACACCTCTCGCAATGTTTATCACTGTGATTATGACTCTGCTTATGTAAAATATTTTAGA

NB    AACCTTTCCGGCCGCATTGGCGGTGGTTCGTTCGATCCGACATCTTTAACCTCCGTAATA
VV    AACCTTTCCGGCCGCATTGGCGGTGGTTCGTTCGATCCGACATCTTTAACCTCCGTAATA

NB    ACGGTGAAGATTAGCGGTCTTCCAGGTGGTCTTCCTAAAAATATAGCGTTTGGTGCCTTC
VV    ACGGTGAAGATTAGCGGTCTTCCAGGTGGTCTTCCTAAAAATATAGCGTTTGGTGCCTTC

NB    CTGTGCGATATACGTTACGTCGAACCGGTAGACTCGGGCGGCATTCAATCGAGCGTTAAG
VV    CTGTGCGATATACGTTACGTCGAACCGGTAGACTCGGGCGGCATTCAATCGAGCGTTAAG

NB    ACGAAACGTGAAGATGCGCACCGAACCGTAGAGGAACGGGCGGCCGGCGGATCCGTCGAG
VV    ACGAAACGTGAAGATGCGCACCGAACCGTAGAGGAACGGGCGGCCGGCGGATCCGTCGAG

NB    CAACCGCGACAAAAGAGGATAGATGAGAAAGGTTGCGGCAGAGTTCCTAGTGGAGGTTTT
VV    CAACCGCGACAAAAGAGGATAGATGAGAAAGGTTGCGGCAGAGTTCCTAGTGGAGGTTTT

NB    TCGCATCTCCTGGTCGGCAGCCTTAACGAAGTTAGGAGGAAGGTAGCTGCCGGACTTCTA
VV    CCGCATCTCCTGGTCGGCAGCCTTAACGAAGTTAGGAGGAAGGTAGCTGCCGGACTTCTA

NB    CGCTTTCGCGTTGGCGGTGATATGGATTTTCATCGCTCGTTCTCCACCCAAGCGGGCCAC
VV    CGCTTTCGCGTTGGCGGTGATATGGATTTTCATCGCTCGTTCTCCACCCAAGCGGGCCAC

NB    CGCTTGCTGGTGTGGCGCCGCTCGAGCCGGAGCGTGTGCCTTGAACTTTACTCACCATCT
VV    CGCTTGCTGGTGTGGCGCCGCTCGAGCCGGAGCGTGTGCCTTGAACTTTACTCACCATCT

NB    AAAAACTTTTTGCGTTACGATGTCTTGCCTTGTTCTGGAGACTATGCAGCGATGTTTTCT
VV    AAAAACTTTTTGCGTTGCGATGTCTTGCCTTGTTCTGGAGACTATGCAGCGATGTTTTCT

NB    TTCGCGGCGGGCGGCCGTTTCCCTTTAGTTTTGATGACTAGAATTAGATACCCGAACGGG
VV    TTCGCGGCGGGCGGCCGTTTCCCTTTAGTTTTGATGACTAGAATTAGATACCCGAACGGG
```

FIG. 14B

NB TTTTGTTACTTGGCTCACTGCCGGTACGCGTGCGCGTTTCTCTTAAGGGGTTTTGATCCG
VV TTTTGTTACTTGGCTCACTGCCGGTACGCGTGCGCGTTTCTCTTAAGGGGTTTTGATCCG

NB AAGCGTTTCGACATCGGTGCTTTCCCCACCGCAGCCAAGCTCAGAAACCGTATGGTTTCG
VV AAGCGTTTCGACATCGGTGCTTTCCCCACCGCGGCCAAGCTCAGAAACCGTATGGTTTCG

NB GAGCTTGGTGAAAGAAGTTTAGGTTTGAACTTGTACGGCGCATATACGTCACGCGGCGTC
VV GAGCTTGGTGAAAGAAGTTTAGGTTTGAACTTGTACGGCGCATATACGTCACGCGGCGTC

NB TTTCACTGCGATTATGACGCTAAGTTTATAAAGGATTTGCGTCTTATGTCAGCAGTTATA
VV TTTCACTGCGATTATGACGCTAAGTTTATAAAGGATTTGCGTCTTATGTCAGCAGTTATA

NB GCTGGAAAGGACGGAGTGGAAGAGGTGGTACCTTCTGACATAACTCCTGCCATGAAGCAG
VV GCTGGAAAGGACGGGGTGGAAGAGGTGGTACCTTCTGACATAACTCCTGCCATGAAGCAG

NB AAAACGATCGAAGCCGTGTATGATAGATTATATGGCGGCACTGACTCGTTGCTGAAACTG
VV AAAACGATCGAAGCCGTGTATGATAGATTATATGGCGGCACTGACTCGTTGCTGAAACTG

NB AGCATCGAGAAAGACTTAATCGATTTCAAAAATGACGTGCAGAGTTTGAAGAAAGATCGG
VV AGCATCGAGAAAGACTTAATCGATTTCAAAAATGACGTGCAGAGTTTGAAGAAAGATCGG

NB CCGATTGTCAAAGTGCCCTTTTATATGTCGGAAGCAACACAGAATTCGCTGACGCGTTTC
VV CCGATTGTCAAAGTGCCCTTTTACATGTCGGAAGCAACACAGAATTCGCTGACGCGTTTC

NB TACCCTCAGTTCGAACTTAAGTTTTCGCACTCCTCGCATTCAGATCATCCCGCCGCCGCC
VV TACCCTCAGTTCGAACTTAAGTTTTCGCACTCCTCGCATTCAGATCATCCCGCCGCCGCC

NB GCTTCTAGACTGCTGGAAAATGAAACGTTAGTGCGCTTATGTGGTAATAGCGTTTCAGAT
VV GCTTCTAGACTGCTGGAAAATGAAACGTTAGTGCGCTTATGTGGTAATAGCGTTTCAGAT

NB ATTGGAGGTTGTCCTCTTTTCCATTTGCATTCCAAGACGCAAAGACGGGTTCACGTATGT
VV ATTGGAGGTTGTCCTCTTTTCCATTTGCATTCCAAGACGCAAAGACGGGTTCACGTATGT

NB AGGCCTGTGTTGGATGGCAAGGATGCGCAGCGTCGCGTGGTGCGTGATTTGCAGTATTCC
VV AGGCCTGTGTTGGATGGCAAGGATGCGCAGCGTCGCGTGGTGCGTGATTTGCAGTATTCC

NB AACGTGCGTTGGGGAGACGATGATAAAATTTTGGAAGGGCCACGCAATATCGACATTTGC
VV AACGTGCGTTTGGGAGACGATGATAAAATTCTGGAAGGGCCACGCAATATCGACATTTGC

NB CACTATCCTCTGGGCGCGTGTGACCACGAAAGTAGTGCTATGATGATGGTGCAGGTGTAT
VV CACTATCCTCTGGGCGCGTGTGACCACGAAAGTAGTGCTATGATGATGGTGCAGGTGTAT

NB GACGCGTCCCTTTATGAGATATGTGGCGCCATGATCAAGAAGAAAAGCCGCATAACGTAC
VV GACGCGTCCCTTTATGAGATATGTGGCGCCATGATCAAGAAGAAAAGCCGCATAACGTAC

NB TTAACCATGGTCACGCCCGGCGAGTTTCTTGACGGACGCGAATGCGTCTATATGGAGTCG
VV TTAACCATGGTCACGCCCGGCGAGTTTCTTGACGGACGCGAATGCGTCTATATGGAGTCG

NB TTAGACTGTGAGATTGAGGTTGATGTGCACGCGGACGTCGTAATGTACAAATTCGGTAGT
VV TTAGACTGTGAGATTGAGGTTGATGTGCACGCGGACGTCGTAATGTACAAATTCGGTAGT

NB TCTTGCTATTCGCACAAGCTTTCAATCATCAAGGACATCATGACCACTCCGTACTTGACA
VV TCTTGCTATTCGCACAAGCTTTCAATCATCAAGGACATCATGACCACTCCGTACTTGACA

NB CTAGGTGGTTTTCTATTCAGCGTGGAGATGTATGAGGTGCGTATGGGCGTGAATTACTTC
VV CTAGGTGGTTTTCTATTCAGCGTGGAGATGTATGAGGTGCGTATGGGCGTGAATTACTTC

NB AAGATTACGAAGTCCGAAGTATCGCCTAGCATTAGCTGCACCAAGCTCCTGAGATACCGA
VV AAGATTACGAAGTCCGAAGTATCGCCTAGCATTAGCTGCACCAAGCTCCTGAGATATCGA

FIG. 14C

```
NB    AGAGCTAATAGTGACGTGGTTAAAGTTAAACTTCCACGTTTCGATAAGAAACGTCGCATG
VV    AGAGCTAATAGCGACGTGGTTAAAGTTAAACTTCCACGTTTCGATAAGAAACGTCGCATG

NB    TGTCTGCCTGGGTATGACACCATATACCTAGATTCGAAGTTTGTGAGTCGCGTTTTCGAT
VV    TGTCTGCCTGGGTATGACACCATATACCTAGATTCGAAGTTTGTGAGTCGCGTTTTCGAT

NB    TATGTCGTGTGTAATTGCTCTGCCGTGAACTCAAAAACTTTCGAGTGGGTGTGGAGTTTC
VV    TATGTCGTGTGTAATTGCTCTGCCGTGAACTCAAAAACTTTCGAGTGGGTGTGGAGTTTC

NB    ATTAAGTCTAGTAAGTCGAGGGTGATTATTAGCGGTAAAATAATTCACAAGGATGTGAAT
VV    ATTAAGTCTAGCAAGTCGAGGGTGATTATTAGCGGTAAAATAATTCACAAGGATGTGAAT

NB    TTGGACCTTAAGTACGTCGAGAGTTTCGCCGCGGTTATGTTGGCCTCTGGCGTGCGCAGC
VV    TTGGACCTCAAGTACGTCGAGAGTTTCGCCGCGGTTATGTTGGCCTCTGGCGTGCGCAGC

NB    AGACTAGCGTCCGAGTACCTTGCTAAGAACCTTAGTCATTTTTCGGGAGATTGCTCCTTT
VV    AGACTAGCGTCCGAGTACCTTGCTAAGAACCTTAGTCATTTTTCGGGAGATTGCTCCTTT

NB    ATTGAAGCCACGTCTTTCGTGTTGCGTGAGAAAATCAGAAACATGACTCTGAATTTTAAC
VV    ATTGAAGCCACGTCTTTCGTGTTGCGTGAGAAAATCAGAAACATGACTCTGAATTTTAAC

NB    GAAAGACTTTTACAGTTAGTGAAGCGCGTTGCCTTTGCGACCTTGGACGTGAGTTTTCTA
VV    GAAAGACTTTTACAGTTAGTGAAGCGCGTTGCCTTTGCGACCTTGGACGTGAGTTTTCTA

NB    GATTTAGATTCAACTCTTGAATCAATAACTGATTTTGCCGAGTGTAAGGTAGCGATTGAA
VV    GATTTAGATTCAACTCTTGAATCAATAACTGATTTTGCCGAGTGTAAGGTAGCGATTGAA

NB    CTCGACGAGTTGGGTTGCTTGAGAGCGGAGGCCGAGAATGAAAAAATCAGGAATCTGGCG
VV    CTCGACGAGTTGGGTTGCTTGAGAGCGGAGGCCGAGAATGAAAAAATCAGGAATCTAGCG

NB    GGAGATTCGATTGCGGCTAAACTCGCGAGCGAGATAGTGGTCGATATTGACTCTAAGCCT
VV    GGAGATTCGATTGCGGCTAAACTCGCGAGCGAGATAGTGGTCGATATTGACTCTAAGCCT

NB    TCACCGAAGCAGGTGGGTAATTCGTCATCCGAAAACGCCGATAAGCGGGAAGTTCAGAGG
VV    TCACCGAAGCAGGTGGGTAATTCGTCATCCGAAAACGCCGATAAGCGGGAAGTTCAGAGG

NB    CCCGGTTTGCGTGGTGGTTCTAGAAACGGGGTTGTTGGGGAGTTCCTTCACTTCGTCGTG
VV    CCCGGTTTGCGTGGTGGTTCTAGGAACGGGGTTGTTGGGGAGTTCCTTCACTTCGTCGTG

NB    GATTCTGCCTTGCGTCTTTTCAAATACGCGACGGATCAACAACGGATCAAGTCTTACGTG
VV    GATTCTGCCTTGCGTCTTTTCAGATACGCGACGGATCAACAACGGATCAAGTCTTACGTG

NB    CGTTTCTTGGACTCGGCGGTCTCATTCTTGGATTACAACTACGATAATCTATCGTTTATA
VV    CGTTTCTTGGACTCGGCGGTCTCATTCTTGGATTACAACTACGATAATCTATCGTTTATA

NB    CTGCGAGTGCTTTCGGAAGGTTATTCGTGTATGTTCGCGTTTTTGGCGAATCGCGGCGAC
VV    CTGCGAGTGCTTTCGGAAGGTTATTCGTGTATGTTCGCGTTTTTGGCGAATCGCGGCGAC

NB    TTATCTAGTCGTGTCCGTAGCGCGGTGCGTGCTGTGAAAGAAGTTGCTACCTCATGCGCG
VV    TTATCTAGTCGTGTCCGTAGCGCGGTGCGTGCTGTGAAAGAAGTTGCTACCTCATGCGCG

NB    AACGCGAGCGTTTCTAAAGCCAAGGTTATGATTACCTTCGCAGCGGCCGTGTGTGCTATG
VV    AACGCGAGCGTTTCTAAAGCCAAGGTTATGATTACCTTCGCAGCGGCCGTGTGTGCTATG

NB    ATGTTTAATAGCTGCGGTTTTTCAGGCGACGGTCGGGAGTATAAATCGTATATACATCGT
VV    ATGTTTAATAGCTGCGGTTTTTCAGGCGACGGTCGGGAGTATAAATCGTATATACATCGT

NB    TACACGCAAGTATTGTTTGACACTATCTTTTTTGAGGACAGCAGTTACCTACCCATAGAA
VV    TACACGCAAGTATTGTTCGACACTATCTTTTTTGAGGACAGCAGTTACCTACCCATAGAA
```

FIG. 14D

```
NB      GTTCTGAGTTCGGCGATATGCGGTGCTATCGTCACACTTTTCTCCTCGGGCTCGTCCATA
VV      GTTCTGAGTTCGGCGATATGCGGTGCTATCGTCACACTTTTCTCCTCGGGCTCGTCCATA

NB      AGTTTAAACGCCTTCTTACTTCAAATTACCAAAGGATTCTCCCTAGAGGTTGTCGTCCGG
VV      AGTTTAAACGCCTTCTTACTTCAAATTACCAAAGGATTCTCCCTAGAGGTTGTCGTCCGG

NB      AATGTTGTGCGAGTCACGCATGGTTTGAGCACCACAGCGACCGACGGCGTCATACGTGGG
VV      AATGTTGTGCGAGTCACGCATGGTTTGAGCACCACAGCGACCGACGGCGTCATACGTGGG

NB      GTTTTCTCCCAAATTGTGTCTCACTTACTTGTTGGAAATACCGGTAATGTGGCTTACCAG
VV      GTTTTCTCCCAAATTGTGTCTCACTTACTTGTTGGAAATACCGGTAATGTGGCTTACCAG

NB      TCAGCTTTCATTGCCGGGGTGGTGCCTCTTTTAGTTAAAAAGTGTGTGAGCTTAATCTTC
VV      TCAGCTTTCATTGCCGGGGTGGTGCCTCTTTTAGTTAAAAAGTGTGTGAGCTTAATCTTC

NB      ATCTTGCGTGAAGATACTTATTCCGGTTTTATTAAGCACGGAATCAGTGAATTCTCTTTC
VV      ATCTTGCGTGAAGATACTTATTCCGGTTTTATTAAGCACGGAATCAGTGAATTCTCTTTC

NB      CTTAGTAGTATTCTGAAGTTCTTGAAGGGTAAGCTTGTGGACGAGTTGAAATCGATTATT
VV      CTTAGTAGTATTCTGAAGTTCTTGAAGGGTAAGCTTGTGGACGAGTTGAAATCGATTATT

NB      CAAGGGGTTTTTGATTCCAACAAGCACGTGTTTAAAGAAGCTACTCAGGAAGCGATTCGT
VV      CAAGGGGTTTTTGATTCCAACAAGCACGTGTTTAAAGAAGCTACTCAGGAAGCGATTCGT

NB      ACGACGGTCATGCAAGTGCCTGTCGCTGTAGTGGATGCCCTTAAGAGCGCCGCGGGAAAA
VV      ACGACGGTCATGCAAGTGCCTGTCGCTGTAGTGGATGCCCTTAAGAGCGCCGCGGGAAAA

NB      ATTTATAACAATTTTACTAGTCGACGTACCTTTGGTAAGGATGAAGGCTCCTCTAGCGAC
VV      ATTTATAACAATTTTACTAGTCGACGTACCTTTGGTAAGGATGAAGGCTCCTCTAGCGAC

NB      GGCGCATGTGAAGAGTATTTCTCATGCGACGAAGGTGAAGGTCCGGGTCTGAAAGGGGGT
VV      GGCGCATGTGAAGAGTATTTCTCATGCGACGAAGGTGAAGGTCCGGGTCTGAAAGGGGGT

NB      TCCAGCTATGGCTTCTCAATTTTAGCGTTCTTTTCACGCATTATGTGGGGAGCTCGTCGG
VV      TCCAGCTATGGCTTCTCAATTTTAGCGTTCTTTTCACGCATTATGTGGGGAGCTCGTCGG

NB      CTTATTGTTAAAGTGAAGCATGAGTGTTTTGGGAAACTTTTTGAATTTCTATCGCTCAAG
VV      CTTATTGTTAAGGTGAAGCATGAGTGTTTTGGGAAACTTTTTGAATTTCTATCGCTCAAG

NB      CTTCACGAATTCAGGACTCGCGTTTTTGGGATTGAATAGAACGGACGTGGGAGTTTACGAT
VV      CTTCACGAATTCAGGACTCGCGTTTTTGGGAAGAATGGAACGGACGTGGGAGTTTACGAT

NB      TTTTTGCCCACGGACATCGTGGAAACGCTCTCATCGATAGAAGAGTGCGACCAAATTGAA
VV      TTTTTGCCCACGGACATCGTGGAAACGCTCTCATCGATAGAAGAGTGCGACCAAATTGAA

NB      GAACTTCTCGGCGACGACCTGAAAGGTGACAAGGATGCTTCGTTGACCGATATGAATTAC
VV      GAACTTCTCGGCGACGACCTGAAAGGTGACAAGGATGCTTCGTTGACCGATATGAATTAC

NB      TTTGAGTTCTCAGAAGACTTCTTAGCCTCTGTCGAGGAGCCGCCTTTCGCTGGATTGCGA
VV      TTTGAGTTCTCAGAAGACTTCTTAGCCTCTGTCGAGGAGCCGCCTTTCGCTGGATTGCGA

NB      GGAGGTAGCAAGAACGTCGCGATTTTGGCGATTTTGGAATACGCGCATAATTTGTTTCGC
VV      GGAGGTAGCAAGAACGTCGCGATTTTGGCGATTTTGGAATACGTGCATAATTTGTTTCGC

NB      ATTGTCGCAAGCAAGTGTTCGAAACGACCTTTATTTCTTGCTTTCGCCGAACTCTCAAGC
VV      ATTGTCGCAAGCAAGTGTTCGAAACGACCTTTATTTCTTGCTTTCGCCGAACTCTCAAGC

NB      GCCCTTATCGAGAAATTTAAGGAGGTTTTCCCTCGTAAGAGCCAGCTCGTCGCTATCGTG
VV      GCCCTTATTGAGAAATTTAAGGAGGTTTTCCCTCGTAAGAGCCAGCTCGTCGCTATCGTG
```

FIG. 14E

| | |
|---|---|
| NB | CGCGAGTATACTCAGAGATTCCTCCGAAGTCGCATGCGTGCGTTGGGTTTGAATAACGAG |
| VV | CGCGAGTATACTCAGAGATTCCTCCGAAGTCGCATGCGTGCGTTGGGTTTGAATAACGAG |
| NB | TTCGTGGTAAAATCTTTCGCCGATTTGCTACCCGCATTAATGAAGCGGAAGGTTTCAGGT |
| VV | TTCGTGGTAAAATCTTTCGCCGATTTGCTACCCGCATTAATGAAGCGGAAGGTTTCAGGT |
| NB | TCGTTCTTAGCTAGTGTTTATCGCCCACTTAGAGGTTTCTCATATATGTGTGTTTCAGCG |
| VV | TCGTTCTTAGCTAGTGTTTATCGCCCACTTAGAGGTTTCTCATATATGTGTGTTTCAGCG |
| NB | GAGCGACGTGAAAAGTTTTTTGCTCTCGTGTGTTTAATCGGGTTAAGTCTCCCTTTCTTC |
| VV | GAGCGACGTGAAAAGTTTTTTGCTCTCGTGTGTTTAATCGGGTTAAGTCTCCCTTTCTTC |
| NB | GTGCGCATCGTAGGAGCGAAAGCGTGCGAAGAACTCGTGTCCTCAGCGCGTCGCTTTTAT |
| VV | GTGCGCATCGTAGGAGCGAAAGCGTGCGAAGAACTCGTGTCCTCAGCGCGTCGCCTTTAT |
| NB | GAGCGTATTAAAATTTTTCTCAGGCAGAAGTATGTCTCTCTTTCTAATTTCTTTTGTCAC |
| VV | GAGCGTATTAAAATTTTTCTAAGGCAGAAGTATGTCTCTCTTTCTAATTTCTTTTGTCAC |
| NB | TTGTTTAGCTCTGACGTTGATGACAGTTCCGCATCAGCAGGGTTGAAAGGTGGTGCGTCG |
| VV | TTGTTTAGCTCTGACGTTGATGACAGTTCCGCATCTGCAGGGTTGAAAGGTGGTGCGTCG |
| NB | CGAATGACGCTCTTCCACCTTCTGGTTCGCCTTGCTAGTGCCCTCCTATCGTTAGGGTGG |
| VV | CGAATGACGCTCTTCCACCTTCTGGTTCGCCTTGCTAGTGCCCTCCTATCGTTAGGGTGG |
| NB | GAAGGGTTAAAGCTACTCTTATCGCACCACAACTTGTTATTTTTGTGTTTTGCATTGGTT |
| VV | GAAGGGTTAAAGCTACTCTTATCGCACCACAACTTGTTATTTTTGTGTTTTGCATTGGTT |
| NB | GACGATGTGAACGTCCTTATCAAAGTTCTTGGGGGTCTTTCTTTCTTTGTGCAACCAGTC |
| VV | GACGATGTGAACGTCCTTATCAAAGTTCTTGGGGGTCTTTCTTTCTTTGTGCAACCAATC |
| NB | TTTTCCTTGTTTGCGGCGATGCTTTTACAACCGGACAGGTTTGTGGGGTATTCCGAGAAA |
| VV | TTTTCCTTGTTTGCGGCGATGCTTTTACAACCGGACAGGTTTGTGGGGTATTCCGAGAAA |
| NB | CTTGTTACAGCGTTTGAATTTTTCTTAAAATGTTCGCCTCGCGCGCCTGCACTACTCAAA |
| VV | CTTGTTACAGCGTTTGAATTTTTCTTAAAATGTTCGCCTCGCGCGCCTGCACTACTCAAA |
| NB | GGGTTTTTTGAGTGCGTGGCGAACAGCACTGTGTCAAAAACCGTTCGAAGACTTCTTCGC |
| VV | GGGTTTTTTGAGTGCGTGGCGAACAGCACTGTGTCAAAAACCGTTCGAAGACTTCTTCGT |
| NB | TATTTCGTGAGGATGCTCAAACTTCGAAAAGGGCGAGGGTTGCGTGCGGATGGTAGGGGT |
| VV | TATTTCGTGAGGATGCTCAAACTTCGAAAAGGGCGAGGGTTGCGTGCGGATGGTAGGGGT |
| NB | CTCCATCGGCAGAAAGCCGTACCCGTCATACCTTCTAATCGGGTCGTGACCGACGGGGTT |
| VV | CTCCATCGGCAGAAAGCCGTACCCGTCATACCTTCTAATCGGGTCGTGACCGACGGGGTT |
| NB | GAAAGACTTTCGGTAAAGATGCAAGGAGTTGAAGCGTTGCGTACCGAATTGAGAATCTTA |
| VV | GAAAGACTTTCGGTAAAGATGCAAGGAGTTGAAGCGTTGCGTACCGAATTGAGAATCTTA |
| NB | GAAGATTTAGATTCTGCCGTGATCGAAAAACTCAATAGACGCAGAAATCGTGACACTAAT |
| VV | GAAGATTTAGATTCTGCCGTGATCGAAAAGCTCAATAGACGCAGAAATCGTGACACTAAT |
| NB | GACGACGAATTTACGCGCCCTGCTCATGAGCAGATGCAAGAAGTCACCACTTTCTGTTCG |
| VV | GACGACGAATTTACGCGCCCTGCTCATGAGCAGATGCAAGAAGTCACCACTTTCTGTTCG |
| NB | AAAGCCAACTCTGCTGGTTTGGCCCTGGAAAGGGCAGTGCTTGTGGAAGACGCTATAAAG |
| VV | AAAGCCAACTCTGCTGGTTTGGCCCTGGAAAGGGCAGTGCTTGTGGAAGACGCTATAAAG |
| NB | TCGGAGAAACTTTCTAAGACGGTTAATGAGATGGTGAGGAAAGGGAGTACCACCAGCGAA |
| VV | TCGGAGAAACTTTCTAAGACGGTTAATGAGATGGTGAGGAAAGGGAGTACCACCAGCGAA |

FIG. 14F

```
NB    GAAGTGGCCGTCGCTTTGTCGGACGATGAAGCCGTGGAAGAAATCTCTGTTGCTGACGAG
VV    GAAGTGGCCGTCGCTTTGTCGGACGATGAAGCCGTGGAAGAAATCTCTGTTGCTGACGAG

NB    CGAGACGATTCGCCTAAGACAGTCAGGATAAGCGAATACCTAAATAGGTTAAACTCAAGC
VV    CGAGACGATTCGCCTAAGACAGTCAGGATAAGCGAATACCTAAATAGGTTAAACTCAAGC

NB    TTCGAATTCCCGAAGCCTATTGTTGTGGACGACAACAAGGATACCGGGGGTCTAACGAAC
VV    TTCGAATTCCCGAAGCCTATTGTTGTGGACGACAACAAGGATACCGGGGGTCTAACGAAC

NB    GCCGTGAGGGAGTTTTATTATATGCAAGAACTTGCTCTTTTCGAAATCCACAGCAAACTG
VV    GCCGTGAGGGAGTTTTATTATATGCAAGAACTTGCTCTTTTCGAAATCCACAGCAAACTG

NB    TGCGCCTACTACGATCAACTGCGCATAGTCAACTTCGATCGTTCCGTAGCACCATGCAGC
VV    TGCGCCTACTACGATCAACTGCGCATAGTCAATTTCGATCGTTCCTTAGCACCATGCAGC

NB    GAAGATGCTCAGCTGTACGTACGGAAGAGCGGCTCAACGATAGTGCAGGGTAAAGAGGTA
VV    GAAGATGCTCAGCTGTACGTACGGAAGAACGGCTCAACGATAGTGCAGGGTAAAGAGGTA

NB    CGTTTGCACATTAAGGATTTCCACGATCACGATTTCCTGTTTGACGGGAAAATTTCTATT
VV    CGTTTGCACATTAAGGATTTCCACGATCACGATTTCCTGTTTGACGGAAAAATTTCTATT

NB    AACAAGCGGCGGCGAGGCGGAAACGTTTTATATCACGACAACCTCGCGTTCTTGGCGAGT
VV    AACAAGCGGCGGCGAGGCGGAAACGTTTTATATCACGACAACCTCGCGTTCTTGGCGAGT

NB    AATTTGTTCTTAGCCGGCTACCCCTTTTCAAGGAGCTTCGTCTTCACGAATTCGTCGGTC
VV    AATTTGTTCTTAGCCGGCTACCCCTTTTCAAGGAGCTTCGTCTTCACGAATTCGTCGGTC

NB    GATATTCTCCTCTACGAAGCTCCACCCGGAGGTGGTAAGACGACGACGCTGATTGACTCG
VV    GATATTCTCCTCTACGAAGCTCCACCCGGAGGTGGTAAGACGACGACGCTGATTGACTCG

NB    TTCTTGAAGGTCTTCAAGAAAGGTGAGGTTTCCACCATGATCTTAACCGCCAACAAAAGT
VV    TTCTTGAAGGTCTTCAAGAAAGGTGAGGTTTCCACCATGATCTTAACCGCCAACAAAAGT

NB    TCGCAGGTTGAGATCCTAAAGAAAGTGGAGAAGGAAGTGTCTAACATTGAATGCCAGAAA
VV    TCGCAGGTTGAGATCCTAAAGAAAGTGGAGAAGGAAGTGTCTAACATTGAATGCCAGAAA

NB    CGTAAAGACAAGAGATCTCCGAAAAAGAGCATTTACACCATCGACGCTTATTTAATGCAT
VV    CGTAAAGACAAGAGATCTCCGAAAAAGAGCATTTACACCATCGACGCTTATTTAATGCAT

NB    CACCGTGGTTGTGATGCAGACGTTCTTTTCATCGATGAGTGTTTCATGGTTCATGCGGGT
VV    CACCGTGGTTGTGATGCAGACGTTCTTTTCATCGATGAGTGTTTCATGGTTCATGCGGGT

NB    AGCGTACTAGCTTGCATTGAGTTCACGAGGTGTCATAAAGTAATGATCTTCGGGGATAGC
VV    AGCGTACTAGCTTGCATTGAGTTCACGAGGTGTCATAAAGTAATGATCTTCGGGGATAGC

NB    CGGCAGATTCACTACATTGAAAGGAACGAATTGGACAAGTGTTTGTATGGGGATCTCGAT
VV    CGGCAGATCCACTACATTGAAAGGAACGAATTGGACAAGTGTTTGTATGGGGATCTCGAC

NB    AGGTTCGTGGACCTGCAGTGTCGGGTTTATGGTAATATTTCGTACCGTTGTCCATGGGAT
VV    AGGTTCGTGGACCTGCAGTGTCGGGTTTATGGTAATATTTCGTACCGTTGTCCATGGGAT

NB    GTGTGCGCTTGGTTAAGCACAGTGTATGGCAACCTAATCGCCACCGTGAAGGGTGAAAGC
VV    GTGTGCGCTTGGTTAAGCACAGTGTATGGCAACCTAATCGCCACCGTGAAGGGTGAAAGC

NB    GAAGGTAAGAGCAGCATGCGCATTAACGAAATTAATTCAGTCGACGATTTAGTCCCCGAC
VV    GAAGGTAAGAGCAGCATGCGCATTAACGAAATTAATTCAGTCGACGATTTAGTCCCCGAC

NB    GTGGGTTCCACGTTTCTGTGTATGCTTCAGTCGGAGAAGTTGGAAATCAGCAAGCACTTT
VV    GTGGGTTCCACGTTTCTGTGTATGCTTCAGTCGGAGAAGTTGGAAATCAGCAAGCACTTT
```

FIG. 14G

```
NB    ATTCGCAAGGGTTTGCCTAAACTTAACGTTCTAACTGTGCATGAGGCGCAAGGTGAGACG
VV    ATTCGCAAGGGTTTGACTAAATTTAACGTTCTAACGGTGCATGAGGCGCAAGGTGAGACG

NB    TATGCGCGTGTGAACCTTGTGCGACTTAAGTTTCAGGAGGATGAACCCTTTAAATCTATC
VV    TATGCGCGTGTGAACCTTGTGCGACTTAAGTTTCAGGAGGATGAACCCTTTAAATCTATC

NB    AGGCACATAACCGTCGCTCTTTCTCGTCACACCGACAGCTTAACTTATAACGTCTTAGCT
VV    AGGCACATAACCGTCGCTCTTTCTCGTCACACCGACAGCTTAACTTATAACGTCTTAGCT

NB    GCTCGTCGAGGTGACGCCACTTGCGATGCCATCCAGAAGGCTGCGGAATTGGTGAACAAG
VV    GCTCGTCGAGGTGACGCCACTTGCGATGCCATCCAGAAGGCTGCGGAATTGGTGAACAAG

NB    TTTCGCGTTTTTCCTACATCTTTTGGTGGTAGTGTTATCAATCTCAACGTGAAAAAGGAC
VV    TTTCGCGTTTTTCCTACATCTTTTGGTGGTAGTGTTATCAATCTCAACGTGAAGAAGGAC

NB    GTGGAAGATAACAGTAGGTGCAAGGCTTCGTCGGCACCATTGAGCGTAATCAACGACTTT
VV    GTGGAAGATAACAGTAGGTGCAAGGCTTCGTCGGCACCATTGAGCGTAATCAACGACTTT

NB    TTGAACGAAGTTAATCCCGGTACTGCGGTGATTGATTTTGGTGATTTGTCCGCGGACTTC
VV    TTGAACGAAGTTAATCCCGGTACTGCGGTGATTGATTTTGGTGATTTGTCCGCGGACTTC

NB    AGTACTGGGCCTTTTGAGTGCGGTGCCAGCGGTATTGTGGTGCGGGACAACATCTCCTCC
VV    AGTACTGGGCCTTTTGAGTGCGGTGCCAGCGGTATTGTGGTGCGGGACAACATCTCCTCC

NB    AGCAACATCACTGATCACGATAAGCAGCGTGTTTAGCGTAGTTCGGTCGCAGGCGATTCC
VV    AGCAACATCACTGATCACGATAAGCAGCGTGTTTAGCGTAGTTCGGTCGCAAGCGATTCC

NB    GCGTAGAAAACCTTCTCTACAAGAAAATTTGTATTCGTTTGAAGCGCGGAATTATAACTT
VV    GCGTAGAAAACCTTCTCTACAAGAAAATTTGTATTCGTTTGAAGCGCGGAATTATAACTT

NB    CTCGACTTGCGACCGTTACACATCTGCTTCAATGTTCGGAGAGGCTATGGCGATGAACTG
VV    CTCGACTTGCGACCGTTACACATCTGCTTCAATGTTCGGAGAGGCTATGGCGATGAACTG

NB    TCTTCGTCGTTGCTTCGACCTAGATGCCTTTTCGTCCCTGCGTAATGATGTGATTAGTAT
VV    TCTTCGTCGTTGCTTCGACCTAGATGCCTTTTCGTCCCTGCGTAATGATGTGATTAGTAT

NB    CACACGTTCAGGCATCGAACAATGGCTGGAGAAACGTACTCCTAGTCAGATTAAAGCATT
VV    CACACGTTCAGGCATCGAACAATGGCTGGAGAAACGTACTCCTAGTCAGATTAAAGCATT

NB    AATGAAGGATGTTGAATCGCCTTTGGAAATTGACGATGAAATTTGTCGTTTTAAGTTGAT
VV    AATGAAGGATGTTGAATCGCCTTTGGAAATTGACGATGAAATTTGTCGTTTTAAGTTGAT

NB    GGTGAAGCGTGACGCTAAGGTGAAGTTAGACTCTTCTTGTTTAACTAAACACAGCGCCGC
VV    GGTGAAGCGTGACGCTAAGGTGAAGTTAGACTCTTCTTGTTTAACTAAACACAGCCCCGC

NB    TCAAAATATCATGTTTCATCGCAAGAGCATTAATGCTATCTTCTCTCCTATCTTTAACGA
VV    TCAAAATATCATGTTTCATCGCAAGAGCATTAATGCTATCTTCTCTCCTATCTTTAATGA

NB    GGTGAAAAACCGAATAATGTGCTGTCTTAAGCCTAACATAAAGTTTTTTACGGAGATGAC
VV    GGTGAAAAACCGAATAATGTGCTGTCTTAAGCCTAACATAAAGTTTTTTACGGAGATGAC

NB    TAACAGGGATTTTGCTTCTGTTGTCAGCAACATGCTTGGTGACGACGATGTGTACCATAT
VV    TAACAGGGATTTTGCTTCTGTTGTCAGCAACATGCTTGGTGACGACGATGTGTACCATAT

NB    AGGTGAAGTTGATTTCTCAAAGTACGACAAGTCTCAAGATGCTTTCGTGAAGGCTTTTGA
VV    AGGTGAAGTTGATTTCTCAAAGTACGACAAGTCTCAAGATGCTTTCGTGAAGGCTTTTGA

NB    AGAAGTGATGTATAAGGAACTCGGTGTTGATGAAGAGTTGCTGGCTATCTGGATGTGCGG
VV    AGAAGTGATGTATAAGGAACTCGGTGTTGATGAAGAGTTGCTGGCTATCTGGATGTGCGG
```

FIG. 14H

| | |
|---|---|
| NB | CGAGCGGTTATCGATAGCTAACACTCTCGATGGTCAGTTGTCCTTCACGATCGAGAATCA |
| VV | CGAGCGGTTATCGATAGCTAACACTCTCGATGGTCAGTTGTCCTTCACGATCGAGAATCA |
| NB | AAGGAAGTCGGGAGCTTCGAACACTTGGATTGGTAACTCTCTCGTCACTTTGGGTATTTT |
| VV | AAGGAAGTCGGGAGCTTCGAACACTTGGATTGGTAACTCTCTCGTCACTTTGGGTATTTT |
| NB | AAGTCTTTACTACGACGTTAGAAATTTCGAGGCGTTGTACATCTCGGGCGATGATTCTTT |
| VV | AAGTCTTTACTACGACGTTAGAAATTTCGAGGCGTTGTACATCTCGGGCGATGATTCTTT |
| NB | AATTTTTTCTCGCAGCGAGATTTCGAATTATGCCGACGACATATGCACTGACATGGGTTT |
| VV | AATTTTTTCTCGCAGCGAGATTTCGAATTATGCCGACGACATATGCACTGACATGGGTTT |
| NB | TGAGACAAAATTTATGTCCCCAAGTGTCCCGTACTTTTGTTCTAAATTTGTTGTTATGTG |
| VV | TGAGACAAAATTTATGTCCCCAAGTGTCCCGTACTTTTGTTCTAAATTTGTTGTTATGTG |
| NB | TGGTCATAAGACGTTTTTTGTTCCCGACCCGTACAAGCTTTTTGTCAAGTTGGGAGCAGT |
| VV | TGGTCATAAGACGTTTTTTGTTCCCGACCCGTACAAGCTTTTCGTCAAGTTGGGAGCAGT |
| NB | CAAAGAGGATGTTTCAATGGATTTCCTTTTCGAAACTTTTACCTCCTTTAAAGACTTAAC |
| VV | CAAAGAGGATGTTTCAATGGATTTCCTTTTCGAGACTTTTACCTCCTTTAAAGACTTAAC |
| NB | CTCCGATTTTAACGACGAGCGCTTAATTCAAAAGCTCGCTGAACTTGTGGCTTTAAAATA |
| VV | CTCCGATTTTAACGACGAGCGCTTAATTCAAAAGCTCGCTGAACTTGTGGCTTTAAAATA |
| NB | TGAGGTTCAAACCGGCAACACCACCTTGGCGTTAAGTGTGATACATTGTTTGCGTTCGAA |
| VV | TGAGGTTCAAACCGGCAATACCACCTTGGCGTTAAGTGTGATACATTGTTTGCGTTCGAA |
| NB | TTTCCTCTCGTTTAGCAAGTTGTATCCTCGCGTGAAGGGATGGCAGGTTTTTTACACGTC |
| VV | TTTCCTCTCGTTTAGCAAGTTGTATCCTCGCGTGAAGGGATGGCAGGTTTTTTACACGTC |
| NB | GGTTAAGAAAGCGCTTCTCAAGAGTGGGTGTTCTCTCTTCGACAGTTTCATGACCCCTTT |
| VV | GGTTAAGAAAGCGCTTCTCAAGAGTGGGTGTTCTCTCTTCGACAGTTTCATGACCCCTTT |
| NB | TGGTCAGGCTGTCATGGTTTGGGATGATGAGTAGCGCTAACTTGTGCGCAGTTTCTTTGT |
| VV | TGGTCAGGCTGTCATGGTTTGGGATGATGAGTAGCGCTAACTTGTGCGCAGTTTCTTTGT |
| NB | TCGTGACATACACCTTGTGTGTCACCGTGCGTTTATAATGAATCAGGTTTTGCAGTTTGA |
| VV | TCGTGACATACACCTTGTGTGTCACCGTGCGTTTATAATGAATCAGGTTTTGCAGTTTGA |
| NB | ATGTTTATTTCTGCTGAATCTCGCGGTTTTTGCTGTGACTTTCATTTTCATTCTTCTGGT |
| VV | ATGTTTGTTTCTGCTGAATCTCGCGGTTTTTGCTGTGACTTTCATTTTCATTCTTCTGGT |
| NB | CTTCCGCGTGATTAAGTCTTTTCGCCAGAAGGGTCACGAAGCGCCTGTTCCCGTTGTTCG |
| VV | CTTCCGCGTGATTAAGTCTTTTCGCCAGAAGGGTCACGAAGCACCTGTTCCCGTTGTTCG |
| NB | TGGCGGGGGTTTTTCAACCGTAGTGTAGTCAAAAGACGCGCATATGGTAGTTTTCGGTTT |
| VV | TGGCGGGGGTTTTTCAACCGTAGTGTAGTCAAAAGACGCGCATATGGTAGTTTTCGGTTT |
| NB | GGACTTTGGCACCACATTCTCTACGGTGTGTGTGTACAAGGATGGACGAGTTTTTTCATT |
| VV | GGACTTTGGCACCACATTCTCTACGGTGTGTGTGTACAAGGATGGACGAGTTTTTTCATT |
| NB | CAAGCAGAATAATTCGGCGTACATCCCCACTTACCTCTATCTCTTCTCCGATTCTAACCA |
| VV | CAAGCAGAATAATTCGGCGTACATCCCCACTTACCTCTATCTCTTCTCCGATTCTAACCA |
| NB | CATGACTTTTGGTTACGAGGCCGAATCACTGATGAGTAATCTGAAAGTTAAAGGTTCGTT |
| VV | CATGACTTTTGGTTACGAGGCCGAATCACTGATGAGTAATCTGAAAGTTAAAGGTTCGTT |
| NB | TTATAGAGATTTAAAACGTTGGGTGGGTTGCGATTCGAGTAACCTCGACGCGTACCTTGA |
| VV | TTATAGAGATTTAAAACGTTGGGTGGGTTGCGATTCGAGTAACCTCGACGCGTACCTTGA |

FIG. 14I

| | |
|---|---|
| NB | CCGTTTAAAACCTCATTACTCGGTCCGCTTGGTTAAGATCGGCTCTGGCTTGAACGAAAC |
| VV | CCGTTTAAAACCTCATTACTCGGTCCGCTTGGTTAAGATCGGCTCTGGCTTGAACGAAAC |
| NB | TGTTTCAATTGGAAACTTTGGGGGCACTGTTAAGTCTGAGGCTCATCTGCCAGGGTTGAT |
| VV | TGTTTCAATTGGAAACTTCGGGGGCACTGTTAAGTCTGAGGCTCATCTGCCAGGGTTGAT |
| NB | AGCTCTCTTTATTAAGGCTGTCATTAGTTGCGCGGAGGGCGCGTTTGCGTGCACTTGCAC |
| VV | AGCTCTCTTTATTAAGGCTGTCATTAGTTGCGCGGAGGGCGCGTTTGCGTGCACTTGCAC |
| NB | CGGGGTTATTTGTTCAGTACCTGCCAATTATGATAGCGTTCAAAGGAATTTCACTGATCA |
| VV | CGGGGTTATTTGTTCAGTACCTGCCAATTATGATAGCGTTCAAAGGAATTTCACTGATCA |
| NB | GTGTGTTTCACTCAGCGGTTATCAATGCGTATATATGATCAATGAACCTTCAGCGGCTGC |
| VV | GTGTGTTTCACTCAGCGGTTATCAGTGCGTATATATGATCAATGAACCTTCAGCGGCTGC |
| NB | GCTATCTGCGTGTAATTCGGTTGGAAAGAAGTCCGCAAATTTGGCTGTTTACGATTTCGG |
| VV | GCTATCTGCGTGTAATTCGGTTGGAAAGAAGTCCGCAAATTTGGCTGTTTACGATTTCGG |
| NB | TGGTGGGACCTTCGACGTGTCTATCATTTCATACCGCAACAATACTTTTGTTGTGCGAGC |
| VV | TGGTGGGACCTTCGACGTGTCTATCATTTCATACCGCAACAATACTTTTGTTGTGCGAGC |
| NB | TTCTGGAGGCGATCTAAATCTCGGTGGAAGGGATGTTGATCGTGCGTTTCTCACGCACCT |
| VV | TTCTGGAGGCGATCTAAATCTCGGTGGAAGGGATGTTGATCGTGCGTTTCTCACGCACCT |
| NB | CTTCTCTTTAACATCGCTGGAACCTGACCTCACTTTGGATATCTCGAATCTGAAAGAATC |
| VV | CTTCTCTTTAACATCGCTGGAACCTGACCTCACTTTGGATGTCTCGAATCTGAAAGAATC |
| NB | TTTATCAAAAACGGACGCAGAGATAGTTTACACTTTGAGAGGTGTCGATGGAAGAAAAGA |
| VV | TTTATCAAAAACGGACGCAGAGATAGTTTACACTTTGAGAGGTGTCGATGGAAGAAAAGA |
| NB | AGACGTTAGAGTAAACAAAAACATTCTTACGTCGGTGATGCTCCCCTACGTGAACAGAAC |
| VV | AGACGTTAGAGTAAACAAAAACATTCTTACGTCGGTGATGCTCCCCTACGTGAACAGAAC |
| NB | GCTTAAGATATTAGAGTCAACCTTAAAAACGTATGCTAAGAGTATGAATGAGAGTGCGCG |
| VV | GCTTAAGATATTAGAGTCAACCTTAAAATCGTATGCTAAGAGTATGAATGTGAGTGCGCG |
| NB | AGTTAAGTGCGATTTAGTGCTGATAGGAGGATCTTCATATCTTCCTGGCCTGGCAGACGT |
| VV | AGTTAAGTGCGATTTAGTGCTGATAGGAGGATCTTCATATCTTCCTGGCCTGGCAGACGT |
| NB | ACTAACGAAGCATCAGAGCGTTGATCGTATCTTAAGAGTTTCGGATCCTCGGGCTGCCGT |
| VV | ACTAACGAAGCATCAGAGCGTTGATCGTATCTTAAGAGTTTCGGATCCTCGGGCTGCCGT |
| NB | GGCCGTCGGTTGCGCACTATATTCTTCATGCCTCTCAGGATCTGGGGGGTTGCTACTGAT |
| VV | GGCCGTCGGTTGCGCATTATATTCTTCATGCCTCTCAGGATCTGGGGGGTTGCTACTGAT |
| NB | CGACTGTGCAGCTCACACTGTCGCTATAGCGGACAGAAGTTGTCAGCAAATCATTTGCGC |
| VV | CGACTGTGCAGCTCACACTGTCGCTATAGCGGACAGAAGTTGTCATCAAATCATTTGCGC |
| NB | TCCAGCGGGGGCACCGATCCCCTTTTCAGGAAGCATGCCTTTGTACTTAGCCAGGGTCAA |
| VV | TCCAGCGGGGGCACCGATCCCCTTTTCAGGAAGCATGCCTTTGTACTTAGCCAGGGTCAA |
| NB | CAAGAACTCGCAGCGTGAAATCGCCGTGTTTGAAGGGGAGTACGTTAAGTGCCCTAAGAA |
| VV | CAAGAACTCGCAGCGTGAAGTCGCCGTGTTTGAAGGGGAGTACGTTAAATGCCCTAAGAA |
| NB | CAGAAAGATCTGTGGAGCAAATATAAGATTTTTTGATATAGGAGTGACGGGTGATTCGTA |
| VV | CAGAAAGATCTGTGGAGCAAATATAAGATTTTTTGATATAGGAGTGACGGGTGATTCGTA |
| NB | CGCACCCGTTACCTTCTATATGGATTTCTCCATTTCAAGCGTAGGAGCCGTTTCATTCGT |
| VV | CGCACCCGTTACCTTCTATATGGATTTCTCCATTTCAAGCGTAGGAGCCGTTTCATTCGT |

FIG. 14J

| | |
|---|---|
| NB | GGTGAGAGGTCCTGAGGGTAAGCAAGTGTCACTCACTGGAACTCCAGCGTATAACTTTTC |
| VV | GGTGAGAGGTCCTGAGGGTAAGCAAGTGTCACTCACTGGAACTCCAGCGTATAACTTTTC |
| NB | GTCTGTGGCTCTCGGATCACGCAGTGTCCGAGAATTGCATATTAGTTTAAATAATAAAGT |
| VV | GTCTGTGGCTCTCGGATCACGCAGTGTCCGAGAATTGCATATTAGTTTAAATAATAAAGT |
| NB | TTTTCTCGGTTTGCTTCTACATAGAAAGGCGGATCGACGAATACTTTTCACTAAGGATGA |
| VV | TTTTCTCGGTTTGCTTCTACATAGAAAGGCGGATCGACGAATACTTTTCACTAAGGATGA |
| NB | AGCGATTCGATACGCCGATTCAATTGATATCGCGGATGTGCTAAAGGAATATAAAAGTTA |
| VV | AGCGATTCGATACGCCGATTCAATTGATATCGCGGATGTGCTAAAGGAATATAAAAGTTA |
| NB | CGCGGCCAGTGCCTTACCACCAGACGAGGATGTCGAATTACTCCTGGGAAAGTCTGTTCA |
| VV | CGCGGCCAGTGCCTTACCACCAGACGAGGATGTCGAATTACTCCTGGGAAAGTCTGTTCA |
| NB | AAAAGTTTTACGGGGAAGCAGACTGGAAGAAATACCTCTCTAGGAGCATAGCAGCACACT |
| VV | AAAAGTTTTACGGGGAAGCAGACTGGAAGAAATACCTCTCTAGGAGCATAGCAGCACACT |
| NB | CAAGTGAAATTAAAACTCTACCAGACATTCGATTGTACGGCGGTAGGGTTGTAAAGAAGT |
| VV | CAAGTGAAATTAAAACTCTACCAGACATTCGATTGTACGGCGGTAGGGTTGTAAAGAAGT |
| NB | CCGATTTCGAATCAGCACTTCCTAATTCTTTTGAACAGGAATTAGGACTGTTCATACTGA |
| VV | CCGATTTCGAATCAGCACTTCCTAATTCTTTTGAACAGGAATTAGGACTGTTCATACTGA |
| NB | GCGAACGGGAAGTGGGATGGAGCAAATTATGCGGAATAACGGTGGAAGAAGCAGCATACG |
| VV | GCGAACGGGAAGTGGGATGGAGCAAATTATGCGGAATAACGGTGGAAGAAGCAGCATACG |
| NB | ATCTTACGAATCCCAAGGCTTATAAATTCACTGCCGAGACATGTAGCCCGGATGTAAAAG |
| VV | ATCTTACGAATCCCAAGGCTTATAAATTCACTGCCGAGACATGTAGCCCGGATGTAAAAG |
| NB | GTGAAGGACAAAAATACTCTATGGAAGACGTGATGAATTTCATGCGTTTATCAAATCTGG |
| VV | GTGAAGGACAAAAATACTCTATGGAAGACGTGATGAATTTCATGCGTTTATCAAATCTGG |
| NB | ATGTTAACGACAAGATGCTGGCGGAACAGTGTTGGTCGCTGTCCAATTCATGCGGTGAAT |
| VV | ATGTTAACGACAAGATGCTGGCGGAACAGTGTTGGTCGCTGTCCAATTCATGCGGTGAAT |
| NB | TGATCAACCCAGACGACAAAGGGCGATTCGTGGCTCTCACCTTTAAGGACAGAGACACAG |
| VV | TGATCAACCCAGACGACAAAGGGCGATTCGTGGCTCTCACCTTTAAGGACAGAGACACAG |
| NB | CTGATGACACGGGTGCCGCCAACGTGGAATGTCGCGTGGGCGACTATCTAGTTTACGCTA |
| VV | CTGATGACACGGGTGCCGCCAACGTGGAATGTCGCGTGGGCGACTATCTAGTTTACGCTA |
| NB | TGTCCCTGTTTGAGCAGAGGACCCAAAAATCGCAGTCTGGCAACATCTCTCTGTACGAAA |
| VV | TGTCCCTGTTTGAGCAGAGGACCCAAAAATCGCAGTCTGGCAACATCTCTCTGTACGAAA |
| NB | AGTACTGCGAATACATCAGGACCTACTTAGGGAGTACAGACCTGTTTTTCACAGCGCCGG |
| VV | AGTACTGCGAATATATCAGGACCTACTTAGGGAGTACGGACCTGTTTTTCACAGCGCCGG |
| NB | ACAGGATTCCGTTACTTACGGGCATCCTATACGATTTTTGTAAGGAATACAACATTTTCT |
| VV | ACAGGATTCCGTTACTTACGGGCATCCTGTACGATTTTTGTAAGGAATACAACATTTTCT |
| NB | ACTCGTCATATAAGAGAAACGTCGATAATTTCAGATTCTTCTTGGCGAATTATATGCCTT |
| VV | ACTCGTCATATAAGAGAAACGTCGATAATTTCAGATTCTTCTTGGCAAATTATATGCCTT |
| NB | TGATATCTGACGTCTTTGTCTTCCAGTGGGTAAAACCCGCGCCGGATGTTCGGCTGCTTT |
| VV | TGATATCTGACGTCTTTGTCTTCCAGTGGGTAAAACCCGCGCCGGATGTTCGGCTGCTTT |
| NB | TTGAGTTAAGTGCAGCGGAACTAACGCTGGAGGTTCCCACACTGAGTTTGATAGATTCTC |
| VV | TTGAGTTAAGTGCAGCGGAACTAACGCTGGAGGTTCCCACACTGAGTTTGATAGATTCTC |

FIG. 14K

```
NB    AAGTTGTGGTAGGTCATATCTTAAGATACGTAGAATCCTACACATCAGATCCAGCCATCG
VV    AAGTTGTGGTAGGCCATATCTTAAGATACGTAGAATCCTACACATCAGATCCAGCCATCG

NB    ACGCGTTAGAAGACAAACTGGAAGCGATACTGAAAAGTAGCAATCCCCGTCTATCGACAG
VV    ACGCGTTAGAAGACAAACTGGAAGCGATACTGAAAAGTAGCAATCCCCGTCTATCGACAG

NB    CGCAACTATGGGTTGGTTTCTTTTGTTACTATGGTGAGTTTCGTACGGCTCAAAGTAGAG
VV    CGCAACTATGGGTTGGTTTCTTTTGTTACTATGGTGAGTTTCGTACGGCTCAAAGTAGAG

NB    TAGTGCAAAGACCAGGCGTATACAAAACACCTGACTCAGTGGGTGGATTTGAAATAAACA
VV    TAGTGCAAAGACCAGGCGTATACAAAACACCTGACTCAGTGGGTGGATTTGAAATAAACA

NB    TGAAAGATGTTGAGAAATTCTTCGATAAACTTCAGAGAGAATTGCCTAATGTATCTTTGC
VV    TGAAAGATGTTGAGAAATTCTTCGATAAACTTCAGAGAGAATTGCCTAATGTATCTTTGC

NB    GGCGTCAGTTTAACGGAGCTAGAGCGCATGAGGCTTTCAAAATATTTAAAAACGGAAATA
VV    GGCGTCAGTTTAACGGAGCTAGAGCGCATGAGGCTTTCAAAATATTTAAAAACGGAAATA

NB    TAAGTTTCAAACCTATATCGCGTTTAAACGTGCCTAGAGAGTTCTGGTATCTGAACATAG
VV    TAAGTTTCAGACCTATATCGCGTTTAAACGTGCCCAGAGAGTTCTGGTATCTGAACATAG

NB    ACTACTTCAGGCACGCGAATAGGTCCGGGTTAACCGAAGAAGAAATACTCATCCTAAACA
VV    ACTACTTCAGGCACGCGAATAGGTCCGGGTTAACCGAAGAAGAAATACTCATCCTAAACA

NB    ACATAAGCGTTGATGTTAGGAAGTTATGCGCTGAGAGAGCGTGCAATACCCTACCTAGCG
VV    ACATAAGCGTTGATGTTAGGAAGTTATGCGCTGAGAGAGCGTGCAATACCCTACCTAGCG

NB    CGAAGCGCTTTAGTAAAAATCATAAGAGTAATATACAATCATCACGCCAAGAGCGGAGGA
VV    CGAAGCGCTTTAGTAAAAATCATAAGAGTAATATACAATCATCACGCCAAGAGCGGAGGA

NB    TTAAAGACCCATTGGTAGTCCTGAAAGACACTTTATATGAGTTCCAACGCAAGCGTGCCG
VV    TTAAAGACCCATTGGTAGTCCTGAAAGACACTTTATATGAGTTCCAACACAAGCGTGCCG

NB    GTTGGGGGTCTCGAAGCACTCGAGACCTCGGGAGTCGTGCTGACCACGCGAAAGGAAGCG
VV    GTTGGGGGTCTCGAAGCACTCGAGACCTCGGGAGTCGTGCTGACCACGCGAAAGGAAGCG

NB    GTTGATAAGTTTTTTAATGAACTAAAAAACGAAAATTACTCATCAGTTGACAGCAGCCGA
VV    GTTGATAAGTTTTTCAATGAACTAAAAAACGAAAATTACTCATCAGTTGACAGCAGCCGA

NB    TTAAGCGATTCGGAAGTAAAAGAAGTGTTAGAGAAAAGTAAAGAAAGTTTCAAAAGCGAA
VV    TTAAGCGATTCGGAAGTAAAAGAAGTGTTAGAGAAAAGTAAAGAAAGTTTCAAAAGCGAA

NB    CTGGCCTCCACTGACGAGCACTTCGTCTACCACATTATATTTTTCTTAATCCGATGTGCT
VV    CTGGCCTCCACTGACGAGCACTTCGTCTACCACATTATATTTTTCTTAATCCGATGTGCT

NB    AAGATATCGACGAGTGAAAAAGTGAAGTACGTTGGTAGTCATACGTACGTGGTCGACGGA
VV    AAGATATCGACGAGTGAAAAGGTGAAGTACGTTGGTAGTCATACGTACGTGGTCGACGGA

NB    AAAACGTACACCGTTCTTGACGCTTGGGTATTCAACATGATGAAAAGTCTCACGAAGAAG
VV    AAAACGTACACCGTTCTTGACGCTTGGGTATTCAACATGATGAAAAGTCTCACGAAGAAG

NB    TACAAACGAGTGAATGGTCTGCGTGCGTTCTGTTGCGCGTGCGAAGATCTATATCTAACC
VV    TACAAACGAGTGAATGGTCTGCGTGCGTTCTGTTGCGCGTGCGAAGATCTATATCTAACC

NB    GTCGCACCAATAATGTCAGAACGCTTTAAGACTAAAGCCGTAGGGATGAAAGGTTTGCCT
VV    GTCGCACCAATAATGTCAGAACGCTTTAAGACTAAAGCCGTAGGGATGAAAGGTTTGCCT

NB    GTTGGAAAGGAATACTTAGGCGCCGACTTTCTTTCGGGAACTAGCAAACTGATGAGCGAT
VV    GTTGGAAAGGAATACTTAGGCGCCGACTTTCTTTCGGGAACTAGCAAACTGATGAGCGAT
```

FIG. 14L

```
NB    CACGACAGGGCGGTCTCCATCGTTGCAGCGAAAAACGCTGTCGATCGTAGCGCTTTCACG
VV    CACGACAGGGCGGTCTCCATCGTTGCAGCGAAAAACGCTGTCGATCGTAGCGCTTTCACG

NB    GGTGGGGAGAGAAAGATAGTTAGTTTGTATGATCTAGGGAGGTACTAAGCACGGTGTGCT
VV    GGTGGGGAGAGAAAGATAGTTAGTTTGTATGATCTAGGGAGGTACTAAGCACGGTGTGCT

NB    ATAGTGCGTGCTATAATAATAAACACTAGTGCTTAAGTCGCGCAGAAGAAAACGCTTAAT
VV    ATAGTGCGTGCTATAATAATAAACACTAGTGCTTAAGTCGCGCAGAAGAAAACGCTTAAT

NB    TAACAATGAAGACTAATCTTTTTCTCTTTCTCATCTTTTCACTTCTCCTATCATTATCCT
VV    TAACAATGAAGACTAATCTTTTTCTCTTTCTCATCTTTTCACTTCTCCTATCATTATCCT

NB    CGGCCGAATTCAGTAAAGGAGAAGAACTTTTCACTGGAGTTGTCCCAATTCTTGTTGAAT
VV    CGGCCGAATTCAGTAAAGGAGAAGAACTTTTCACTGGAGTTGTCCCAATTCTTGTTGAAT

NB    TAGATGGTGATGTTAATGGGCACAAATTTTCTGTCAGTGGAGAGGGTGAAGGTGATGCAA
VV    TAGATGGTGATGTTAATGGGCACAAATTTTCTGTCAGTGGAGAGGGTGAAGGTGATGCAA

NB    CATACGGAAAACTTACCCTTAAATTTATTTGCACTACTGGAAAACTACCTGTTCCATGGC
VV    CATACGGAAAACTTACCCTTAAATTTATTTGCACTACTGGAAAACTACCTGTTCCATGGC

NB    CAACACTTGTCACTACTTTCTCTTATGGTGTTCAATGCTTTTCAAGATACCCAGATCATA
VV    CAACACTTGTCACTACTTTCTCTTATGGTGTTCAATGCTTTTCAAGATACCCAGATCATA

NB    TGAAGCGGCACGACTTCTTCAAGAGCGCCATGCCTGAGGGATACGTGCAGGAGAGGACCA
VV    TGAAGCGGCACGACTTCTTCAAGAGCGCCATGCCTGAGGGATACGTGCAGGAGAGGACCA

NB    TCTTCTTCAAGGACGACGGGAACTACAAGACACGTGCTGAAGTCAAGTTTGAGGGAGACA
VV    TCTTCTTCAAGGACGACGGGAACTACAAGACACGTGCTGAAGTCAAGTTTGAGGGAGACA

NB    CCCTCGTCAACAGGATCGAGCTTAAGGGAATCGATTTCAAGGAGGACGGAAACATCCTCG
VV    CCCTCGTCAACAGGATCGAGCTTAAGGGAATCGATTTCAAGGAGGACGGAAACATCCTCG

NB    GCCACAAGTTGGAATACAACTACAACTCCCACAACGTATACATCATGGCCGACAAGCAAA
VV    GCCACAAGTTGGAATACAACTACAACTCCCACAACGTATACATCATGGCCGACAAGCAAA

NB    AGAACGGCATCAAAGCCAACTTCAAGACCCGCCACAACATCGAAGACGGCGGCGTGCAAC
VV    AGAACGGCATCAAAGCCAACTTCAAGACCCGCCACAACATCGAAGACGGCGGCGTGCAAC

NB    TCGCTGATCATTATCAACAAAATACTCCAATTGGCGATGGCCCTGTCCTTTTACCAGACA
VV    TCGCTGATCATTATCAACAAAATACTCCAATTGGCGATGGCCCTGTCCTTTTACCAGACA

NB    ACCATTACCTGTCCACACAATCTGCCCTTTCGAAAGATCCCAACGAAAAGAGAGACCACA
VV    ACCATTACCTGTCCACACAATCTGCCCTTTCGAAAGATCCCAACGAAAAGAGAGACCACA

NB    TGGTCCTTCTTGAGTTTGTAACAGCTGCTGGGATTACACATGGCATGGATGAACTATACA
VV    TGGTCCTTCTTGAGTTTGTAACAGCTGCTGGGATTACACATGGCATGGATGAACTATACA

NB    AACATGATGAGCTTTAGGCCGGCCTAAACTGTTCCTGAATAGAACCATTGGCAAACGTGG
VV    AACATGATGAGCTTTAGGCCGGCCTAAACTGTTCCTGAATAGAACCATTGGCAAACGTGG

NB    GATCCCGTCAGGGTATGAGTTCCTCGGGGCAGATTTTCTAACTGCGACCAGCGTGTGTTT
VV    GATCCCGTCAGGGTATGAGTTCCTCGGGGCAGATTTTCTAACTGCGACCAGCGTGTGTTT

NB    GAACGATCACGAAAAAGCTATCGTACTACAGGCCTCAAGAGCTGCCATTGATAGAGCAGT
VV    GAACGATCACGAAAAAGCTATCGTACTACAGGCCTCAAGAGCTGCCATTGATAGAGCAGT

NB    CTCTTCGTCGGTCGACGGGAAGATCGTCAGTCTTTTCGACCTCGGTCGTCTTAGTTAACA
VV    CTCTTCGTCGGTCGACGGGAAGATCGTCAGTCTTTTCGACCTCGGTCGTCTTAGTTAACA
```

FIG. 14M

```
NB    CAGTTACTAAGGTTCCATTTTATTATTGCATTGTTTTTCATTTAGTGTAATCGTACTTGA
VV    CAGTTACTAAGGTTCCATTTTATTATTGCATTGTTTTTCATTTAGTGTAATCGTACTTGA

NB    GTTCTAATCCTGCAGGCTATGGAGTTGATGTCCGACAGCAACCTTAGCAACCTGGTGATA
VV    GTTCTAATCCTGCAGGCTATGGAGTTGATGTCCGACAGCAACCTTAGCAACCTGGTGATA

NB    ACCGACGCCTCTAGTCTAAATGGTGTCGACAAGAAGCTTTTATCTGCTGAAGTTGTAAAA
VV    ACCGACGCCTCTAGTCTAAATGGTGTCGACAAGAAGCTTTTATCTGCTGAAGTTGTAAAA

NB    ATGCTGGTGCAGAAAGGGGCTCCTAACGAGGGTATAGAAGTGGTGTTCGGTCTACTCCTT
VV    ATGTTGGTGCAGAAAGGGGCTCCTAACGAGGGTATAGAAGTGGTGTTCGGTCTACTCCTT

NB    TACGCACTCGCGGCAAGAACCACGTCTCCTAAGGTTCAGCGCGCAGATTCAGACGTTATA
VV    TACGCACTCGCGGCAAGAACCACGTCTCCTAAGGTTCAGCGCGCAGATTCAGACGTTATA

NB    TTTTCAAATAGTTTCGGAGAGAGGAATGTGGTAGTAACAGAGGGTGACCTTAAGAAGGTA
VV    TTTTCAAATAGTTTCGGAGAGAGGAATGTGGTAGTAACAGAGGGTGACCTTAAGAAGGTA

NB    CTCGACGGGTGTGCGCCTCTCACTAGGTTCACTAATAAACTTAGAACGTTCGGTCGTACT
VV    CTCGACGGGTGTGCGCCTCTCACTAGGTTCACTAATAAACTTAGAACGTTCGGTCGTACT

NB    TTCACTGAGGCTTACGTTGACTTTTGTATCGCGTATAAGCACAAATTACCCCAACTCAAC
VV    TTCACTGAGGCTTACGTTGACTTTTGTATCGCGTATAAGCACAAATTACCCCAACTCAAC

NB    GCCGCGGCGGAATTGGGGATTCCAGCTGAAGATTCGTACTTAGCTGCAGATTTTCTGGGT
VV    GCTGCGGCGGAATTGGGGATTCCAGCTGAAGATTCGTACTTAGCTGCAGATTTTCTGGGT

NB    ACTTGCCCGAAGCTCTCTGAATTACAGCAAAGTAGGAAGATGTTCGCGAGTATGTACGCT
VV    ACTTGCCCGAAGCTCTCTGAATTACAGCAAAGTAGGAAGATGTTCGCGAGTATGTACGCT

NB    CTAAAAACTGAAGGTGGAGTGGTAAATACACCAGTGAGCAATCTGCGTCAGCTAGGTAGA
VV    CTTAAAACTGAAGGTGGAGTGGTAAATACGCCAGTGAGCAATCTGCGTCAGCTAGGTAGA

NB    AGGGAAGTTATGTAATGGAAGATTACGAAGAAAAATCCGAATCGCTCATACTGCTACGCA
VV    AGGGAAGTTATGTAATGGAAGATTACGAAGAAAAATCCGAATCGCTCATACTGCTACGCA

NB    CGAATCTGAACACTATGCTTTTAGTGGTCAAGTCCGATGCTAGTGTAGAGCTGCCTAAAC
VV    CGAATCTGAACACTATGCTTTTAGTGGTCAAGTCCGATGCTAGTGTAGAGCTGCCTAAAC

NB    TACTAATTTGCGGTTACTTACGAGTGTCAGGACGTGGGGAGGTGACGTGTTGCAACCGTG
VV    TACTAATTTGCGGTTACTTACGAGTGTCAGGACGTGGGGAGGTGACGTGTTGCAACCGTG

NB    AGGAATTAACAAGAGATTTTGAGGGCAATCATCATACGGTGATCCGTTCTAGAATCATAC
VV    AGGAATTAACAAGAGATTTTGAGGGCAATCATCATACGGTGATCCGTTCTAGAATCATAC

NB    AATATGACAGCGAGTCTGCTTTTGAGGAATTCAACAACTCTGATTGCGTAGTGAAGTTTT
VV    AATATGACAGCGAGTCTGCTTTTGAGGAATTCAACAACTCTGATTGCGTAGTGAAGTTTT

NB    TCCTAGAGACTGGTAGTGTCTTTTGGTTTTTCCTTCGAAGTGAAACCAAAGGTAGAGCGG
VV    TCCTAGAGACTGGTAGTGTCTTTTGGTTTTTCCTTCGAAGTGAAACCAAAGGTAGAGCGG

NB    TGCGACATTTGCGCACCTTCTTCGAAGCTAACAATTTCTTCTTTGGATCGCATTGCGGTA
VV    TGCGACATTTGCGCACCTTCTTCGAAGCTAACAATTTCTTCTTTGGATCGCATTGCGGTA

NB    CCATGGAGTATTGTTTGAAGCAGGTACTATCTGAAACTGAATCTATAATCGATTCTTTTT
VV    CCATGGAGTATTGTTTGAAGCAGGTACTAACTGAAACTGAATCTATAATCGATTCTTTTT

NB    GCGAAGAAAGAAATCGTTAAGATGAGGGTTATAGTGTCTCCTTATGAAGCTGAAGACATT
VV    GCGAAGAAAGAAATCGTTAAGATGAGGGTTATAGTGTCTCCTTATGAAGCTGAAGACATT
```

FIG. 14N

```
NB    CTGAAAAGATCGACTGACATGTTACGAAACATAGACAGTGGGGTCTTGAGCACTAAAGAA
VV    CTGAAAAGATCGACTGACATGTTACGAAACATAGACAGTGGGGTCTTGAGCACTAAAGAA

NB    TGTATCAAGGCATTCTCGACGATAACGCGAGACCTACATTGTGCGAAGGCTTCCTACCAG
VV    TGTATCAAGGCATTCTCGACGATAACGCGAGACCTACATTGTGCGAAGGCTTCCTACCAG

NB    TGGGGTGTTGACACTGGGTTATATCAGCGTAATTGCGCTGAAAAACATTTAATTGACACG
VV    TGGGGTGTTGACACTGGGTTATATCAGCGTAATTGCGCTGAAAAACGTTTAATTGACACG

NB    GTGGAGTCAAACATACGGTTGGCTCAACCTCTCGTGCGTGAAAAAGTGGCGGTTCATTTT
VV    GTGGAGTCAAACATACGGTTGGCTCAACCTCTCGTGCGTGAAAAAGTGGCGGTTCATTTT

NB    TGTAAGGATGAACCAAAAGAGCTAGTAGCATTCATCACGCGAAAGTACGTGGAACTCACG
VV    TGTAAGGATGAACCAAAAGAGCTAGTAGCATTCATCACGCGAAAGTACGTGGAACTCACG

NB    GGCGTGGGAGTGAGAGAAGCGGTGAAGAGGGAAATGCGCTCTCTTACCAAAACAGTTTTA
VV    GGCGTGGGAGTGAGAGAAGCGGTGAAGAGGGAAATGCGCTCTCTTACCAAAACAGTTTTA

NB    AATAAAATGTCTTTGGAAATGGCGTTTTACATGTCACCACGAGCGTGGAAAAACGCTGAA
VV    AATAAAATGTCTTTGGAAATGGCGTTTTACATGTCACCACGAGCGTGGAAAAACGCTGAA

NB    TGGTTAGAACTAAAATTTTCACCTGTGAAAATCTTTAGAGATCTTTTATTAGACGTGGAA
VV    TGGTTAGAACTAAAATTTTCACCTGTGAAAATCTTTAGAGATCTGCTATTAGACGTGGAA

NB    ACGCTCAACGAATTGTGCGCCGAAGATGATGTTCACGTCGACAAAGTAAATGAGAATGGG
VV    ACGCTCAACGAATTGTGCGCCGAAGATGATGTTCACGTCGACAAAGTAAATGAGAATGGG

NB    GACGAAAATCACGACCTCGAACTCCAAGACGAATGTTAAACATTGGTTAAGTTTAACGAA
VV    GACGAAAATCACGACCTCGAACTCCAAGACGAATGTTAAACATTGGTTAAGTTTAACGAA

NB    AATGATTAGTAAATAATAAATCGAACGTGGGTGTATCTACCTGACGTATCAACTTAAGCT
VV    AATGATTAGTAAATAATAAATCGAACGTGGGTGTATCTACCTGACGTATCAACTTAAGCT

NB    GTTACTGAGTAATTAAACCAACAAGTGTTGGTGTAATGTGTATGTTGATGTAGAGAAAAA
VV    GTTACTGAGTAATTAAACCAACAAGTGTTGGTGTAATGTGTATGTTGATGTAGAGAAAAA

NB    TCCGTTTGTAGAACGGTGTTTTTCTCTTCTTTATTTTTAAAAAAAAATAAAAAAAAAAAA
VV    TCCGTTTGTAGAACGGTGTTTTTCTCTTCTTTATTTTTAAAAAAAAATAAAAAAAAAAAA

NB    AAAGAAGC
VV    AAAGAAGC
```

FIG. 14O

SEQUENCE LISTING

```
<160> NUMBER OF SEQ ID NOS: 11

<210> SEQ ID NO 1
<211> LENGTH: 22166
<212> TYPE: DNA
<213> ORGANISM: Artificial sequence
<220> FEATURE:
<223> OTHER INFORMATION: Engineered viral vector
<220> FEATURE:
<221> NAME/KEY: misc_feature
<222> LOCATION: (1)..(3305)
<223> OTHER INFORMATION: Sequence from binary vector pCB301
<220> FEATURE:
<221> NAME/KEY: misc_feature
<222> LOCATION: (3306)..(21957)
<223> OTHER INFORMATION: Viral expression cassette
<220> FEATURE:
<221> NAME/KEY: promoter
<222> LOCATION: (3306)..(4063)
<223> OTHER INFORMATION: 35S promoter
<220> FEATURE:
<221> NAME/KEY: misc_feature
<222> LOCATION: (4064)..(21643)
<223> OTHER INFORMATION: Viral sequence
<220> FEATURE:
<221> NAME/KEY: misc_feature
<222> LOCATION: (18648)..(19439)
<223> OTHER INFORMATION: GFP-reporter expression cassette
<220> FEATURE:
<221> NAME/KEY: promoter
```

```
<222> LOCATION: (19440)..(19723)
<223> OTHER INFORMATION: heterologous BYV CP promoter
<220> FEATURE:
<221> NAME/KEY: misc_feature
<222> LOCATION: (21644)..(21698)
<223> OTHER INFORMATION: ribozyme
<220> FEATURE:
<221> NAME/KEY: terminator
<222> LOCATION: (21705)..(21957)
<223> OTHER INFORMATION: NOS terminator

<400> SEQUENCE: 1

cgctcaccgg gctggttgcc ctcgccgctg ggctggcggc cgtctatggc cctgcaaacg     60

cgccagaaac gccgtcgaag ccgtgtgcga gacaccgcgg ccgccggcgt tgtggatacc    120

tcgcggaaaa cttggccctc actgacagat gaggggcgga cgttgacact tgaggggccg    180

actcacccgg cgcggcgttg acagatgagg ggcaggctcg atttcggccg gcgacgtgga    240

gctggccagc ctcgcaaatc ggcgaaaacg cctgatttta cgcgagtttc ccacagatga    300

tgtggacaag cctggggata agtgccctgc ggtattgaca cttgaggggc gcgactactg    360

acagatgagg ggcgcgatcc ttgacacttg aggggcagag tgctgacaga tgaggggcgc    420

acctattgac atttgagggg ctgtccacag gcagaaaatc cagcatttgc aagggtttcc    480

gcccgttttt cggccaccgc taacctgtct tttaacctgc ttttaaacca atatttataa    540

accttgtttt taaccagggc tgcgccctgt gcgcgtgacc gcgcacgccg aagggggggtg    600

cccccccttc tcgaaccctc ccggcccgct ctcgagttgg cagcatcacc cataattgtg    660

gtttcaaaat cggctccgtc gatactatgt tatacgccaa ctttgaaaac aactttgaaa    720

aagctgtttt ctggtattta aggttttaga atgcaaggaa cagtgaattg gagttcgtct    780

tgttataatt agcttcttgg ggtatcttta aatactgtag aaaagaggaa ggaaataata    840

aatggctaaa atgagaatat caccggaatt gaaaaaactg atcgaaaaat accgctgcgt    900

aaaagatacg gaaggaatgt ctcctgctaa ggtatataag ctggtgggag aaaatgaaaa    960

cctatattta aaaatgacgg acagccggta taaagggacc acctatgatg tggaacggga   1020

aaaggacatg atgctatggc tggaaggaaa gctgcctgtt ccaaaggtcc tgcactttga   1080

acggcatgat ggctggagca atctgctcat gagtgaggcc gatggcgtcc tttgctcgga   1140

agagtatgaa gatgaacaaa gccctgaaaa gattatcgag ctgtatgcgg agtgcatcag   1200

gctctttcac tccatcgaca tatcggattg tccctatacg aatagcttag acagccgctt   1260

agccgaattg gattacttac tgaataacga tctggccgat gtggattgcg aaaactggga   1320

agaagacact ccatttaaag atccgcgcga gctgtatgat tttttaaaga cggaaaagcc   1380

cgaagaggaa cttgtctttt cccacggcga cctgggagac agcaacatct ttgtgaaaga   1440

tggcaaagta agtggcttta ttgatcttgg gagaagcggc agggcggaca agtggtatga   1500

cattgccttc tgcgtccggt cgatcaggga ggatatcggg gaagaacagt atgtcgagct   1560

attttttgac ttactgggga tcaagcctga ttgggagaaa ataaaatatt atattttact   1620

ggatgaattg ttttagtacc tagatgtggc gcaacgatgc cggcgacaag caggagcgca   1680

ccgacttctt ccgcatcaag tgttttggct ctcaggccga ggcccacggc aagtatttgg   1740

gcaaggggtc gctggtattc gtgcagggca agattcggaa taccaagtac gagaaggacg   1800

gccagacggt ctacgggacc gacttcattg ccgataaggt ggattatctg gacaccaagg   1860

caccaggcgg gtcaaatcag gaataagggc acattgcccc ggcgtgagtc ggggcaatcc   1920

cgcaaggagg gtgaatgaat cggacgtttg accggaaggc atacaggcaa gaactgatcg   1980

acgcggggtt ttccgccgag gatgccgaaa ccatcgcaag ccgcaccgtc atgcgtgcgc   2040
```

-continued

```
cccgcgaaac cttccagtcc gtcggctcga tggtccagca agctacggcc aagatcgagc   2100
gcgacagcgt gcaactggct ccccctgccc tgcccgcgcc atcggccgcc gtggagcgtt   2160
cgcgtcgtct cgaacaggag gcggcaggtt tggcgaagtc gatgaccatc gacacgcgag   2220
gaactatgac gaccaagaag cgaaaaaccg ccggcgagga cctggcaaaa caggtcagcg   2280
aggccaagca ggccgcgttg ctgaaacaca cgaagcagca gatcaaggaa atgcagcttt   2340
ccttgttcga tattgcgccg tggccggaca cgatgcgagc gatgccaaac gacacggccc   2400
gctctgccct gttcaccacg cgcaacaaga aaatcccgcg cgaggcgctg caaaacaagg   2460
tcattttcca cgtcaacaag gacgtgaaga tcacctacac cggcgtcgag ctgcgggccg   2520
acgatgacga actggtgtgg cagcaggtgt tggagtacgc gaagcgcacc cctatcggcg   2580
agccgatcac cttcacgttc tacgagcttt gccaggacct gggctggtcg atcaatggcc   2640
ggtattacac gaaggccgag gaatgcctgt cgcgcctaca ggcgacggcg atgggcttca   2700
cgtccgaccg cgttgggcac ctggaatcgg tgtcgctgct gcaccgcttc cgcgtcctgg   2760
accgtggcaa gaaaacgtcc cgttgccagg tcctgatcga cgaggaaatc gtcgtgctgt   2820
ttgctggcga ccactacacg aaattcatat gggagaagta ccgcaagctg tcgccgacgg   2880
cccgacggat gttcgactat ttcagctcgc accgggagcc gtacccgctc aagctggaaa   2940
ccttccgcct catgtgcgga tcggattcca cccgcgtgaa gaagtggcgc gagcaggtcg   3000
gcgaagcctg cgaagagttg cgaggcagcg gcctggtgga acacgcctgg gtcaatgatg   3060
acctggtgca ttgcaaacgc tagggccttg tggggtcagt tccggctggg ggttcagcca   3120
gcgctttact gagatctcct gtggttggca tgcacataca aatggacgaa cggataaacc   3180
ttttcacgcc cttttaaata tccgattatt ctaataaacg ctcttttctc ttaggtttac   3240
ccgccaatat atcctgtcaa acactgatag tttaaactga aggcgggaaa cgacaatctg   3300
agctcgcatg cctgcaggtc aacatggtgg agcacgacac gcttgtctac tccaaaaata   3360
tcaaagatac agtctcagaa gaccaaaggg caattgagac ttttcaacaa agggtaatat   3420
ccggaaacct cctcggattc cattgcccag ctatctgtca ctttattgtg aagatagtgg   3480
aaaaggaagg tggctcctac aaatgccatc attgcgataa aggaaaggcc atcgttgaag   3540
atgcctctgc cgacagtggt cccaaagatg gacccccacc cacgaggagc atcgtggaaa   3600
aagaagacgt tccaaccacg tcttcaaagc aagtggattg atgtgataaa tggtggagca   3660
cgacacgctt gtctactcca aaaatatcaa agatacagtc tcagaagacc aaagggcaat   3720
tgagactttt caacaaaggg taatatccgg aaacctcctc ggattccatt gcccagctat   3780
ctgtcacttt attgtgaaga tagtggaaaa ggaaggtggc tcctacaaat gccatcattg   3840
cgataaagga aaggccatcg ttgaagatgc ctctgccgac agtggtccca aagatggacc   3900
cccacccacg aggagcatcg tggaaaaaga agacgttcca accacgtctt caaagcaagt   3960
ggattgatgt gatatctcca ctgacgtaag ggatgacgca caatcccact atccttcgca   4020
agacccttcc tctatataag gaagttcatt tcatttggag agcatattct gttggctttc   4080
atctgtgctt gtgcttcggt tcaatcacac tctgaaagtt tcagttcccc ggaatttcgg   4140
ttttcttcat aagccttatt cctacaggat gtctagcctt gctatctctg cccttccctg   4200
ttcagtcgct caactgagcg ttggtcagcc tgttgccacg gttgccaggt catttttgat   4260
gacttccctt ccgtcccttc agacttaccc atcttcgtct gagttgactt cctttttatt   4320
ttgttttggt gctttccaaa aaataaaaat gtttttatct ttcctacgtt cggtgcacgt   4380
ctttgcgcct tttctgaaa tttccacgat tggttcatgc tatgaattca ttcggttggg    4440
```

-continued

```
aggtggtgct taccctctct ttttctgttc cttccaatgc ggacctttgt ccgtttcttt   4500
gggttttgtt aacggcgttt ttgctgtttt aaacatgtca tttcctttct taagcaacgc   4560
atctcttttg acgggcgtcg gaaaaaatgt tgttcaagag aaaataaaaa tttccaaatt   4620
tgagaagaaa cagaagaagc gcgtttttc gatagctcgc gctaccgcgc gtcatgtgcc    4680
ttcccgtcgc aatcctaagg agaagcgtgt tgtccatgta cagcatctcc ctagtggttc   4740
tttacgcttt tcccaaaaca aaaacaaaac agaactgctc atcttaaaag aggaagtcgg   4800
aattgtcgcg cgcgttaagt gttcggcaag cgtcgtgcgc cgtcgcgttt gtggcggtgt   4860
ggttaagtgc aaacccctaa tagccgtttc tccctctggc gtgaaattcc gttgtttcgc   4920
gccgtcttgc agcacgtccg cttgtttaaa gctcaaaatc atgcgccgtg ttgccgtcgg   4980
tgactgccga ggtgagaaga taatcgcggc acgacgtgcg gcgctgcaga agcaggcttt   5040
caacagccgc acaccgaaga aagtgcgaga gaaccccatt agcgtctccg gggtgaactt   5100
gggaaggtct gccgccgctc aggttattta tttcggcagt ttcacgcagc ccttcgcgtt   5160
gtatccgcgc caagagagcg cgatcgtaaa aacgcaacct ccaccggtca gtgtagtgaa   5220
ggtggagtgc gtagctgcgg aggtagctcc cgacaggggc gtggtcgaca agaaacctac   5280
gtctgttggc gttcccccgc agcgcggtgt gctttctttt ccgacggtgg ttcggaaccg   5340
cggcgacgtg ataatcacag ggtggtgca tgaagccctg aagaaaatta aagacgggct    5400
cttacgcttc cgcgtaggcg gtgacatgcg tttttcgaga tttttctcat cgaactacgg   5460
ctgcagattc gtcgcgagcg tgcgtacgaa cactacagtt tggctaaatt gcacgaaagc   5520
gagtggtgag aaattctcac tcgccgccgc gtgcacggcg gattacgtgg cgatgctgcg   5580
ttatgtgtgt ggcgggaaat ttcctctcgt cctcatgagt agagttattt acccggatgg   5640
gcgctgttac ttggcccata tgaggtattt gtgcgccttt tactgtcgcc cgtttagaga   5700
gtcggattat gccctcggaa tgtggcctac ggtggcgcgt ctcagggcat gcgttgagaa   5760
gaacttcggt gtcgaagctt gtggcatagc tcttcgtggc tattacacct ctcgcaatgt   5820
ttatcactgt gattatgact ctgcttatgt aaaatatttt agaaaccttt ccggccgcat   5880
tggcggtggt tcgttcgatc cgacatcttt aacctccgta ataacggtga agattagcgg   5940
tcttccaggt ggtcttccta aaaatatagc gtttggtgcc ttcctgtgcg atatacgtta   6000
cgtcgaaccg gtagactcgg gcggcattca atcgagcgtt aagacgaaac gtgaagatgc   6060
gcaccgaacc gtagaggaac gggcggccgg cggatccgtc gagcaaccgc gacaaaagag   6120
gatagatgag aaaggttgcg gcagagttcc tagtggaggt ttttcgcatc tcctggtcgg   6180
cagccttaac gaagttagga ggaaggtagc tgccggactt ctacgctttc gcgttggcgg   6240
tgatatggat tttcatcgct cgttctccac ccaagcgggc caccgcttgc tggtgtggcg   6300
ccgctcgagc cggagcgtgt gccttgaact ttactcacca tctaaaaact ttttgcgtta   6360
cgatgtcttg ccttgttctg gagactatgc agcgatgttt tctttcgcgg cgggcggccg   6420
tttcccttta gttttgatga ctagaattag atacccgaac gggttttgtt acttggctca   6480
ctgccggtac gcgtgcgcgt ttctcttaag gggttttgat ccgaagcgtt tcgacatcgg   6540
tgctttcccc accgcagcca agctcagaaa ccgtatggtt tcggagcttg gtgaaagaag   6600
tttaggtttg aacttgtacg gcgcatatac gtcacgcggc gtctttcact gcgattatga   6660
cgctaagttt ataaaggatt tgcgtcttat gtcagcagtt atagctggaa aggacggagt   6720
ggaagaggtg gtaccttctg acataactcc tgccatgaag cagaaaacga tcgaagccgt   6780
gtatgataga ttatatggcg gcactgactc gttgctgaaa ctgagcatcg agaaagactt   6840
```

-continued

```
aatcgatttc aaaaatgacg tgcagagttt gaagaaagat cggccgattg tcaaagtgcc   6900
cttttatatg tcggaagcaa cacagaattc gctgacgcgt ttctaccctc agttcgaact   6960
taagttttcg cactcctcgc attcagatca tcccgccgcc gccgcttcta gactgctgga   7020
aaatgaaacg ttagtgcgct tatgtggtaa tagcgtttca gatattggag gttgtcctct   7080
tttccatttg cattccaaga cgcaaagacg ggttcacgta tgtaggcctg tgttggatgg   7140
caaggatgcg cagcgtcgcg tggtgcgtga tttgcagtat tccaacgtgc gttggggaga   7200
cgatgataaa attttggaag ggccacgcaa tatcgacatt tgccactatc ctctgggcgc   7260
gtgtgaccac gaaagtagtg ctatgatgat ggtgcaggtg tatgacgcgt ccctttatga   7320
gatatgtggc gccatgatca agaagaaaag ccgcataacg tacttaacca tggtcacgcc   7380
cggcgagttt cttgacggac gcgaatgcgt ctatatggag tcgttagact gtgagattga   7440
ggttgatgtg cacgcggacg tcgtaatgta caaattcggt agttcttgct attcgcacaa   7500
gctttcaatc atcaaggaca tcatgaccac tccgtacttg acactaggtg gttttctatt   7560
cagcgtggag atgtatgagg tgcgtatggg cgtgaattac ttcaagatta cgaagtccga   7620
agtatcgcct agcattagct gcaccaagct cctgagatac cgaagagcta atagtgacgt   7680
ggttaaagtt aaacttccac gtttcgataa gaaacgtcgc atgtgtctgc ctgggtatga   7740
caccatatac ctagattcga agtttgtgag tcgcgttttc gattatgtcg tgtgtaattg   7800
ctctgccgtg aactcaaaaa ctttcgagtg ggtgtggagt ttcattaagt ctagtaagtc   7860
gagggtgatt attagcggta aaataattca caaggatgtg aatttggacc ttaagtacgt   7920
cgagagtttc gccgcggtta tgttggcctc tggcgtgcgc agcagactag cgtccgagta   7980
ccttgctaag aaccttagtc atttttcggg agattgctcc tttattgaag ccacgtcttt   8040
cgtgttgcgt gagaaaatca gaaacatgac tctgaatttt aacgaaagac ttttacagtt   8100
agtgaagcgc gttgcctttg cgaccttgga cgtgagtttt ctagatttag attcaactct   8160
tgaatcaata actgattttg ccgagtgtaa ggtagcgatt gaactcgacg agttgggttg   8220
cttgagagcg gaggccgaga atgaaaaaat caggaatctg gcgggagatt cgattgcggc   8280
taaactcgcg agcgagatag tggtcgatat tgactctaag ccttcaccga agcaggtggg   8340
taattcgtca tccgaaaacg ccgataagcg ggaagttcag aggcccggtt tgcgtggtgg   8400
ttctagaaac ggggttgttg gggagttcct tcacttcgtc gtggattctg ccttgcgtct   8460
tttcaaatac gcgacggatc aacaacggat caagtcttac gtgcgtttct tggactcggc   8520
ggtctcattc ttggattaca actacgataa tctatcgttt atactgcgag tgctttcgga   8580
aggttattcg tgtatgttcg cgtttttggc gaatcgcggc gacttatcta gtcgtgtccg   8640
tagcgcggtg cgtgctgtga aagaagttgc tacctcatgc gcgaacgcga gcgtttctaa   8700
agccaaggtt atgattacct tcgcagcggc cgtgtgtgct atgatgttta atagctgcgg   8760
tttttcaggc gacggtcggg agtataaatc gtatatacat cgttacacgc aagtattgtt   8820
tgacactatc ttttttgagg acagcagtta cctacccata gaagttctga gttcggcgat   8880
atgcggtgct atcgtcacac ttttctcctc gggctcgtcc ataagtttaa acgccttctt   8940
acttcaaatt accaaaggat tctccctaga ggttgtcgtc cggaatgttg tgcgagtcac   9000
gcatggtttg agcaccacag cgaccgacgg cgtcatacgt ggggttttct cccaaattgt   9060
gtctcactta cttgttggaa ataccggtaa tgtggcttac cagtcagctt tcattgccgg   9120
ggtggtgcct cttttagtta aaaagtgtgt gagcttaatc ttcatcttgc gtgaagatac   9180
ttattccggt tttattaagc acggaatcag tgaattctct ttccttagta gtattctgaa   9240
```

-continued

```
gttcttgaag ggtaagcttg tggacgagtt gaaatcgatt attcaagggg tttttgattc   9300
caacaagcac gtgtttaaag aagctactca ggaagcgatt cgtacgacgg tcatgcaagt   9360
gcctgtcgct gtagtggatg cccttaagag cgccgcggga aaaatttata acaattttac   9420
tagtcgacgt acctttggta aggatgaagg ctcctctagc gacggcgcat gtgaagagta   9480
tttctcatgc gacgaaggtg aaggtccggg tctgaaaggg ggttccagct atggcttctc   9540
aattttagcg ttcttttcac gcattatgtg gggagctcgt cggcttattg ttaaagtgaa   9600
gcatgagtgt tttgggaaac tttttgaatt tctatcgctc aagcttcacg aattcaggac   9660
tcgcgttttt gggatgaata gaacggacgt gggagtttac gatttttttgc ccacggacat   9720
cgtggaaacg ctctcatcga tagaagagtg cgaccaaatt gaagaacttc tcggcgacga   9780
cctgaaaggt gacaaggatg cttcgttgac cgatatgaat tactttgagt tctcagaaga   9840
cttcttagcc tctgtcgagg agccgccttt cgctggattg cgaggaggta gcaagaacgt   9900
cgcgattttg gcgattttgg aatacgcgca taatttgttt cgcattgtcg caagcaagtg   9960
ttcgaaacga cctttatttc ttgctttcgc cgaactctca agcgcccctta tcgagaaatt  10020
taaggaggtt ttccctcgta agagccagct cgtcgctatc gtgcgcgagt atactcagag  10080
attcctccga agtcgcatgc gtgcgttggg tttgaataac gagttcgtgg taaaatcttt  10140
cgccgatttg ctacccgcat taatgaagcg gaaggtttca ggttcgttct tagctagtgt  10200
ttatcgccca cttagaggtt tctcatatat gtgtgtttca gcggagcgac gtgaaaagtt  10260
ttttgctctc gtgtgtttaa tcgggttaag tctccctttc ttcgtgcgca tcgtaggagc  10320
gaaagcgtgc gaagaactcg tgtcctcagc gcgtcgcttt tatgagcgta ttaaaatttt  10380
tctcaggcag aagtatgtct ctctttctaa tttcttttgt cacttgttta gctctgacgt  10440
tgatgacagt tccgcatcag cagggttgaa aggtggtgcg tcgcgaatga cgctcttcca  10500
ccttctggtt cgccttgcta gtgccctcct atcgttaggg tgggaagggt taaagctact  10560
cttatcgcac cacaacttgt tatttttgtg ttttgcattg gttgacgatg tgaacgtctt  10620
atcaaagttc ttgggggtct ttctttcttt gtgcaaccag tcttttcctt gtttgcggcg  10680
atgcttttac aaccggacag gtttgtgggg tattccgaga aacttgttac agcgtttgaa  10740
tttttcttaa aatgttcgcc tcgcgcgcct gcactactca aagggttttt tgagtgcgtg  10800
gcgaacagca ctgtgtcaaa aaccgttcga agacttcttc gctatttcgt gaggatgctc  10860
aaacttcgaa aagggcgagg gttgcgtgcg gatggtaggg gtctccatcg gcagaaagcc  10920
gtacccgtca taccttctaa tcgggtcgtg accgacgggg ttgaaagact ttcggtaaag  10980
atgcaaggag ttgaagcgtt gcgtaccgaa ttgagaatct tagaagattt agattctgcc  11040
gtgatcgaaa aactcaatag acgcagaaat cgtgacacta atgacgacga atttacgcgc  11100
cctgctcatg agcagatgca agaagtcacc actttctgtt cgaaagccaa ctctgctggt  11160
ttggccctgg aaagggcagt gcttgtggaa gacgctataa agtcggagaa actttctaag  11220
acggttaatg agatggtgag gaaagggagt accaccagcg aagaagtggc cgtcgctttg  11280
tcggacgatg aagccgtgga agaaatctct gttgctgacg agcgagacga ttcgcctaag  11340
acagtcagga taagcgaata cctaaatagg ttaaactcaa gcttcgaatt cccgaagcct  11400
attgttgtgg acgacaacaa ggataccggg ggtctaacga acgccgtgag ggagttttat  11460
tatatgcaag aacttgctct tttcgaaatc cacagcaaac tgtgcgccta ctacgatcaa  11520
ctgcgcatag tcaacttcga tcgttccgta gcaccatgca gcgaagatgc tcagctgtac  11580
gtacggaaga gcggctcaac gatagtgcag ggtaaagagg tacgtttgca cattaaggat  11640
```

-continued ttccacgatc acgatttcct gtttgacggg aaaatttcta ttaacaagcg gcggcgaggc 11700
ggaaacgttt tatatcacga caacctcgcg ttcttggcga gtaatttgtt cttagccggc 11760
taccccttttt caaggagctt cgtcttcacg aattcgtcgg tcgatattct cctctacgaa 11820
gctccacccg gaggtggtaa gacgacgacg ctgattgact cgttcttgaa ggtcttcaag 11880
aaaggtgagg tttccaccat gatcttaacc gccaacaaaa gttcgcaggt tgagatccta 11940
aagaaagtgg agaaggaagt gtctaacatt gaatgccaga aacgtaaaga caagagatct 12000
ccgaaaaaga gcatttacac catcgacgct tatttaatgc atcaccgtgg ttgtgatgca 12060
gacgttcttt tcatcgatga gtgtttcatg gttcatgcgg gtagcgtact agcttgcatt 12120
gagttcacga ggtgtcataa agtaatgatc ttcggggata gccggcagat tcactacatt 12180
gaaaggaacg aattggacaa gtgtttgtat ggggatctcg ataggttcgt ggacctgcag 12240
tgtcgggttt atggtaatat ttcgtaccgt tgtccatggg atgtgtgcgc ttggttaagc 12300
acagtgtatg gcaacctaat cgccaccgtg aagggtgaaa gcgaaggtaa gagcagcatg 12360
cgcattaacg aaattaattc agtcgacgat ttagtccccg acgtgggttc cacgtttctg 12420
tgtatgcttc agtcggagaa gttggaaatc agcaagcact ttattcgcaa gggtttgcct 12480
aaacttaacg ttctaactgt gcatgaggcg caaggtgaga cgtatgcgcg tgtgaacctt 12540
gtgcgactta agtttcagga ggatgaaccc tttaaatcta tcaggcacat aaccgtcgct 12600
ctttctcgtc acaccgacag cttaacttat aacgtcttag ctgctcgtcg aggtgacgcc 12660
acttgcgatg ccatccagaa ggctgcggaa ttggtgaaca agtttcgcgt tttcctaca 12720
tcttttggtg gtagtgttat caatctcaac gtgaaaaagg acgtggaaga taacagtagg 12780
tgcaaggctt cgtcggcacc attgagcgta atcaacgact tttgaacgaa agttaatccc 12840
ggtactgcgg tgattgattt tggtgatttg tccgcggact tcagtactgg gccttttgag 12900
tgcggtgcca gcggtattgt ggtgcgggac aacatctcct ccagcaacat cactgatcac 12960
gataagcagc gtgtttagcg tagttcggtc gcaggcgatt ccgcgtagaa aaccttctct 13020
acaagaaaat ttgtattcgt ttgaagcgcg gaattataac ttctcgactt gcgaccgtta 13080
cacatctgct tcaatgttcg gagaggctat ggcgatgaac tgtcttcgtc gttgcttcga 13140
cctagatgcc ttttcgtccc tgcgtaatga tgtgattagt atcacacgtt caggcatcga 13200
acaatggctg gagaaacgta ctcctagtca gattaaagca ttaatgaagg atgttgaatc 13260
gcctttggaa attgacgatg aaatttgtcg ttttaagttg atggtgaagc gtgacgctaa 13320
ggtgaagtta gactcttctt gtttaactaa acacagcgcc gctcaaaata tcatgtttca 13380
tcgcaagagc attaatgcta tcttctctcc tatctttaac gaggtgaaaa accgaataat 13440
gtgctgtctt aagcctaaca taaagttttt tacggagatg actaacaggg attttgcttc 13500
tgttgtcagc aacatgcttg gtgacgacga tgtgtaccat ataggtgaag ttgatttctc 13560
aaagtacgac aagtctcaag atgctttcgt gaaggctttt gaagaagtga tgtataagga 13620
actcggtgtt gatgaagagt tgctggctat ctggatgtgc ggcgagcggt tatcgatagc 13680
taacactctc gatggtcagt tgtccttcac gatcgagaat caaaggaagt cgggagcttc 13740
gaacacttgg attggtaact ctctcgtcac tttgggtatt ttaagtcttt actacgacgt 13800
tagaaatttc gaggcgttgt acatctcggg cgatgattct ttaatttttt ctcgcagcga 13860
gatttcgaat tatgccgacg acatatgcac tgacatgggt tttgagacaa aatttatgtc 13920
cccaagtgtc ccgtactttt gttctaaatt tgttgttatg tgtggtcata agacgttttt 13980
tgttcccgac ccgtacaagc tttttgtcaa gttgggagca gtcaaagagg atgtttcaat 14040

-continued

```
ggatttcctt ttcgaaactt ttacctcctt taaagactta acctccgatt ttaacgacga  14100
gcgcttaatt caaaagctcg ctgaacttgt ggctttaaaa tatgaggttc aaaccggcaa  14160
caccaccttg gcgttaagtg tgatacattg tttgcgttcg aatttcctct cgtttagcaa  14220
gttgtatcct cgcgtgaagg gatggcaggt tttttacacg tcggttaaga aagcgcttct  14280
caagagtggg tgttctctct tcgacagttt catgacccct tttggtcagg ctgtcatggt  14340
ttgggatgat gagtagcgct aacttgtgcg cagtttcttt gttcgtgaca tacaccttgt  14400
gtgtcaccgt gcgtttataa tgaatcaggt tttgcagttt gaatgtttat ttctgctgaa  14460
tctcgcggtt tttgctgtga ctttcatttt cattcttctg gtcttccgcg tgattaagtc  14520
ttttcgccag aagggtcacg aagcgcctgt tcccgttgtt cgtggcgggg gtttttcaac  14580
cgtagtgtag tcaaaagacg cgcatatggt agttttcggt ttggactttg gcaccacatt  14640
ctctacggtg tgtgtgtaca aggatggacg agttttttca ttcaagcaga ataattcggc  14700
gtacatcccc acttacctct atctcttctc cgattctaac cacatgactt ttggttacga  14760
ggccgaatca ctgatgagta atctgaaagt taaaggttcg ttttatagag atttaaaacg  14820
ttgggtgggt tgcgattcga gtaacctcga cgcgtacctt gaccgtttaa aacctcatta  14880
ctcggtccgc ttggttaaga tcggctctgg cttgaacgaa actgtttcaa ttggaaactt  14940
tgggggcact gttaagtctg aggctcatct gccagggttg atagctctct ttattaaggc  15000
tgtcattagt tgcgcggagg gcgcgtttgc gtgcacttgc accggggtta tttgttcagt  15060
acctgccaat tatgatagcg ttcaaaggaa tttcactgat cagtgtgttt cactcagcgg  15120
ttatcaatgc gtatatatga tcaatgaacc ttcagcggct gcgctatctg cgtgtaattc  15180
ggttggaaag aagtccgcaa atttggctgt ttacgatttc ggtggtggga ccttcgacgt  15240
gtctatcatt tcataccgca acaatacttt tgttgtgcga gcttctggag gcgatctaaa  15300
tctcggtgga agggatgttg atcgtgcgtt tctcacgcac ctcttctctt taacatcgct  15360
ggaacctgac ctcactttgg atatctcgaa tctgaaagaa tctttatcaa aaacggacgc  15420
agagatagtt tacactttga gaggtgtcga tggaagaaaa gaagacgtta gagtaaacaa  15480
aaacattctt acgtcggtga tgctccccta cgtgaacaga acgcttaaga tattagagtc  15540
aaccttaaaa acgtatgcta agagtatgaa tgagagtgcg cgagttaagt gcgatttagt  15600
gctgatagga ggatcttcat atcttcctgg cctggcagac gtactaacga agcatcagag  15660
cgttgatcgt atcttaagag tttcggatcc tcgggctgcc gtggccgtcg gttgcgcact  15720
atattcttca tgcctctcag gatctggggg gttgctactg atcgactgtg cagctcacac  15780
tgtcgctata gcggacagaa gttgtcagca aatcatttgc gctccagcgg gggcaccgat  15840
ccccttttca ggaagcatgc ctttgtactt agccagggtc aacaagaact cgcagcgtga  15900
aatcgccgtg tttgaagggg agtacgttaa gtgccctaag aacagaaaga tctgtggagc  15960
aaatataaga tttttttgata taggagtgac gggtgattcg tacgcacccg ttaccttcta  16020
tatggatttc tccatttcaa gcgtaggagc cgtttcattc gtggtgagag gtcctgaggg  16080
taagcaagtg tcactcactg gaactccagc gtataacttt tcgtctgtgg ctctcggatc  16140
acgcagtgtc cgagaattgc atattagttt aaataataaa gtttttctcg gtttgcttct  16200
acatagaaag gcggatcgac gaatactttt cactaaggat gaagcgattc gatacgccga  16260
ttcaattgat atcgcggatg tgctaaagga atataaaagt tacgcggcca gtgccttacc  16320
accagacgag gatgtcgaat tactcctggg aaagtctgtt caaaaagttt tacggggaag  16380
cagactggaa gaaatacctc tctaggagca tagcagcaca ctcaagtgaa attaaaactc  16440
```

```
taccagacat tcgattgtac ggcggtaggg ttgtaaagaa gtccgatttc gaatcagcac  16500
ttcctaattc ttttgaacag gaattaggac tgttcatact gagcgaacgg gaagtgggat  16560
ggagcaaatt atgcggaata acggtggaag aagcagcata cgatcttacg aatcccaagg  16620
cttataaatt cactgccgag acatgtagcc cggatgtaaa aggtgaagga caaaaatact  16680
ctatggaaga cgtgatgaat ttcatgcgtt tatcaaatct ggatgttaac gacaagatgc  16740
tggcggaaca gtgttggtcg ctgtccaatt catgcggtga attgatcaac ccagacgaca  16800
aagggcgatt cgtggctctc acctttaagg acagagacac agctgatgac acgggtgccg  16860
ccaacgtgga atgtcgcgtg ggcgactatc tagtttacgc tatgtccctg tttgagcaga  16920
ggacccaaaa atcgcagtct ggcaacatct ctctgtacga aaagtactgc gaatacatca  16980
ggacctactt agggagtaca gacctgtttt tcacagcgcc ggacaggatt ccgttactta  17040
cgggcatcct atacgatttt tgtaaggaat acaacatttt ctactcgtca tataagagaa  17100
acgtcgataa tttcagattc ttcttggcga attatatgcc tttgatatct gacgtctttg  17160
tcttccagtg ggtaaaaccc gcgccggatg ttcggctgct tttgagttta agtgcagcgg  17220
aactaacgct ggaggttccc acactgagtt tgatagattc tcaagttgtg gtaggtcata  17280
tcttaagata cgtagaatcc tacacatcag atccagccat cgacgcgtta gaagacaaac  17340
tggaagcgat actgaaaagt agcaatcccc gtctatcgac agcgcaacta tgggttggtt  17400
tcttttgtta ctatggtgag tttcgtacgg ctcaaagtag agtagtgcaa agaccaggcg  17460
tatacaaaac acctgactca gtgggtggat ttgaaataaa catgaaagat gttgagaaat  17520
tcttcgataa acttcagaga gaattgccta atgtatcttt gcggcgtcag tttaacggag  17580
ctagagcgca tgaggctttc aaaatattta aaaacggaaa tataagtttc aaacctatat  17640
cgcgtttaaa cgtgcctaga gagttctggt atctgaacat agactacttc aggcacgcga  17700
ataggtccgg gttaaccgaa gaagaaatac tcatcctaaa caacataagc gttgatgtta  17760
ggaagttatg cgctgagaga gcgtgcaata ccctacctag cgcgaagcgc tttagtaaaa  17820
atcataagag taatatacaa tcatcacgcc aagagcggag gattaaagac ccattggtag  17880
tcctgaaaga cactttatat gagttccaac gcaagcgtgc cggttggggg tctcgaagca  17940
ctcgagacct cgggagtcgt gctgaccacg cgaaaggaag cggttgataa gttttttaat  18000
gaactaaaaa acgaaaatta ctcatcagtt gacagcagcc gattaagcga ttcggaagta  18060
aaagaagtgt tagagaaaag taaagaaagt ttcaaaagcg aactggcctc cactgacgag  18120
cacttcgtct accacattat atttttctta atccgatgtg ctaagatatc gacgagtgaa  18180
aaagtgaagt acgttggtag tcatacgtac gtggtcgacg gaaaaacgta caccgttctt  18240
gacgcttggg tattcaacat gatgaaaagt ctcacgaaga agtacaaacg agtgaatggt  18300
ctgcgtgcgt tctgttgcgc gtgcgaagat ctatatctaa ccgtcgcacc aataatgtca  18360
gaacgcttta agactaaagc cgtagggatg aaaggtttgc ctgttggaaa ggaatactta  18420
ggcgccgact ttctttcggg aactagcaaa ctgatgagcg atcacgacag ggcggtctcc  18480
atcgttgcag cgaaaaacgc tgtcgatcgt agcgctttca cgggtgggga gagaaagata  18540
gttagtttgt atgatctagg gaggtactaa gcacggtgtg ctatagtgcg tgctataata  18600
ataaacacta gtgcttaagt cgcgcagaag aaaacgctta attaacaatg aagactaatc  18660
tttttctctt tctcatcttt tcacttctcc tatcattatc ctcggccgaa ttcagtaaag  18720
gagaagaact tttcactgga gttgtcccaa ttcttgttga attagatggt gatgttaatg  18780
ggcacaaatt ttctgtcagt ggagagggtg aaggtgatgc aacatacgga aaacttaccc  18840
```

-continued

```
ttaaatttat ttgcactact ggaaaactac ctgttccatg gccaacactt gtcactactt  18900
tctcttatgg tgttcaatgc ttttcaagat acccagatca tatgaagcgg cacgacttct  18960
tcaagagcgc catgcctgag ggatacgtgc aggagaggac catcttcttc aaggacgacg  19020
ggaactacaa gacacgtgct gaagtcaagt ttgagggaga caccctcgtc aacaggatcg  19080
agcttaaggg aatcgatttc aaggaggacg gaaacatcct cggccacaag ttggaataca  19140
actacaactc ccacaacgta tacatcatgg ccgacaagca aaagaacggc atcaaagcca  19200
acttcaagac ccgccacaac atcgaagacg gcggcgtgca actcgctgat cattatcaac  19260
aaaatactcc aattggcgat ggccctgtcc ttttaccaga caaccattac ctgtccacac  19320
aatctgccct ttcgaaagat cccaacgaaa agagagacca catggtcctt cttgagtttg  19380
taacagctgc tgggattaca catggcatgg atgaactata caaacatgat gagctttagt  19440
aaactgttcc tgaatagaac cattggcaaa cgtgggatcc cgtcagggta tgagttcctc  19500
ggggcagatt ttctaactgc gaccagcgtg tgtttgaacg atcacgaaaa agctatcgta  19560
ctacaggcct caagagctgc cattgataga gcagtctctt cgtcggtcga cgggaagatc  19620
gtcagtcttt tcgacctcgg tcgtcttagt taacacagtt actaaggttc cattttatta  19680
ttgcattgtt tttcatttag tgtaatcgta cttgagttct aatcctgcag gctatggagt  19740
tgatgtccga cagcaacctt agcaacctgg tgataaccga cgcctctagt ctaaatggtg  19800
tcgacaagaa gcttttatct gctgaagttg taaaaatgct ggtgcagaaa ggggctccta  19860
acgagggtat agaagtggtg ttcggtctac tcctttacgc actcgcggca agaaccacgt  19920
ctcctaaggt tcagcgcgca gattcagacg ttatattttc aaatagtttc ggagagagga  19980
atgtggtagt aacagagggt gaccttaaga aggtactcga cgggtgtgcg cctctcacta  20040
ggttcactaa taaacttaga acgttcggtc gtactttcac tgaggcttac gttgactttt  20100
gtatcgcgta taagcacaaa ttaccccaac tcaacgccgc ggcggaattg gggattccag  20160
ctgaagattc gtacttagct gcagattttc tgggtacttg cccgaagctc tctgaattac  20220
agcaaagtag gaagatgttc gcgagtatgt acgctctaaa aactgaaggt ggagtggtaa  20280
atacaccagt gagcaatctg cgtcagctag gtagaaggga agttatgtaa tggaagatta  20340
cgaagaaaaa tccgaatcgc tcatactgct acgcacgaat ctgaacacta tgcttttagt  20400
ggtcaagtcc gatgctagtg tagagctgcc taaactacta atttgcggtt acttacgagt  20460
gtcaggacgt ggggaggtga cgtgttgcaa ccgtgaggaa ttaacaagag attttgaggg  20520
caatcatcat acggtgatcc gttctagaat catacaatat gacagcgagt ctgcttttga  20580
ggaattcaac aactctgatt gcgtagtgaa gtttttccta gagactggta gtgtcttttg  20640
gtttttcctt cgaagtgaaa ccaaaggtag agcggtgcga catttgcgca ccttcttcga  20700
agctaacaat ttcttctttg gatcgcattg cggtaccatg gagtattgtt tgaagcaggt  20760
actatctgaa actgaatcta taatcgattc tttttgcgaa gaaagaaatc gttaagatga  20820
gggttatagt gtctccttat gaagctgaag acattctgaa aagatcgact gacatgttac  20880
gaaacataga cagtggggtc ttgagcacta aagaatgtat caaggcattc tcgacgataa  20940
cgcgagacct acattgtgcg aaggcttcct accagtgggg tgttgacact gggttatatc  21000
agcgtaattg cgctgaaaaa catttaattg acacggtgga gtcaaacata cggttggctc  21060
aacctctcgt gcgtgaaaaa gtggcggttc atttttgtaa ggatgaacca aaagagctag  21120
tagcattcat cacgcgaaag tacgtggaac tcacgggcgt gggagtgaga gaagcggtga  21180
agagggaaat gcgctctctt accaaaacag ttttaaataa aatgtctttg gaaatggcgt  21240
```

```
tttacatgtc accacgagcg tggaaaaacg ctgaatggtt agaactaaaa ttttcacctg  21300
tgaaaatctt tagagatctt ttattagacg tggaaacgct caacgaattg tgcgccgaag  21360
atgatgttca cgtcgacaaa gtaaatgaga atggggacga aaatcacgac ctcgaactcc  21420
aagacgaatg ttaaacattg gttaagttta acgaaaatga ttagtaaata ataaatcgaa  21480
cgtgggtgta tctacctgac gtatcaactt aagctgttac tgagtaatta aaccaacaag  21540
tgttggtgta atgtgtatgt tgatgtagag aaaaatccgt ttgtagaacg gtgtttttct  21600
cttctttatt tttaaaaaaa aataaaaaaa aaaaaaaaga agctcaagac atgattcaca  21660
tgtcttctga tgagtccgtg aggacgaaag cttcttttcc cggggatcgt tcaaacattt  21720
ggcaataaag tttcttaaga ttgaatcctg ttgccggtct tgcgatgatt atcatataat  21780
ttctgttgaa ttacgttaag catgtaataa ttaacatgta atgcatgacg ttatttatga  21840
gatgggtttt tatgattaga gtcccgcaat tatacattta atacgcgata gaaaacagaa  21900
tatagcgcgc aaactaggat aaattatcgc gcgcggtgtc atctatgtta ctagatcaag  21960
cttatcgata ccgtcgacct cgaggggggg cccggtacca aaaccacccc agtacattaa  22020
aaacgtccgc aatgtgttat taagttgtct aagcgtcaat ttgtttacac cacaatatat  22080
cctgccacca gccagccaac agctccccga ccggcagctc ggcacaaaat caccactcga  22140
tacaggcagc ccatcagtcc actaga                                        22166
```

<210> SEQ ID NO 2
<211> LENGTH: 14508
<212> TYPE: DNA
<213> ORGANISM: Artificial sequence
<220> FEATURE:
<223> OTHER INFORMATION: Engineered viral vector

<400> SEQUENCE: 2

```
atattctgtt ggctttcatc tgtgcttgtg cttcggttca atcacactct gaaagtttca     60
gttccccgga atttcggttt tcttcataag ccttattcct acaggatgtc tagccttgct    120
atctctgccc ttccctgttc agtcgctcaa ctgagcgttg gtcagcctgt tgccacggtt    180
gccaggtcat ttttgatgac ttcccttccg tcccttcaga cttacccatc ttcgtctgag    240
ttgacttcct ttttattttg ttttggtgct ttccaaaaaa taaaaatgtt tttatctttc    300
ctacgttcgg tgcacgtctt tgcgcctttt tctgaaattt ccacgattgg ttcatgctat    360
gaattcattc ggttgggagg tggtgcttac cctctctttt tctgttcctt ccaatgcgga    420
cctttgtccg tttctttggg ttttgttaac ggcgtttttg ctgttttaaa catgtcattt    480
cctttcttaa gcaacgcatc tcttttgacg ggcgtcggaa aaaatgttgt tcaagagaaa    540
ataaaaattt ccaaatttga gaagaaacag aagaagcgcg tttttttcgat agctcgcgct    600
accgcgcgtc atgtgccttc ccgtcgcaat cctaaggaga agcgtgttgt ccatgtacag    660
catctcccta gtggttcttt acgcttttcc caaaacaaaa acaaaaacaga actgctcatc    720
ttaaaagagg aagtcggaat tgtcgcgcgc gttaagtgtt cggcaagcgt cgtgcgccgt    780
cgcgtttgtg gcggtgtggt taagtgcaaa cccctaatag ccgtttctcc ctctggcgtg    840
aaattccgtt gtttcgcgcc gtcttgcagc acgtccgctt gtttaaagct caaaatcatg    900
cgccgtgttg ccgtcggtga ctgccgaggt gagaagataa tcgcggcacg acgtgcggcg    960
ctgcagaagc aggctttcaa cagccgcaca ccgaagaaag tgcgagagaa ccccattagc   1020
gtctccgggg tgaacttggg aaggtctgcc gccgctcagg ttatttattt cggcagtttc   1080
acgcagccct tcgcgttgta tccgcgccaa gagagcgcga tcgtaaaaac gcaacctcca   1140
```

-continued ccggtcagtg tagtgaaggt ggagtgcgta gctgcggagg tagctcccga caggggcgtg 1200
gtcgacaaga aacctacgtc tgttggcgtt cccccgcagc gcggtgtgct ttcttttccg 1260
acggtggttc ggaaccgcgg cgacgtgata atcacagggg tggtgcatga agccctgaag 1320
aaaattaaag acgggctctt acgcttccgc gtaggcggtg acatgcgttt ttcgagattt 1380
ttctcatcga actacggctg cagattcgtc gcgagcgtgc gtacgaacac tacagtttgg 1440
ctaaattgca cgaaagcgag tggtgagaaa ttctcactcg ccgccgcgtg cacggcggat 1500
tacgtggcga tgctgcgtta tgtgtgtggc gggaaatttc ctctcgtcct catgagtaga 1560
gttatttacc cggatgggcg ctgttacttg gcccatatga ggtatttgtg cgccttttac 1620
tgtcgcccgt ttagagagtc ggattatgcc ctcggaatgt ggcctacggt ggcgcgtctc 1680
agggcatgcg ttgagaagaa cttcggtgtc gaagcttgtg gcatagctct tcgtggctat 1740
tacacctctc gcaatgttta tcactgtgat tatgactctg cttatgtaaa atattttaga 1800
aacctttccg gccgcattgg cggtggttcg ttcgatccga catctttaac ctccgtaata 1860
acggtgaaga ttagcggtct tccaggtggt cttcctaaaa atatagcgtt tggtgccttc 1920
ctgtgcgata tacgttacgt cgaaccggta gactcgggcg gcattcaatc gagcgttaag 1980
acgaaacgtg aagatgcgca ccgaaccgta gaggaacggg cggccggcgg atccgtcgag 2040
caaccgcgac aaaagaggat agatgagaaa ggttgcggca gagttcctag tggaggtttt 2100
tcgcatctcc tggtcggcag ccttaacgaa gttaggagga aggtagctgc cggacttcta 2160
cgctttcgcg ttggcggtga tatggatttt catcgctcgt tctccaccca agcgggccac 2220
cgcttgctgg tgtggcgccg ctcgagccgg agcgtgtgcc ttgaacttta ctcaccatct 2280
aaaaactttt tgcgttacga tgtcttgcct tgttctggag actatgcagc gatgttttct 2340
ttcgcggcgg gcggccgttt ccctttagtt ttgatgacta gaattagata cccgaacggg 2400
ttttgttact tggctcactg ccggtacgcg tgcgcgtttc tcttaagggg ttttgatccg 2460
aagcgtttcg acatcggtgc tttccccacc gcagccaagc tcagaaaccg tatggtttcg 2520
gagcttggtg aaagaagttt aggtttgaac ttgtacggcg catatacgtc acgcggcgtc 2580
tttcactgcg attatgacgc taagtttata aaggatttgc gtcttatgtc agcagttata 2640
gctggaaagg acggagtgga agaggtggta ccttctgaca taactcctgc catgaagcag 2700
aaaacgatcg aagccgtgta tgatagatta tatggcggca ctgactcgtt gctgaaactg 2760
agcatcgaga aagacttaat cgatttcaaa aatgacgtgc agagtttgaa gaaagatcgg 2820
ccgattgtca aagtgccctt ttatatgtcg gaagcaacac agaattcgct gacgcgtttc 2880
taccctcagt tcgaacttaa gttttcgcac tcctcgcatt cagatcatcc cgccgccgcc 2940
gcttctagac tgctggaaaa tgaaacgtta gtgcgcttat gtggtaatag cgtttcagat 3000
attggaggtt gtcctctttt ccatttgcat tccaagacgc aaagacgggt tcacgtatgt 3060
aggcctgtgt tggatggcaa ggatgcgcag cgtcgcgtgg tgcgtgattt gcagtattcc 3120
aacgtgcgtt ggggagacga tgataaaatt ttggaagggc cacgcaatat cgacatttgc 3180
cactatcctc tgggcgcgtg tgaccacgaa agtagtgcta tgatgatggt gcaggtgtat 3240
gacgcgtccc tttatgagat atgtggcgcc atgatcaaga agaaaagccg cataacgtac 3300
ttaaccatgg tcacgcccgg cgagtttctt gacggacgcg aatgcgtcta tatggagtcg 3360
ttagactgtg agattgaggt tgatgtgcac gcggacgtcg taatgtacaa attcggtagt 3420
tcttgctatt cgcacaagct ttcaatcatc aaggacatca tgaccactcc gtacttgaca 3480
ctaggtggtt ttctattcag cgtggagatg tatgaggtgc gtatgggcgt gaattacttc 3540

-continued

```
aagattacga agtccgaagt atcgcctagc attagctgca ccaagctcct gagataccga   3600
agagctaata gtgacgtggt taaagttaaa cttccacgtt tcgataagaa acgtcgcatg   3660
tgtctgcctg ggtatgacac catataccta gattcgaagt ttgtgagtcg cgttttcgat   3720
tatgtcgtgt gtaattgctc tgccgtgaac tcaaaaactt tcgagtgggt gtggagtttc   3780
attaagtcta gtaagtcgag ggtgattatt agcggtaaaa taattcacaa ggatgtgaat   3840
ttggacctta agtacgtcga gagtttcgcc gcggttatgt tggcctctgg cgtgcgcagc   3900
agactagcgt ccgagtacct tgctaagaac cttagtcatt tttcgggaga ttgctccttt   3960
attgaagcca cgtctttcgt gttgcgtgag aaaatcagaa acatgactct gaattttaac   4020
gaaagacttt tacagttagt gaagcgcgtt gcctttgcga ccttggacgt gagttttcta   4080
gatttagatt caactcttga atcaataact gattttgccg agtgtaaggt agcgattgaa   4140
ctcgacgagt tgggttgctt gagagcggag gccgagaatg aaaaaatcag gaatctggcg   4200
ggagattcga ttgcggctaa actcgcgagc gagatagtgg tcgatattga ctctaagcct   4260
tcaccgaagc aggtgggtaa ttcgtcatcc gaaaacgccg ataagcggga agttcagagg   4320
cccggtttgc gtggtggttc tagaaacggg gttgttgggg agttccttca cttcgtcgtg   4380
gattctgcct tgcgtctttt caaatacgcg acggatcaac aacggatcaa gtcttacgtg   4440
cgtttcttgg actcggcggt ctcattcttg gattacaact acgataatct atcgtttata   4500
ctgcgagtgc tttcggaagg ttattcgtgt atgttcgcgt tttggcgaa tcgcggcgac    4560
ttatctagtc gtgtccgtag cgcggtgcgt gctgtgaaag aagttgctac ctcatgcgcg   4620
aacgcgagcg tttctaaagc caaggttatg attaccttcg cagcggccgt gtgtgctatg   4680
atgtttaata gctgcggttt ttcaggcgac ggtcgggagt ataaatcgta tatacatcgt   4740
tacacgcaag tattgtttga cactatcttt tttgaggaca gcagttacct acccatagaa   4800
gttctgagtt cggcgatatg cggtgctatc gtcacacttt tctcctcggg ctcgtccata   4860
agtttaaacg ccttcttact tcaaattacc aaaggattct ccctagaggt tgtcgtccgg   4920
aatgttgtgc gagtcacgca tggtttgagc accacagcga ccgacggcgt catacgtggg   4980
gttttctccc aaattgtgtc tcacttactt gttggaaata ccggtaatgt ggcttaccag   5040
tcagctttca ttgccggggt ggtgcctctt ttagttaaaa agtgtgtgag cttaatcttc   5100
atcttgcgtg aagatactta ttccggtttt attaagcacg gaatcagtga attctctttc   5160
cttagtagta ttctgaagtt cttgaagggt aagcttgtgg acgagttgaa atcgattatt   5220
caaggggttt ttgattccaa caagcacgtg tttaaagaag ctactcagga agcgattcgt   5280
acgacggtca tgcaagtgcc tgtcgctgta gtggatgccc ttaagagcgc cgcgggaaaa   5340
atttataaca attttactag tcgacgtacc tttggtaagg atgaaggctc ctctagcgac   5400
ggcgcatgtg aagagtattt ctcatgcgac gaaggtgaag gtccgggtct gaaagggggt   5460
tccagctatg gcttctcaat tttagcgttc ttttcacgca ttatgtgggg agctcgtcgg   5520
cttattgtta aagtgaagca tgagtgtttt gggaaacttt ttgaatttct atcgctcaag   5580
cttcacgaat tcaggactcg cgtttttggg atgaatagaa cggacgtggg agtttacgat   5640
tttttgccca cggacatcgt ggaaacgctc tcatcgatag aagagtgcga ccaaattgaa   5700
gaacttctcg gcgacgacct gaaaggtgac aaggatgctt cgttgaccga tatgaattac   5760
tttgagttct cagaagactt cttagcctct gtcgaggagc cgcctttcgc tggattgcga   5820
ggaggtagca agaacgtcgc gattttggcg attttggaat acgcgcataa tttgtttcgc   5880
attgtcgcaa gcaagtgttc gaaacgacct ttatttcttg ctttcgccga actctcaagc   5940
```

-continued

```
gcccttatcg agaaatttaa ggaggttttc cctcgtaaga gccagctcgt cgctatcgtg   6000
cgcgagtata ctcagagatt cctccgaagt cgcatgcgtg cgttgggttt gaataacgag   6060
ttcgtggtaa aatctttcgc cgatttgcta cccgcattaa tgaagcggaa ggtttcaggt   6120
tcgttcttag ctagtgttta tcgcccactt agaggtttct catatatgtg tgtttcagcg   6180
gagcgacgtg aaaagttttt tgctctcgtg tgtttaatcg ggttaagtct ccctttcttc   6240
gtgcgcatcg taggagcgaa agcgtgcgaa gaactcgtgt cctcagcgcg tcgcttttat   6300
gagcgtatta aaatttttct caggcagaag tatgtctctc tttctaattt cttttgtcac   6360
ttgtttagct ctgacgttga tgacagttcc gcatcagcag ggttgaaagg tggtgcgtcg   6420
cgaatgacgc tcttccacct tctggttcgc cttgctagtg ccctcctatc gttagggtgg   6480
gaagggttaa agctactctt atcgcaccac aacttgttat ttttgtgttt tgcattggtt   6540
gacgatgtga acgtccttat caaagttctt gggggtcttt ctttctttgt gcaaccagtc   6600
ttttccttgt ttgcggcgat gcttttacaa ccggacaggt ttgtggggta ttccgagaaa   6660
cttgttacag cgtttgaatt tttcttaaaa tgttcgcctc gcgcgcctgc actactcaaa   6720
gggttttttg agtgcgtggc gaacagcact gtgtcaaaaa ccgttcgaag acttcttcgc   6780
tatttcgtga ggatgctcaa acttcgaaaa gggcgagggt tgcgtgcgga tggtaggggt   6840
ctccatcggc agaaagccgt acccgtcata ccttctaatc gggtcgtgac cgacggggtt   6900
gaaagacttt cggtaaagat gcaaggagtt gaagcgttgc gtaccgaatt gagaatctta   6960
gaagatttag attctgccgt gatcgaaaaa ctcaatagac gcagaaatcg tgacactaat   7020
gacgacgaat ttacgcgccc tgctcatgag cagatgcaag aagtcaccac tttctgttcg   7080
aaagccaact ctgctggttt ggccctggaa agggcagtgc ttgtggaaga cgctataaag   7140
tcggagaaac tttctaagac ggttaatgag atggtgagga aagggagtac caccagcgaa   7200
gaagtggccg tcgctttgtc ggacgatgaa gccgtggaag aaatctctgt tgctgacgag   7260
cgagacgatt cgcctaagac agtcaggata agcgaatacc taaataggtt aaactcaagc   7320
ttcgaattcc cgaagcctat tgttgtggac gacaacaagg ataccggggg tctaacgaac   7380
gccgtgaggg agttttatta tatgcaagaa cttgctcttt tcgaaatcca cagcaaactg   7440
tgcgcctact acgatcaact gcgcatagtc aacttcgatc gttccgtagc accatgcagc   7500
gaagatgctc agctgtacgt acggaagagc ggctcaacga tagtgcaggg taaagaggta   7560
cgtttgcaca ttaaggattt ccacgatcac gatttcctgt ttgacgggaa aatttctatt   7620
aacaagcggc ggcgaggcgg aaacgtttta tatcacgaca acctcgcgtt cttggcgagt   7680
aatttgttct tagccggcta ccccttttca aggagcttcg tcttcacgaa ttcgtcggtc   7740
gatattctcc tctacgaagc tccacccgga ggtggtaaga cgacgacgct gattgactcg   7800
ttcttgaagg tcttcaagaa aggtgaggtt tccaccatga tcttaaccgc caacaaaagt   7860
tcgcaggttg agatcctaaa gaaagtggag aaggaagtgt ctaacattga atgccagaaa   7920
cgtaaagaca agagatctcc gaaaaagagc atttacacca tcgacgctta tttaatgcat   7980
caccgtggtt gtgatgcaga cgttctttc atcgatgagt gtttcatggt tcatgcgggt    8040
agcgtactag cttgcattga gttcacgagg tgtcataaag taatgatctt cggggatagc   8100
cggcagattc actacattga aaggaacgaa ttggacaagt gtttgtatgg ggatctcgat   8160
aggttcgtgg acctgcagtg tcgggtttat ggtaatattt cgtaccgttg tccatgggat   8220
gtgtgcgctt ggttaagcac agtgtatggc aacctaatcg ccaccgtgaa gggtgaaagc   8280
gaaggtaaga gcagcatgcg cattaacgaa attaattcag tcgacgattt agtccccgac   8340
```

-continued

```
gtgggttcca cgtttctgtg tatgcttcag tcggagaagt tggaaatcag caagcacttt   8400
attcgcaagg gtttgcctaa acttaacgtt ctaactgtgc atgaggcgca aggtgagacg   8460
tatgcgcgtg tgaaccttgt gcgacttaag tttcaggagg atgaaccctt taaatctatc   8520
aggcacataa ccgtcgctct ttctcgtcac accgacagct taacttataa cgtcttagct   8580
gctcgtcgag gtgacgccac ttgcgatgcc atccagaagg ctgcggaatt ggtgaacaag   8640
tttcgcgttt ttcctacatc ttttggtggt agtgttatca atctcaacgt gaaaaaggac   8700
gtggaagata acagtaggtg caaggcttcg tcggcaccat tgagcgtaat caacgacttt   8760
ttgaacgaag ttaatcccgg tactgcggtg attgattttg gtgatttgtc cgcggacttc   8820
agtactgggc cttttgagtg cggtgccagc ggtattgtgg tgcgggacaa catctcctcc   8880
agcaacatca ctgatcacga taagcagcgt gtttagcgta gttcggtcgc aggcgattcc   8940
gcgtagaaaa ccttctctac aagaaaattt gtattcgttt gaagcgcgga attataactt   9000
ctcgacttgc gaccgttaca catctgcttc aatgttcgga gaggctatgg cgatgaactg   9060
tcttcgtcgt tgcttcgacc tagatgcctt ttcgtccctg cgtaatgatg tgattagtat   9120
cacacgttca ggcatcgaac aatggctgga gaaacgtact cctagtcaga ttaaagcatt   9180
aatgaaggat gttgaatcgc ctttggaaat tgacgatgaa atttgtcgtt ttaagttgat   9240
ggtgaagcgt gacgctaagg tgaagttaga ctcttcttgt ttaactaaac acagcgccgc   9300
tcaaaatatc atgtttcatc gcaagagcat taatgctatc ttctctccta tctttaacga   9360
ggtgaaaaac cgaataatgt gctgtcttaa gcctaacata aagtttttta cggagatgac   9420
taacagggat tttgcttctg ttgtcagcaa catgcttggt gacgacgatg tgtaccatat   9480
aggtgaagtt gatttctcaa agtacgacaa gtctcaagat gctttcgtga aggcttttga   9540
agaagtgatg tataaggaac tcggtgttga tgaagagttg ctggctatct ggatgtgcgg   9600
cgagcggtta tcgatagcta acactctcga tggtcagttg tccttcacga tcgagaatca   9660
aaggaagtcg ggagcttcga acacttggat tggtaactct ctcgtcactt tgggtatttt   9720
aagtctttac tacgacgtta gaaatttcga ggcgttgtac atctcgggcg atgattcttt   9780
aatttttct cgcagcgaga tttcgaatta tgccgacgac atatgcactg acatgggttt   9840
tgagacaaaa tttatgtccc caagtgtccc gtacttttgt tctaaatttg ttgttatgtg   9900
tggtcataag acgtttttg ttcccgaccc gtacaagctt tttgtcaagt tgggagcagt   9960
caaagaggat gtttcaatgg atttcctttt cgaaactttt acctccttta aagacttaac  10020
ctccgatttt aacgacgagc gcttaattca aaagctcgct gaacttgtgg ctttaaaata  10080
tgaggttcaa accggcaaca ccaccttggc gttaagtgtg atacattgtt tgcgttcgaa  10140
tttcctctcg tttagcaagt tgtatcctcg cgtgaaggga tggcaggttt tttacacgtc  10200
ggttaagaaa gcgcttctca agagtgggtg ttctctcttc gacagtttca tgaccccttt  10260
tggtcaggct gtcatggttt gggatgatga gtagcgctaa cttgtgcgca gtttctttgt  10320
tcgtgacata caccttgtgt gtcaccgtgc gtttatacgg tccgggtatt caacatgatg  10380
aaaagtctca cgaagaagta caaacgagtg aatggtctgc gtgcgttctg ttgcgcgtgc  10440
gaagatctat atctaaccgt cgcaccaata atgtcagaac gctttaagac taaagccgta  10500
gggatgaaag gtttgcctgt tggaaaggaa tacttaggcg ccgactttct ttcgggaact  10560
agcaaactga tgagcgatca cgacagggcg gtctccatcg ttgcagcgaa aaacgctgtc  10620
gatcgtagcg ctttcacggg tggggagaga aagatagtta gtttgtatga tctagggagg  10680
tactaagcac ggtgtgctat agtgcgtgct ataataataa acactagtgc ttaagtcgcg  10740
```

cagaagaaaa cgcttaatta atggtgagca agggcgagga gctgttcacc ggggtggtgc 10800
ccatcctggt cgagctggac ggcgacgtaa acggccacaa gttcagcgtg tccggcgagg 10860
gcgagggcga tgccacctac ggcaagctga ccctgaagtt catctgcacc accggcaagc 10920
tgcccgtgcc ctggcccacc ctcgtgacca ccctgaccta cggcgtgcag tgcttcagcc 10980
gctaccccga ccacatgaag cagcacgact tcttcaagtc cgccatgccc gaaggctacg 11040
tccaggagcg caccatcttc ttcaaggacg acggcaacta caagacccgc gccgaggtga 11100
agttcgaggg cgacaccctg gtgaaccgca tcgagctgaa gggcatcgac ttcaaggagg 11160
acggcaacat cctggggcac aagctggagt acaactacaa cagccacaac gtctatatca 11220
tggccgacaa gcagaagaac ggcatcaagg tgaacttcaa gatccgccac aacatcgagg 11280
acggcagcgt gcagctcgcc gaccactacc agcagaacac ccccatcggc gacggccccg 11340
tgctgctgcc cgacaaccac tacctgagca cccagtccgc cctgagcaaa gaccccaacg 11400
agaagcgcga tcacatggtc ctgctggagt tcgtgaccgc cgccgggatc actctcggca 11460
tggacgagct gtacaagtcc ctagggatgg tccgtcctgt agaaacccca acccgtgaaa 11520
tcaaaaaact cgacggcctg tgggcattca gtctggatcg cgaaaactgt ggaattgatc 11580
agcgttggtg ggaaagcgcg ttacaagaaa gccgggcaat tgctgtgcca ggcagtttta 11640
acgatcagtt cgccgatgca gatattcgta attatgcggg caacgtctgg tatcagcgcg 11700
aagtctttat accgaaaggt tgggcaggcc agcgtatcgt gctgcgtttc gatgcggtca 11760
ctcattacgg caaagtgtgg gtcaataatc aggaagtgat ggagcatcag ggcggctata 11820
cgccatttga agccgatgtc acgccgtatg ttattgccgg gaaaagtgta cgtatcaccg 11880
tttgtgtgaa caacgaactg aactggcaga ctatcccgcc gggaatggtg attaccgacg 11940
aaaacggcaa gaaaaagcag tcttacttcc atgatttctt taactatgcc ggaatccatc 12000
gcagcgtaat gctctacacc acgccgaaca cctgggtgga cgatatcacc gtggtgacgc 12060
atgtcgcgca agactgtaac cacgcgtctg ttgactggca ggtggtggcc aatggtgatg 12120
tcagcgttga actgcgtgat gcggatcaac aggtggttgc aactggacaa ggcactagcg 12180
ggactttgca agtggtgaat ccgcacctct ggcaaccggg tgaaggttat ctctatgaac 12240
tgtgcgtcac agccaaaagc cagacagagt gtgatatcta cccgcttcgc gtcggcatcc 12300
ggtcagtggc agtgaagggc gaacagttcc tgattaacca caaaccgttc tactttactg 12360
gctttggtcg tcatgaagat gcggacttgc gtggcaaagg attcgataac gtgctgatgg 12420
tgcacgacca cgcattaatg gactggattg gggccaactc ctaccgtacc tcgcattacc 12480
cttacgctga agagatgctc gactgggcag atgaacatgg catcgtggtg attgatgaaa 12540
ctgctgctgt cggctttaac ctctctttag gcattggttt cgaagcgggc aacaagccga 12600
aagaactgta cagcgaagag gcagtcaacg gggaaactca gcaagcgcac ttacaggcga 12660
ttaaagagct gatagcgcgt gacaaaaacc acccaagcgt ggtgatgtgg agtattgcca 12720
acgaaccgga tacccgtccg caaggtgcac gggaatattt cgcgccactg gcggaagcaa 12780
cgcgtaaact cgacccgacg cgtccgatca cctgcgtcaa tgtaatgttc tgcgacgctc 12840
acaccgatac catcagcgat ctctttgatg tgctgtgcct gaaccgttat tacggatggt 12900
atgtccaaag cggcgatttg gaaacggcag agaaggtact ggaaaaagaa cttctggcct 12960
ggcaggagaa actgcatcag ccgattatca tcaccgaata cggcgtggat acgttagccg 13020
ggctgcactc aatgtacacc gacatgtgga gtgaagagta tcagtgtgca tggctggata 13080
tgtatcaccg cgtctttgat cgcgtcagcg ccgtcgtcgg tgaacaggta tggaatttcg 13140

```
ccgattttgc gacctcgcaa ggcatattgc gcgttggcgg taacaagaaa gggatcttca  13200

ctcgcgaccg caaaccgaag tcggcggctt ttctgctgca aaaacgctgg actggcatga  13260

acttcggtga aaaaccgcag cagggaggca aacaatgagg ccggcctttg cggttactta  13320

cgagtgtcag gacgtgggga ggtgacgtgt tgcaaccgtg aggaattaac aagagatttt  13380

gagggcaatc atcatacggt gatccgttct agaatcatac aatatgacag cgagtctgct  13440

tttgaggaat tcaacaactc tgattgcgta gtgaagtttt tcctagagac tggtagtgtc  13500

ttttggtttt tccttcgaag tgaaaccaaa ggtagagcgg tgcgacattt gcgcaccttc  13560

ttcgaagcta acaatttctt ctttggatcg cattgcggta ccatggagta ttgtttgaag  13620

caggtactat ctgaaactga atctataatc gattcttttt gcgaagaaag aaatcgttaa  13680

gatgagggtt atagtgtctc cttatgaagc tgaagacatt ctgaaaagat cgactgacat  13740

gttacgaaac atagacagtg ggtcttgag cactaaagaa tgtatcaagg cattctcgac  13800

gataacgcga gacctacatt gtgcgaaggc ttcctaccag tggggtgttg acactgggtt  13860

atatcagcgt aattgcgctg aaaaacattt aattgacacg gtggagtcaa acatacggtt  13920

ggctcaacct ctcgtgcgtg aaaaagtggc ggttcatttt tgtaaggatg aaccaaaaga  13980

gctagtagca ttcatcacgc gaaagtacgt ggaactcacg ggcgtgggag tgagagaagc  14040

ggtgaagagg gaaatgcgct ctcttaccaa aacagtttta aataaaatgt ctttggaaat  14100

ggcgttttac atgtcaccac gagcgtggaa aaacgctgaa tggttagaac taaaattttc  14160

acctgtgaaa atctttagag atcttttatt agacgtggaa acgctcaacg aattgtgcgc  14220

cgaagatgat gttcacgtcg acaaagtaaa tgagaatggg gacgaaaatc acgacctcga  14280

actccaagac gaatgttaaa cattggttaa gtttaacgaa aatgattagt aaataataaa  14340

tcgaacgtgg gtgtatctac ctgacgtatc aacttaagct gttactgagt aattaaacca  14400

acaagtgttg gtgtaatgtg tatgttgatg tagagaaaaa tccgtttgta gaacggtgtt  14460

tttctcttct ttatttttaa aaaaaaataa aaaaaaaaaa aaagaagc              14508
```

```
<210> SEQ ID NO 3
<211> LENGTH: 1716
<212> TYPE: DNA
<213> ORGANISM: Grapevine leafroll virus-2
<220> FEATURE:
<221> NAME/KEY: CDS
<222> LOCATION: (1)..(1716)

<400> SEQUENCE: 3

atg tct agc ctt gct atc tct gcc ctt ccc tgt tca gtc gct caa ctg       48
Met Ser Ser Leu Ala Ile Ser Ala Leu Pro Cys Ser Val Ala Gln Leu
1               5                   10                  15

agc gtt ggt cag cct gtt gcc acg gtt gcc agg tca ttt ttg atg act       96
Ser Val Gly Gln Pro Val Ala Thr Val Ala Arg Ser Phe Leu Met Thr
            20                  25                  30

tcc ctt ccg tcc ctt cag act tac cca tct tcg tct gag ttg act tcc      144
Ser Leu Pro Ser Leu Gln Thr Tyr Pro Ser Ser Ser Glu Leu Thr Ser
        35                  40                  45

ttt tta ttt tgt ttt ggt gct ttc caa aaa ata aaa atg ttt tta tct      192
Phe Leu Phe Cys Phe Gly Ala Phe Gln Lys Ile Lys Met Phe Leu Ser
    50                  55                  60

ttc cta cgt tcg gtg cac gtc ttt gcg cct ttt tct gaa att tcc acg      240
Phe Leu Arg Ser Val His Val Phe Ala Pro Phe Ser Glu Ile Ser Thr
65                  70                  75                  80

att ggt tca tgc tat gaa ttc att cgg ttg gga ggt ggt gct tac cct      288
Ile Gly Ser Cys Tyr Glu Phe Ile Arg Leu Gly Gly Gly Ala Tyr Pro
```

-continued

```
                85                  90                  95

ctc ttt ttc tgt tcc ttc caa tgc gga cct ttg tcc gtt tct ttg ggt      336
Leu Phe Phe Cys Ser Phe Gln Cys Gly Pro Leu Ser Val Ser Leu Gly
            100                 105                 110

ttt gtt aac ggc gtt ttt gct gtt tta aac atg tca ttt cct ttc tta      384
Phe Val Asn Gly Val Phe Ala Val Leu Asn Met Ser Phe Pro Phe Leu
        115                 120                 125

agc aac gca tct ctt ttg acg ggc gtc gga aaa aat gtt gtt caa gag      432
Ser Asn Ala Ser Leu Leu Thr Gly Val Gly Lys Asn Val Val Gln Glu
    130                 135                 140

aaa ata aaa att tcc aaa ttt gag aag aaa cag aag aag cgc gtt ttt      480
Lys Ile Lys Ile Ser Lys Phe Glu Lys Lys Gln Lys Lys Arg Val Phe
145                 150                 155                 160

tcg ata gct cgc gct acc gcg cgt cat gtg cct tcc cgt cgc aat cct      528
Ser Ile Ala Arg Ala Thr Ala Arg His Val Pro Ser Arg Arg Asn Pro
                165                 170                 175

aag gag aag cgt gtt gtc cat gta cag cat ctc cct agt ggt tct tta      576
Lys Glu Lys Arg Val Val His Val Gln His Leu Pro Ser Gly Ser Leu
            180                 185                 190

cgc ttt tcc caa aac aaa aac aaa aca gaa ctg ctc atc tta aaa gag      624
Arg Phe Ser Gln Asn Lys Asn Lys Thr Glu Leu Leu Ile Leu Lys Glu
        195                 200                 205

gaa gtc gga att gtc gcg cgc gtt aag tgt tcg gca agc gtc gtg cgc      672
Glu Val Gly Ile Val Ala Arg Val Lys Cys Ser Ala Ser Val Val Arg
    210                 215                 220

cgt cgc gtt tgt ggc ggt gtg gtt aag tgc aaa ccc cta ata gcc gtt      720
Arg Arg Val Cys Gly Gly Val Val Lys Cys Lys Pro Leu Ile Ala Val
225                 230                 235                 240

tct ccc tct ggc gtg aaa ttc cgt tgt ttc gcg ccg tct tgc agc acg      768
Ser Pro Ser Gly Val Lys Phe Arg Cys Phe Ala Pro Ser Cys Ser Thr
                245                 250                 255

tcc gct tgt tta aag ctc aaa atc atg cgc cgt gtt gcc gtc ggt gac      816
Ser Ala Cys Leu Lys Leu Lys Ile Met Arg Arg Val Ala Val Gly Asp
            260                 265                 270

tgc cga ggt gag aag ata atc gcg gca cga cgt gcg gcg ctg cag aag      864
Cys Arg Gly Glu Lys Ile Ile Ala Ala Arg Arg Ala Ala Leu Gln Lys
        275                 280                 285

cag gct ttc aac agc cgc aca ccg aag aaa gtg cga gag aac ccc att      912
Gln Ala Phe Asn Ser Arg Thr Pro Lys Lys Val Arg Glu Asn Pro Ile
    290                 295                 300

agc gtc tcc ggg gtg aac ttg gga agg tct gcc gcc gct cag gtt att      960
Ser Val Ser Gly Val Asn Leu Gly Arg Ser Ala Ala Ala Gln Val Ile
305                 310                 315                 320

tat ttc ggc agt ttc acg cag ccc ttc gcg ttg tat ccg cgc caa gag     1008
Tyr Phe Gly Ser Phe Thr Gln Pro Phe Ala Leu Tyr Pro Arg Gln Glu
                325                 330                 335

agc gcg atc gta aaa acg caa cct cca ccg gtc agt gta gtg aag gtg     1056
Ser Ala Ile Val Lys Thr Gln Pro Pro Pro Val Ser Val Val Lys Val
            340                 345                 350

gag tgc gta gct gcg gag gta gct ccc gac agg ggc gtg gtc gac aag     1104
Glu Cys Val Ala Ala Glu Val Ala Pro Asp Arg Gly Val Val Asp Lys
        355                 360                 365

aaa cct acg tct gtt ggc gtt ccc ccg cag cgc ggt gtg ctt tct ttt     1152
Lys Pro Thr Ser Val Gly Val Pro Pro Gln Arg Gly Val Leu Ser Phe
    370                 375                 380

ccg acg gtg gtt cgg aac cgc ggc gac gtg ata atc aca ggg gtg gtg     1200
Pro Thr Val Val Arg Asn Arg Gly Asp Val Ile Ile Thr Gly Val Val
385                 390                 395                 400

cat gaa gcc ctg aag aaa att aaa gac ggg ctc tta cgc ttc cgc gta     1248
His Glu Ala Leu Lys Lys Ile Lys Asp Gly Leu Leu Arg Phe Arg Val
```

```
                405                 410                 415

ggc ggt gac atg cgt ttt tcg aga ttt ttc tca tcg aac tac ggc tgc      1296
Gly Gly Asp Met Arg Phe Ser Arg Phe Phe Ser Ser Asn Tyr Gly Cys
            420                 425                 430

aga ttc gtc gcg agc gtg cgt acg aac act aca gtt tgg cta aat tgc      1344
Arg Phe Val Ala Ser Val Arg Thr Asn Thr Thr Val Trp Leu Asn Cys
        435                 440                 445

acg aaa gcg agt ggt gag aaa ttc tca ctc gcc gcc gcg tgc acg gcg      1392
Thr Lys Ala Ser Gly Glu Lys Phe Ser Leu Ala Ala Ala Cys Thr Ala
    450                 455                 460

gat tac gtg gcg atg ctg cgt tat gtg tgt ggc ggg aaa ttt cct ctc      1440
Asp Tyr Val Ala Met Leu Arg Tyr Val Cys Gly Gly Lys Phe Pro Leu
465                 470                 475                 480

gtc ctc atg agt aga gtt att tac ccg gat ggg cgc tgt tac ttg gcc      1488
Val Leu Met Ser Arg Val Ile Tyr Pro Asp Gly Arg Cys Tyr Leu Ala
                485                 490                 495

cat atg agg tat ttg tgc gcc ttt tac tgt cgc ccg ttt aga gag tcg      1536
His Met Arg Tyr Leu Cys Ala Phe Tyr Cys Arg Pro Phe Arg Glu Ser
            500                 505                 510

gat tat gcc ctc gga atg tgg cct acg gtg gcg cgt ctc agg gca tgc      1584
Asp Tyr Ala Leu Gly Met Trp Pro Thr Val Ala Arg Leu Arg Ala Cys
        515                 520                 525

gtt gag aag aac ttc ggt gtc gaa gct tgt ggc ata gct ctt cgt ggc      1632
Val Glu Lys Asn Phe Gly Val Glu Ala Cys Gly Ile Ala Leu Arg Gly
    530                 535                 540

tat tac acc tct cgc aat gtt tat cac tgt gat tat gac tct gct tat      1680
Tyr Tyr Thr Ser Arg Asn Val Tyr His Cys Asp Tyr Asp Ser Ala Tyr
545                 550                 555                 560

gta aaa tat ttt aga aac ctt tcc ggc cgc att ggc                      1716
Val Lys Tyr Phe Arg Asn Leu Ser Gly Arg Ile Gly
                565                 570


<210> SEQ ID NO 4
<211> LENGTH: 572
<212> TYPE: PRT
<213> ORGANISM: Grapevine leafroll virus-2

<400> SEQUENCE: 4

Met Ser Ser Leu Ala Ile Ser Ala Leu Pro Cys Ser Val Ala Gln Leu
1               5                   10                  15

Ser Val Gly Gln Pro Val Ala Thr Val Ala Arg Ser Phe Leu Met Thr
            20                  25                  30

Ser Leu Pro Ser Leu Gln Thr Tyr Pro Ser Ser Ser Glu Leu Thr Ser
        35                  40                  45

Phe Leu Phe Cys Phe Gly Ala Phe Gln Lys Ile Lys Met Phe Leu Ser
    50                  55                  60

Phe Leu Arg Ser Val His Val Phe Ala Pro Phe Ser Glu Ile Ser Thr
65                  70                  75                  80

Ile Gly Ser Cys Tyr Glu Phe Ile Arg Leu Gly Gly Gly Ala Tyr Pro
                85                  90                  95

Leu Phe Phe Cys Ser Phe Gln Cys Gly Pro Leu Ser Val Ser Leu Gly
            100                 105                 110

Phe Val Asn Gly Val Phe Ala Val Leu Asn Met Ser Phe Pro Phe Leu
        115                 120                 125

Ser Asn Ala Ser Leu Leu Thr Gly Val Gly Lys Asn Val Val Gln Glu
    130                 135                 140

Lys Ile Lys Ile Ser Lys Phe Glu Lys Lys Gln Lys Lys Arg Val Phe
145                 150                 155                 160
```

```
Ser Ile Ala Arg Ala Thr Ala Arg His Val Pro Ser Arg Arg Asn Pro
                165                 170                 175

Lys Glu Lys Arg Val Val His Val Gln His Leu Pro Ser Gly Ser Leu
            180                 185                 190

Arg Phe Ser Gln Asn Lys Asn Lys Thr Glu Leu Leu Ile Leu Lys Glu
        195                 200                 205

Glu Val Gly Ile Val Ala Arg Val Lys Cys Ser Ala Ser Val Val Arg
    210                 215                 220

Arg Arg Val Cys Gly Gly Val Val Lys Cys Lys Pro Leu Ile Ala Val
225                 230                 235                 240

Ser Pro Ser Gly Val Lys Phe Arg Cys Phe Ala Pro Ser Cys Ser Thr
                245                 250                 255

Ser Ala Cys Leu Lys Leu Lys Ile Met Arg Arg Val Ala Val Gly Asp
            260                 265                 270

Cys Arg Gly Glu Lys Ile Ile Ala Ala Arg Arg Ala Ala Leu Gln Lys
        275                 280                 285

Gln Ala Phe Asn Ser Arg Thr Pro Lys Lys Val Arg Glu Asn Pro Ile
    290                 295                 300

Ser Val Ser Gly Val Asn Leu Gly Arg Ser Ala Ala Ala Gln Val Ile
305                 310                 315                 320

Tyr Phe Gly Ser Phe Thr Gln Pro Phe Ala Leu Tyr Pro Arg Gln Glu
                325                 330                 335

Ser Ala Ile Val Lys Thr Gln Pro Pro Pro Val Ser Val Val Lys Val
            340                 345                 350

Glu Cys Val Ala Ala Glu Val Ala Pro Asp Arg Gly Val Val Asp Lys
        355                 360                 365

Lys Pro Thr Ser Val Gly Val Pro Pro Gln Arg Gly Val Leu Ser Phe
    370                 375                 380

Pro Thr Val Val Arg Asn Arg Gly Asp Val Ile Ile Thr Gly Val Val
385                 390                 395                 400

His Glu Ala Leu Lys Lys Ile Lys Asp Gly Leu Leu Arg Phe Arg Val
                405                 410                 415

Gly Gly Asp Met Arg Phe Ser Arg Phe Phe Ser Ser Asn Tyr Gly Cys
            420                 425                 430

Arg Phe Val Ala Ser Val Arg Thr Asn Thr Thr Val Trp Leu Asn Cys
        435                 440                 445

Thr Lys Ala Ser Gly Glu Lys Phe Ser Leu Ala Ala Ala Cys Thr Ala
    450                 455                 460

Asp Tyr Val Ala Met Leu Arg Tyr Val Cys Gly Gly Lys Phe Pro Leu
465                 470                 475                 480

Val Leu Met Ser Arg Val Ile Tyr Pro Asp Gly Arg Cys Tyr Leu Ala
                485                 490                 495

His Met Arg Tyr Leu Cys Ala Phe Tyr Cys Arg Pro Phe Arg Glu Ser
            500                 505                 510

Asp Tyr Ala Leu Gly Met Trp Pro Thr Val Ala Arg Leu Arg Ala Cys
        515                 520                 525

Val Glu Lys Asn Phe Gly Val Glu Ala Cys Gly Ile Ala Leu Arg Gly
    530                 535                 540

Tyr Tyr Thr Ser Arg Asn Val Tyr His Cys Asp Tyr Asp Ser Ala Tyr
545                 550                 555                 560

Val Lys Tyr Phe Arg Asn Leu Ser Gly Arg Ile Gly
                565                 570
```

<210> SEQ ID NO 5

-continued

<211> LENGTH: 825
<212> TYPE: DNA
<213> ORGANISM: Grapevine leafroll virus-2
<220> FEATURE:
<221> NAME/KEY: CDS
<222> LOCATION: (1)..(825)

<400> SEQUENCE: 5

```
ggt ggt tcg ttc gat ccg aca tct tta acc tcc gta ata acg gtg aag       48
Gly Gly Ser Phe Asp Pro Thr Ser Leu Thr Ser Val Ile Thr Val Lys
1               5                   10                  15

att agc ggt ctt cca ggt ggt ctt cct aaa aat ata gcg ttt ggt gcc       96
Ile Ser Gly Leu Pro Gly Gly Leu Pro Lys Asn Ile Ala Phe Gly Ala
            20                  25                  30

ttc ctg tgc gat ata cgt tac gtc gaa ccg gta gac tcg ggc ggc att      144
Phe Leu Cys Asp Ile Arg Tyr Val Glu Pro Val Asp Ser Gly Gly Ile
        35                  40                  45

caa tcg agc gtt aag acg aaa cgt gaa gat gcg cac cga acc gta gag      192
Gln Ser Ser Val Lys Thr Lys Arg Glu Asp Ala His Arg Thr Val Glu
    50                  55                  60

gaa cgg gcg gcc ggc gga tcc gtc gag caa ccg cga caa aag agg ata      240
Glu Arg Ala Ala Gly Gly Ser Val Glu Gln Pro Arg Gln Lys Arg Ile
65                  70                  75                  80

gat gag aaa ggt tgc ggc aga gtt cct agt gga ggt ttt tcg cat ctc      288
Asp Glu Lys Gly Cys Gly Arg Val Pro Ser Gly Gly Phe Ser His Leu
                85                  90                  95

ctg gtc ggc agc ctt aac gaa gtt agg agg aag gta gct gcc gga ctt      336
Leu Val Gly Ser Leu Asn Glu Val Arg Arg Lys Val Ala Ala Gly Leu
            100                 105                 110

cta cgc ttt cgc gtt ggc ggt gat atg gat ttt cat cgc tcg ttc tcc      384
Leu Arg Phe Arg Val Gly Gly Asp Met Asp Phe His Arg Ser Phe Ser
        115                 120                 125

acc caa gcg ggc cac cgc ttg ctg gtg tgg cgc cgc tcg agc cgg agc      432
Thr Gln Ala Gly His Arg Leu Leu Val Trp Arg Arg Ser Ser Arg Ser
    130                 135                 140

gtg tgc ctt gaa ctt tac tca cca tct aaa aac ttt ttg cgt tac gat      480
Val Cys Leu Glu Leu Tyr Ser Pro Ser Lys Asn Phe Leu Arg Tyr Asp
145                 150                 155                 160

gtc ttg cct tgt tct gga gac tat gca gcg atg ttt tct ttc gcg gcg      528
Val Leu Pro Cys Ser Gly Asp Tyr Ala Ala Met Phe Ser Phe Ala Ala
                165                 170                 175

ggc ggc cgt ttc cct tta gtt ttg atg act aga att aga tac ccg aac      576
Gly Gly Arg Phe Pro Leu Val Leu Met Thr Arg Ile Arg Tyr Pro Asn
            180                 185                 190

ggg ttt tgt tac ttg gct cac tgc cgg tac gcg tgc gcg ttt ctc tta      624
Gly Phe Cys Tyr Leu Ala His Cys Arg Tyr Ala Cys Ala Phe Leu Leu
        195                 200                 205

agg ggt ttt gat ccg aag cgt ttc gac atc ggt gct ttc ccc acc gca      672
Arg Gly Phe Asp Pro Lys Arg Phe Asp Ile Gly Ala Phe Pro Thr Ala
    210                 215                 220

gcc aag ctc aga aac cgt atg gtt tcg gag ctt ggt gaa aga agt tta      720
Ala Lys Leu Arg Asn Arg Met Val Ser Glu Leu Gly Glu Arg Ser Leu
225                 230                 235                 240

ggt ttg aac ttg tac ggc gca tat acg tca cgc ggc gtc ttt cac tgc      768
Gly Leu Asn Leu Tyr Gly Ala Tyr Thr Ser Arg Gly Val Phe His Cys
                245                 250                 255

gat tat gac gct aag ttt ata aag gat ttg cgt ctt atg tca gca gtt      816
Asp Tyr Asp Ala Lys Phe Ile Lys Asp Leu Arg Leu Met Ser Ala Val
            260                 265                 270

ata gct gga                                                          825
Ile Ala Gly
        275
```

<210> SEQ ID NO 6
<211> LENGTH: 275
<212> TYPE: PRT
<213> ORGANISM: Grapevine leafroll virus-2

<400> SEQUENCE: 6

```
Gly Gly Ser Phe Asp Pro Thr Ser Leu Thr Ser Val Ile Thr Val Lys
1               5                   10                  15

Ile Ser Gly Leu Pro Gly Gly Leu Pro Lys Asn Ile Ala Phe Gly Ala
            20                  25                  30

Phe Leu Cys Asp Ile Arg Tyr Val Glu Pro Val Asp Ser Gly Gly Ile
        35                  40                  45

Gln Ser Ser Val Lys Thr Lys Arg Glu Asp Ala His Arg Thr Val Glu
    50                  55                  60

Glu Arg Ala Ala Gly Gly Ser Val Glu Gln Pro Arg Gln Lys Arg Ile
65                  70                  75                  80

Asp Glu Lys Gly Cys Gly Arg Val Pro Ser Gly Gly Phe Ser His Leu
                85                  90                  95

Leu Val Gly Ser Leu Asn Glu Val Arg Arg Lys Val Ala Ala Gly Leu
            100                 105                 110

Leu Arg Phe Arg Val Gly Gly Asp Met Asp Phe His Arg Ser Phe Ser
        115                 120                 125

Thr Gln Ala Gly His Arg Leu Leu Val Trp Arg Arg Ser Ser Arg Ser
    130                 135                 140

Val Cys Leu Glu Leu Tyr Ser Pro Ser Lys Asn Phe Leu Arg Tyr Asp
145                 150                 155                 160

Val Leu Pro Cys Ser Gly Asp Tyr Ala Ala Met Phe Ser Phe Ala Ala
                165                 170                 175

Gly Gly Arg Phe Pro Leu Val Leu Met Thr Arg Ile Arg Tyr Pro Asn
            180                 185                 190

Gly Phe Cys Tyr Leu Ala His Cys Arg Tyr Ala Cys Ala Phe Leu Leu
        195                 200                 205

Arg Gly Phe Asp Pro Lys Arg Phe Asp Ile Gly Ala Phe Pro Thr Ala
    210                 215                 220

Ala Lys Leu Arg Asn Arg Met Val Ser Glu Leu Gly Glu Arg Ser Leu
225                 230                 235                 240

Gly Leu Asn Leu Tyr Gly Ala Tyr Thr Ser Arg Gly Val Phe His Cys
                245                 250                 255

Asp Tyr Asp Ala Lys Phe Ile Lys Asp Leu Arg Leu Met Ser Ala Val
            260                 265                 270

Ile Ala Gly
        275
```

<210> SEQ ID NO 7
<211> LENGTH: 17588
<212> TYPE: DNA
<213> ORGANISM: Artificial sequence
<220> FEATURE:
<223> OTHER INFORMATION: Engineered viral vector

<400> SEQUENCE: 7

```
atattctgtt ggctttcatc tgtgcttgtg cttcggttca atcacactct gaaagtttca      60

gttccccgga atttcggttt tcttcataag ccttattctt acaggatgtc tagccttgct     120

atctctgccc ttccctgttc agtcgctcaa ctgagcgttg gtcagcctgt tgccacggtt     180

gccaggtcat ttttgatgac ttcccttccg tcccttcaga cttacccatc ttcgtctgag     240
```

-continued

```
ttgacttcct ttttattttg ttttggtgct ttccaaaaaa taaaaatgtt tttatctttc    300
ctacgttcgg tgcacgtctt tgcgcctttt tctgaaattt ccacgattgg ttcatgctat    360
gaattcattc ggttgggagg tggtgcttac cctctctttt tctgttcctt ccaatgcgga    420
cctttgtccg tttctttggg ttttgttaac ggcgtttttg ctgttttaaa catgtcattt    480
cctttcttaa gcaacgcatc tcttttgacg ggcgtcggaa aaaatgttgt tcaagagaaa    540
ataaaaattt ccaaatttga gaagaaacag aagaagcgcg tttttcgat agctcgcgct     600
accgcgcgtc atgtgccttc ccgtcgcaat cctaaggaga agcgtgttgt ccatgtacag    660
catctcccta gtggttcttt acgcttttcc caaaacaaaa acaaaacaga actgctcatc    720
ttaaaagagg aagtcggaat tgtcgcgcgc gttaagtgtt cggcaagcgt cgtgcgccgt    780
cgcgtttgtg gcggtgtggt taagtgcaaa cccctaatag ccgtttctcc ctctggcgtg    840
aaattccgtt gtttcgcgcc gtcttgcagc acgtccgctt gtttaaagct caaaatcatg    900
cgccgtgttg ccgtcggtga ctgccgaggt gagaagataa tcgcggcacg acgtgcggcg    960
ctgcagaagc aggctttcaa cagccgcaca ccgaagaaag tgcgagagaa ccccattagc   1020
gtctccgggg tgaacttggg aaggtctgcc accgctcagg ttatttattt cggcagtttc   1080
acgcagccct tcgcgttgta tccgcgccaa gagagcgcga tcgtaaaaac gcaacctcca   1140
ccggtcagtg tagtgaaggt ggagtgcgta gctgcggagg tagctcccaa caggggcgtg   1200
gtcgacaaga aacctacgtc tgttggcgtt cccccgcagc gcggtgtgct ttcttttccg   1260
acggtggttc ggaaccgcgg cgacgtgata atcgcagggg tggtgcatga agccttgaag   1320
aaaattaaag acgggctctt acgcttccgc gtaggcggtg acatgcgttt ttcgagattt   1380
ttctcatcga actacggctg cagattcgtc gcgagcgtgc gtacgaacac tacagtttgg   1440
ctaaattgca cgaaagcgag tggtgagaaa ttctcactcg ccgccgcgtg cacggcggat   1500
tacgtggcga tgctgcgtta tgtatgtggc gggaaatttc ctctcgtcct catgagtaga   1560
gttatttacc cggaagggcg ctgttacttg gcccatatga ggtatttgtg cgccttttac   1620
tgtcgcccgt ttagagagtc ggattatgcc ctcggaatgt ggcctacggt ggcgcgtctc   1680
agggcatgcg ttgagaagaa cttcggtgtc gaagcttgtg gcatagctct tcgtggctat   1740
tacacctctc gcaatgttta tcactgtgat tatgactctg cttatgtaaa atattttaga   1800
aacctttccg gccgcattgg cggtggttcg ttcgatccga catctttaac ctccgtaata   1860
acggtgaaga ttagcggtct tccaggtggt cttcctaaaa atatagcgtt tggtgccttc   1920
ctgtgcgata tacgttacgt cgaaccggta gactcgggcg gcattcaatc gagcgttaag   1980
acgaaacgtg aagatgcgca ccgaaccgta gaggaacggg cggccggcgg atccgtcgag   2040
caaccgcgac aaaagaggat agatgagaaa ggttgcggca gagttcctag tggaggtttt   2100
ccgcatctcc tggtcggcag ccttaacgaa gttaggagga aggtagctgc cggacttcta   2160
cgctttcgcg ttggcggtga tatggatttt catcgctcgt tctccaccca agcgggccac   2220
cgcttgctgg tgtggcgccg ctcgagccgg agcgtgtgcc ttgaacttta ctcaccatct   2280
aaaaactttt tgcgttgcga tgtcttgcct tgttctggag actatgcagc gatgttttct   2340
ttcgcggcgg gcggccgttt ccctttagtt ttgatgacta gaattagata cccgaacggg   2400
ttttgttact tggctcactg ccggtacgcg tgcgcgtttc tcttaagggg ttttgatccg   2460
aagcgtttcg acatcggtgc tttccccacc gcggccaagc tcagaaaccg tatggtttcg   2520
gagcttggtg aaagaagttt aggtttgaac ttgtacggcg catatacgtc acgcggcgtc   2580
tttcactgcg attatgacgc taagtttata aaggatttgc gtcttatgtc agcagttata   2640
```

-continued

```
gctggaaagg acggggtgga agaggtggta ccttctgaca taactcctgc catgaagcag   2700
aaaacgatcg aagccgtgta tgatagatta tatggcggca ctgactcgtt gctgaaactg   2760
agcatcgaga aagacttaat cgatttcaaa aatgacgtgc agagtttgaa gaaagatcgg   2820
ccgattgtca aagtgccctt ttacatgtcg gaagcaacac agaattcgct gacgcgtttc   2880
taccctcagt tcgaacttaa gttttcgcac tcctcgcatt cagatcatcc cgccgccgcc   2940
gcttctagac tgctggaaaa tgaaacgtta gtgcgcttat gtggtaatag cgtttcagat   3000
attggaggtt gtcctctttt ccatttgcat tccaagacgc aaagacgggt tcacgtatgt   3060
aggcctgtgt tggatggcaa ggatgcgcag cgtcgcgtgg tgcgtgattt gcagtattcc   3120
aacgtgcgtt tgggagacga tgataaaatt ctggaagggc cacgcaatat cgacatttgc   3180
cactatcctc tgggcgcgtg tgaccacgaa agtagtgcta tgatgatggt gcaggtgtat   3240
gacgcgtccc tttatgagat atgtggcgcc atgatcaaga agaaaagccg cataacgtac   3300
ttaaccatgg tcacgcccgg cgagtttctt gacggacgcg aatgcgtcta tatggagtcg   3360
ttagactgtg agattgaggt tgatgtgcac gcggacgtcg taatgtacaa attcggtagt   3420
tcttgctatt cgcacaagct ttcaatcatc aaggacatca tgaccactcc gtacttgaca   3480
ctaggtggtt ttctattcag cgtggagatg tatgaggtgc gtatgggcgt gaattacttc   3540
aagattacga agtccgaagt atcgcctagc attagctgca ccaagctcct gagatatcga   3600
agagctaata gcgacgtggt taaagttaaa cttccacgtt tcgataagaa acgtcgcatg   3660
tgtctgcctg ggtatgacac catataccta gattcgaagt ttgtgagtcg cgttttcgat   3720
tatgtcgtgt gtaattgctc tgccgtgaac tcaaaaactt tcgagtgggt gtggagtttc   3780
attaagtcta gcaagtcgag ggtgattatt agcggtaaaa taattcacaa ggatgtgaat   3840
ttggacctca agtacgtcga gagtttcgcc gcggttatgt tggcctctgg cgtgcgcagc   3900
agactagcgt ccgagtacct tgctaagaac cttagtcatt tttcgggaga ttgctccttt   3960
attgaagcca cgtctttcgt gttgcgtgag aaaatcagaa acatgactct gaattttaac   4020
gaaagacttt tacagttagt gaagcgcgtt gcctttgcga ccttggacgt gagttttcta   4080
gatttagatt caactcttga atcaataact gattttgccg agtgtaaggt agcgattgaa   4140
ctcgacgagt tgggttgctt gagagcggag gccgagaatg aaaaaatcag gaatctagcg   4200
ggagattcga ttgcggctaa actcgcgagc gagatagtgg tcgatattga ctctaagcct   4260
tcaccgaagc aggtgggtaa ttcgtcatcc gaaaacgccg ataagcggga agttcagagg   4320
cccggtttgc gtggtggttc taggaacggg gttgttgggg agttccttca cttcgtcgtg   4380
gattctgcct tgcgtctttt cagatacgcg acggatcaac aacggatcaa gtcttacgtg   4440
cgtttcttgg actcggcggt ctcattcttg gattacaact acgataatct atcgtttata   4500
ctgcgagtgc tttcggaagg ttattcgtgt atgttcgcgt tttggcgaa tcgcggcgac   4560
ttatctagtc gtgtccgtag cgcggtgcgt gctgtgaaag aagttgctac ctcatgcgcg   4620
aacgcgagcg tttctaaagc caaggttatg attaccttcg cagcggccgt gtgtgctatg   4680
atgtttaata gctgcggttt ttcaggcgac ggtcgggagt ataaatcgta tatacatcgt   4740
tacacgcaag tattgttcga cactatcttt tttgaggaca gcagttacct acccatagaa   4800
gttctgagtt cggcgatatg cggtgctatc gtcacacttt tctcctcggg ctcgtccata   4860
agtttaaacg ccttcttact tcaaattacc aaaggattct ccctagaggt tgtcgtccgg   4920
aatgttgtgc gagtcacgca tggtttgagc accacagcga ccgacggcgt catacgtggg   4980
gttttctccc aaattgtgtc tcacttactt gttggaaata ccggtaatgt ggcttaccag   5040
```

-continued

```
tcagctttca ttgccggggt ggtgcctctt ttagttaaaa agtgtgtgag cttaatcttc   5100
atcttgcgtg aagatactta ttccggtttt attaagcacg gaatcagtga attctctttc   5160
cttagtagta ttctgaagtt cttgaagggt aagcttgtgg acgagttgaa atcgattatt   5220
caaggggttt ttgattccaa caagcacgtg tttaaagaag ctactcagga agcgattcgt   5280
acgacggtca tgcaagtgcc tgtcgctgta gtggatgccc ttaagagcgc cgcgggaaaa   5340
atttataaca attttactag tcgacgtacc tttggtaagg atgaaggctc ctctagcgac   5400
ggcgcatgtg aagagtattt ctcatgcgac gaaggtgaag gtccgggtct gaaagggggt   5460
tccagctatg gcttctcaat tttagcgttc ttttcacgca ttatgtgggg agctcgtcgg   5520
cttattgtta aggtgaagca tgagtgtttt gggaaacttt ttgaatttct atcgctcaag   5580
cttcacgaat tcaggactcg cgtttttggg aagaatggaa cggacgtggg agtttacgat   5640
tttttgccca cggacatcgt ggaaacgctc tcatcgatag aagagtgcga ccaaattgaa   5700
gaacttctcg gcgacgacct gaaaggtgac aaggatgctt cgttgaccga tatgaattac   5760
tttgagttct cagaagactt cttagcctct gtcgaggagc cgcctttcgc tggattgcga   5820
ggaggtagca agaacgtcgc gattttggcg attttggaat acgtgcataa tttgtttcgc   5880
attgtcgcaa gcaagtgttc gaaacgacct ttatttcttg ctttcgccga actctcaagc   5940
gcccttattg agaaatttaa ggaggttttc cctcgtaaga gccagctcgt cgctatcgtg   6000
cgcgagtata ctcagagatt cctccgaagt cgcatgcgtg cgttgggttt gaataacgag   6060
ttcgtggtaa aatctttcgc cgatttgcta cccgcattaa tgaagcggaa ggtttcaggt   6120
tcgttcttag ctagtgttta tcgcccactt agaggtttct catatatgtg tgtttcagcg   6180
gagcgacgtg aaaagttttt tgctctcgtg tgtttaatcg ggttaagtct ccctttcttc   6240
gtgcgcatcg taggagcgaa agcgtgcgaa gaactcgtgt cctcagcgcg tcgcctttat   6300
gagcgtatta aaatttttct aaggcagaag tatgtctctc tttctaattt cttttgtcac   6360
ttgtttagct ctgacgttga tgacagttcc gcatctgcag ggttgaaagg tggtgcgtcg   6420
cgaatgacgc tcttccacct tctggttcgc cttgctagtg ccctcctatc gttagggtgg   6480
gaagggttaa agctactctt atcgcaccac aacttgttat ttttgtgttt tgcattggtt   6540
gacgatgtga acgtccttat caaagttctt gggggtcttt ctttctttgt gcaaccaatc   6600
ttttccttgt ttgcggcgat gcttttacaa ccggacaggt ttgtggggta ttccgagaaa   6660
cttgttacag cgtttgaatt tttcttaaaa tgttcgcctc gcgcgcctgc actactcaaa   6720
gggttttttg agtgcgtggc gaacagcact gtgtcaaaaa ccgttcgaag acttcttcgt   6780
tatttcgtga ggatgctcaa acttcgaaaa gggcgagggt tgcgtgcgga tggtaggggt   6840
ctccatcggc agaaagccgt acccgtcata ccttctaatc gggtcgtgac cgacggggtt   6900
gaaagacttt cggtaaagat gcaaggagtt gaagcgttgc gtaccgaatt gagaatctta   6960
gaagatttag attctgccgt gatcgaaaag ctcaatagac gcagaaatcg tgacactaat   7020
gacgacgaat ttacgcgccc tgctcatgag cagatgcaag aagtcaccac tttctgttcg   7080
aaagccaact ctgctggttt ggccctggaa agggcagtgc ttgtggaaga cgctataaag   7140
tcggagaaac tttctaagac ggttaatgag atggtgagga aagggagtac caccagcgaa   7200
gaagtggccg tcgctttgtc ggacgatgaa gccgtggaag aaatctctgt tgctgacgag   7260
cgagacgatt cgcctaagac agtcaggata agcgaatacc taaataggtt aaactcaagc   7320
ttcgaattcc cgaagcctat tgttgtggac gacaacaagg ataccggggg tctaacgaac   7380
gccgtgaggg agttttatta tatgcaagaa cttgctcttt tcgaaatcca cagcaaactg   7440
```

-continued

```
tgcgcctact acgatcaact gcgcatagtc aatttcgatc gttccttagc accatgcagc   7500
gaagatgctc agctgtacgt acggaagaac ggctcaacga tagtgcaggg taaagaggta   7560
cgtttgcaca ttaaggattt ccacgatcac gatttcctgt ttgacggaaa aatttctatt   7620
aacaagcggc ggcgaggcgg aaacgtttta tatcacgaca acctcgcgtt cttggcgagt   7680
aatttgttct tagccggcta cccctttca aggagcttcg tcttcacgaa ttcgtcggtc   7740
gatattctcc tctacgaagc tccacccgga ggtggtaaga cgacgacgct gattgactcg   7800
ttcttgaagg tcttcaagaa aggtgaggtt tccaccatga tcttaaccgc caacaaaagt   7860
tcgcaggttg agatcctaaa gaaagtggag aaggaagtgt ctaacattga atgccagaaa   7920
cgtaaagaca agagatctcc gaaaaagagc atttacacca tcgacgctta tttaatgcat   7980
caccgtggtt gtgatgcaga cgttcttttc atcgatgagt gtttcatggt tcatgcgggt   8040
agcgtactag cttgcattga gttcacgagg tgtcataaag taatgatctt cggggatagc   8100
cggcagatcc actacattga aaggaacgaa ttggacaagt gtttgtatgg ggatctcgac   8160
aggttcgtgg acctgcagtg tcgggtttat ggtaatattt cgtaccgttg tccatgggat   8220
gtgtgcgctt ggttaagcac agtgtatggc aacctaatcg ccaccgtgaa gggtgaaagc   8280
gaaggtaaga gcagcatgcg cattaacgaa attaattcag tcgacgattt agtccccgac   8340
gtgggttcca cgtttctgtg tatgcttcag tcggagaagt tggaaatcag caagcacttt   8400
attcgcaagg gtttgactaa atttaacgtt ctaacggtgc atgaggcgca aggtgagacg   8460
tatgcgcgtg tgaaccttgt gcgacttaag tttcaggagg atgaaccctt taaatctatc   8520
aggcacataa ccgtcgctct ttctcgtcac accgacagct taacttataa cgtcttagct   8580
gctcgtcgag gtgacgccac ttgcgatgcc atccagaagg ctgcggaatt ggtgaacaag   8640
tttcgcgttt ttcctacatc ttttggtggt agtgttatca atctcaacgt gaagaaggac   8700
gtggaagata acagtaggtg caaggcttcg tcggcaccat tgagcgtaat caacgacttt   8760
ttgaacgaag ttaatcccgg tactgcggtg attgattttg gtgatttgtc cgcggacttc   8820
agtactgggc cttttgagtg cggtgccagc ggtattgtgg tgcgggacaa catctcctcc   8880
agcaacatca ctgatcacga taagcagcgt gtttagcgta gttcggtcgc aagcgattcc   8940
gcgtagaaaa ccttctctac aagaaaattt gtattcgttt gaagcgcgga attataactt   9000
ctcgacttgc gaccgttaca catctgcttc aatgttcgga gaggctatgg cgatgaactg   9060
tcttcgtcgt tgcttcgacc tagatgcctt ttcgtccctg cgtaatgatg tgattagtat   9120
cacacgttca ggcatcgaac aatggctgga gaaacgtact cctagtcaga ttaaagcatt   9180
aatgaaggat gttgaatcgc ctttggaaat tgacgatgaa atttgtcgtt ttaagttgat   9240
ggtgaagcgt gacgctaagg tgaagttaga ctcttcttgt ttaactaaac acagccccgc   9300
tcaaaatatc atgtttcatc gcaagagcat taatgctatc ttctctccta tctttaatga   9360
ggtgaaaaac cgaataatgt gctgtcttaa gcctaacata aagtttttta cggagatgac   9420
taacagggat tttgcttctg ttgtcagcaa catgcttggt gacgacgatg tgtaccatat   9480
aggtgaagtt gatttctcaa agtacgacaa gtctcaagat gctttcgtga aggcttttga   9540
agaagtgatg tataaggaac tcggtgttga tgaagagttg ctggctatct ggatgtgcgg   9600
cgagcggtta tcgatagcta acactctcga tggtcagttg tccttcacga tcgagaatca   9660
aaggaagtcg ggagcttcga acacttggat tggtaactct ctcgtcactt tgggtatttt   9720
aagtctttac tacgacgtta gaaatttcga ggcgttgtac atctcgggcg atgattcttt   9780
aatttttct cgcagcgaga tttcgaatta tgccgacgac atatgcactg acatgggttt   9840
```

-continued tgagacaaaa tttatgtccc caagtgtccc gtacttttgt tctaaatttg ttgttatgtg 9900
tggtcataag acgtttttg ttcccgaccc gtacaagctt ttcgtcaagt tgggagcagt 9960
caaagaggat gtttcaatgg atttcctttt cgagactttt acctccttta aagacttaac 10020
ctccgatttt aacgacgagc gcttaattca aaagctcgct gaacttgtgg ctttaaaata 10080
tgaggttcaa accggcaata ccaccttggc gttaagtgtg atacattgtt tgcgttcgaa 10140
tttcctctcg tttagcaagt tgtatcctcg cgtgaaggga tggcaggttt tttacacgtc 10200
ggttaagaaa gcgcttctca agagtgggtg ttctctcttc gacagtttca tgaccccttt 10260
tggtcaggct gtcatggttt gggatgatga gtagcgctaa cttgtgcgca gtttctttgt 10320
tcgtgacata caccttgtgt gtcaccgtgc gtttataatg aatcaggttt tgcagtttga 10380
atgtttgttt ctgctgaatc tcgcggtttt tgctgtgact ttcattttca ttcttctggt 10440
cttccgcgtg attaagtctt ttcgccagaa gggtcacgaa gcacctgttc ccgttgttcg 10500
tggcgggggt ttttcaaccg tagtgtagtc aaaagacgcg catatggtag ttttcggttt 10560
ggactttggc accacattct ctacggtgtg tgtgtacaag gatggacgag tttttcatt 10620
caagcagaat aattcggcgt acatccccac ttacctctat ctcttctccg attctaacca 10680
catgactttt ggttacgagg ccgaatcact gatgagtaat ctgaaagtta aaggttcgtt 10740
ttatagagat ttaaaacgtt gggtgggttg cgattcgagt aacctcgacg cgtaccttga 10800
ccgtttaaaa cctcattact cggtccgctt ggttaagatc ggctctggct tgaacgaaac 10860
tgtttcaatt ggaaacttcg gggcactgt taagtctgag gctcatctgc cagggttgat 10920
agctctcttt attaaggctg tcattagttg cgcggagggc gcgtttgcgt gcacttgcac 10980
cggggttatt tgttcagtac ctgccaatta tgatagcgtt caaaggaatt tcactgatca 11040
gtgtgtttca ctcagcggtt atcagtgcgt atatatgatc aatgaacctt cagcggctgc 11100
gctatctgcg tgtaattcgg ttggaaagaa gtccgcaaat ttggctgttt acgatttcgg 11160
tggtgggacc ttcgacgtgt ctatcatttc ataccgcaac aatactttg ttgtgcgagc 11220
ttctggaggc gatctaaatc tcggtggaag ggatgttgat cgtgcgtttc tcacgcacct 11280
cttctcttta acatcgctgg aacctgacct cactttggat gtctcgaatc tgaaagaatc 11340
tttatcaaaa acggacgcag agatagttta cactttgaga ggtgtcgatg gaagaaaaga 11400
agacgttaga gtaaacaaaa acattcttac gtcggtgatg ctcccctacg tgaacagaac 11460
gcttaagata ttagagtcaa ccttaaaatc gtatgctaag agtatgaatg tgagtgcgcg 11520
agttaagtgc gatttagtgc tgataggagg atcttcatat cttcctggcc tggcagacgt 11580
actaacgaag catcagagcg ttgatcgtat cttaagagtt tcggatcctc gggctgccgt 11640
ggccgtcggt tgcgcattat attcttcatg cctctcagga tctgggggt tgctactgat 11700
cgactgtgca gctcacactg tcgctatagc ggacagaagt tgtcatcaaa tcatttgcgc 11760
tccagcgggg gcaccgatcc ccttttcagg aagcatgcct ttgtacttag ccagggtcaa 11820
caagaactcg cagcgtgaag tcgccgtgtt tgaaggggag tacgttaaat gccctaagaa 11880
cagaaagatc tgtggagcaa atataagatt ttttgatata ggagtgacgg gtgattcgta 11940
cgcacccgtt accttctata tggatttctc catttcaagc gtaggagccg tttcattcgt 12000
ggtgagaggt cctgagggta agcaagtgtc actcactgga actccagcgt ataacttttc 12060
gtctgtggct ctcggatcac gcagtgtccg agaattgcat attagtttaa ataataaagt 12120
ttttctcggt ttgcttctac atagaaaggc ggatcgacga atacttttca ctaaggatga 12180
agcgattcga tacgccgatt caattgatat cgcggatgtg ctaaaggaat ataaaagtta 12240

```
cgcggccagt gccttaccac cagacgagga tgtcgaatta ctcctgggaa agtctgttca  12300
aaaagtttta cggggaagca gactggaaga aatacctctc taggagcata gcagcacact  12360
caagtgaaat taaaactcta ccagacattc gattgtacgg cggtagggtt gtaaagaagt  12420
ccgatttcga atcagcactt cctaattctt ttgaacagga attaggactg ttcatactga  12480
gcgaacggga agtgggatgg agcaaattat gcggaataac ggtggaagaa gcagcatacg  12540
atcttacgaa tcccaaggct tataaattca ctgccgagac atgtagcccg gatgtaaaag  12600
gtgaaggaca aaaatactct atggaagacg tgatgaattt catgcgttta tcaaatctgg  12660
atgttaacga caagatgctg gcggaacagt gttggtcgct gtccaattca tgcggtgaat  12720
tgatcaaccc agacgacaaa gggcgattcg tggctctcac ctttaaggac agagacacag  12780
ctgatgacac gggtgccgcc aacgtggaat gtcgcgtggg cgactatcta gtttacgcta  12840
tgtccctgtt tgagcagagg acccaaaaat cgcagtctgg caacatctct ctgtacgaaa  12900
agtactgcga atatatcagg acctacttag ggagtacgga cctgtttttc acagcgccgg  12960
acaggattcc gttacttacg ggcatcctgt acgatttttg taaggaatac aacattttct  13020
actcgtcata taagagaaac gtcgataatt tcagattctt cttggcaaat tatatgcctt  13080
tgatatctga cgtctttgtc ttccagtggg taaaacccgc gccggatgtt cggctgcttt  13140
ttgagttaag tgcagcggaa ctaacgctgg aggttcccac actgagtttg atagattctc  13200
aagttgtggt aggccatatc ttaagatacg tagaatccta cacatcagat ccagccatcg  13260
acgcgttaga agacaaactg gaagcgatac tgaaaagtag caatccccgt ctatcgacag  13320
cgcaactatg ggttggtttc ttttgttact atggtgagtt tcgtacggct caaagtagag  13380
tagtgcaaag accaggcgta tacaaaacac ctgactcagt gggtggattt gaaataaaca  13440
tgaaagatgt tgagaaattc ttcgataaac ttcagagaga attgcctaat gtatctttgc  13500
ggcgtcagtt taacggagct agagcgcatg aggctttcaa aatatttaaa aacggaaata  13560
taagtttcag acctatatcg cgtttaaacg tgcccagaga gttctggtat ctgaacatag  13620
actacttcag gcacgcgaat aggtccgggt taaccgaaga agaaatactc atcctaaaca  13680
acataagcgt tgatgttagg aagttatgcg ctgagagagc gtgcaatacc ctacctagcg  13740
cgaagcgctt tagtaaaaat cataagagta atatacaatc atcacgccaa gagcggagga  13800
ttaaagaccc attggtagtc ctgaaagaca ctttatatga gttccaacac aagcgtgccg  13860
gttgggggtc tcgaagcact cgagacctcg ggagtcgtgc tgaccacgcg aaaggaagcg  13920
gttgataagt tttcaatgaa actaaaaaac gaaaattact catcagttga cagcagccga  13980
ttaagcgatt cggaagtaaa agaagtgtta gagaaaagta aagaaagttt caaaagcgaa  14040
ctggcctcca ctgacgagca cttcgtctac cacattatat ttttcttaat ccgatgtgct  14100
aagatatcga cgagtgaaaa ggtgaagtac gttggtagtc atacgtacgt ggtcgacgga  14160
aaaacgtaca ccgttcttga cgcttgggta ttcaacatga tgaaaagtct cacgaagaag  14220
tacaaacgag tgaatggtct gcgtgcgttc tgttgcgcgt gcgaagatct atatctaacc  14280
gtcgcaccaa taatgtcaga acgctttaag actaaagccg tagggatgaa aggtttgcct  14340
gttggaaagg aatacttagg cgccgacttt ctttcgggaa ctagcaaact gatgagcgat  14400
cacgacaggg cggtctccat cgttgcagcg aaaaacgctg tcgatcgtag cgctttcacg  14460
ggtggggaga gaaagatagt tagtttgtat gatctaggga ggtactaagc acggtgtgct  14520
atagtgcgtg ctataataat aaacactagt gcttaagtcg cgcagaagaa aacgcttaat  14580
taacaatgaa gactaatctt tttctctttc tcatcttttc acttctccta tcattatcct  14640
```

-continued

```
cggccgaatt cagtaaagga gaagaacttt tcactggagt tgtcccaatt cttgttgaat  14700
tagatggtga tgttaatggg cacaaatttt ctgtcagtgg agagggtgaa ggtgatgcaa  14760
catacggaaa acttaccctt aaatttattt gcactactgg aaaactacct gttccatggc  14820
caacacttgt cactactttc tcttatggtg ttcaatgctt ttcaagatac ccagatcata  14880
tgaagcggca cgacttcttc aagagcgcca tgcctgaggg atacgtgcag gagaggacca  14940
tcttcttcaa ggacgacggg aactacaaga cacgtgctga agtcaagttt gagggagaca  15000
ccctcgtcaa caggatcgag cttaagggaa tcgatttcaa ggaggacgga aacatcctcg  15060
gccacaagtt ggaatacaac tacaactccc acaacgtata catcatggcc gacaagcaaa  15120
agaacggcat caaagccaac ttcaagaccc gccacaacat cgaagacggc ggcgtgcaac  15180
tcgctgatca ttatcaacaa aatactccaa ttggcgatgg ccctgtcctt ttaccagaca  15240
accattacct gtccacacaa tctgcccttt cgaaagatcc caacgaaaag agagaccaca  15300
tggtccttct tgagtttgta acagctgctg ggattacaca tggcatggat gaactataca  15360
aacatgatga gctttaggcc ggcctaaact gttcctgaat agaaccattg gcaaacgtgg  15420
gatcccgtca gggtatgagt tcctcggggc agattttcta actgcgacca gcgtgtgttt  15480
gaacgatcac gaaaaagcta tcgtactaca ggcctcaaga gctgccattg atagagcagt  15540
ctcttcgtcg gtcgacggga agatcgtcag tcttttcgac ctcggtcgtc ttagttaaca  15600
cagttactaa ggttccattt tattattgca ttgtttttca tttagtgtaa tcgtacttga  15660
gttctaatcc tgcaggctat ggagttgatg tccgacagca accttagcaa cctggtgata  15720
accgacgcct ctagtctaaa tggtgtcgac aagaagcttt tatctgctga agttgtaaaa  15780
atgttggtgc agaaaggggc tcctaacgag ggtatagaag tggtgttcgg tctactcctt  15840
tacgcactcg cggcaagaac cacgtctcct aaggttcagc gcgcagattc agacgttata  15900
ttttcaaata gtttcggaga gaggaatgtg gtagtaacag agggtgacct taagaaggta  15960
ctcgacgggt gtgcgcctct cactaggttc actaataaac ttagaacgtt cggtcgtact  16020
ttcactgagg cttacgttga cttttgtatc gcgtataagc acaaattacc ccaactcaac  16080
gctgcggcgg aattggggat tccagctgaa gattcgtact tagctgcaga ttttctgggt  16140
acttgcccga agctctctga attacagcaa agtaggaaga tgttcgcgag tatgtacgct  16200
cttaaaactg aaggtggagt ggtaaatacg ccagtgagca atctgcgtca gctaggtaga  16260
agggaagtta tgtaatggaa gattacgaag aaaaatccga atcgctcata ctgctacgca  16320
cgaatctgaa cactatgctt ttagtggtca agtccgatgc tagtgtagag ctgcctaaac  16380
tactaatttg cggttactta cgagtgtcag gacgtgggga ggtgacgtgt tgcaaccgtg  16440
aggaattaac aagagatttt gagggcaatc atcatacggt gatccgttct agaatcatac  16500
aatatgacag cgagtctgct tttgaggaat tcaacaactc tgattgcgta gtgaagtttt  16560
tcctagagac tggtagtgtc ttttggtttt tccttcgaag tgaaaccaaa ggtagagcgg  16620
tgcgacattt gcgcaccttc ttcgaagcta acaatttctt ctttggatcg cattgcggta  16680
ccatggagta ttgtttgaag caggtactaa ctgaaactga atctataatc gattcttttt  16740
gcgaagaaag aaatcgttaa gatgagggtt atagtgtctc cttatgaagc tgaagacatt  16800
ctgaaaagat cgactgacat gttacgaaac atagacagtg gggtcttgag cactaaagaa  16860
tgtatcaagg cattctcgac gataacgcga gacctacatt gtgcgaaggc ttcctaccag  16920
tggggtgttg acactgggtt atatcagcgt aattgcgctg aaaaacgttt aattgacacg  16980
gtggagtcaa acatacggtt ggctcaacct ctcgtgcgtg aaaaagtggc ggttcatttt  17040
```

tgtaaggatg aaccaaaaga gctagtagca ttcatcacgc gaaagtacgt ggaactcacg 17100
ggcgtgggag tgagagaagc ggtgaagagg gaaatgcgct ctcttaccaa aacagtttta 17160
aataaaatgt ctttggaaat ggcgttttac atgtcaccac gagcgtggaa aaacgctgaa 17220
tggttagaac taaaattttc acctgtgaaa atctttagag atctgctatt agacgtggaa 17280
acgctcaacg aattgtgcgc cgaagatgat gttcacgtcg acaaagtaaa tgagaatggg 17340
gacgaaaatc acgacctcga actccaagac gaatgttaaa cattggttaa gtttaacgaa 17400
aatgattagt aaataataaa tcgaacgtgg gtgtatctac ctgacgtatc aacttaagct 17460
gttactgagt aattaaacca acaagtgttg gtgtaatgtg tatgttgatg tagagaaaaa 17520
tccgtttgta gaacggtgtt tttctcttct ttatttttaa aaaaaaataa aaaaaaaaaa 17580
aaagaagc 17588

<210> SEQ ID NO 8
<211> LENGTH: 1276
<212> TYPE: DNA
<213> ORGANISM: V. vinifera

<400> SEQUENCE: 8
atttttttta attaataaaa tattttcttc cattaatttg atattataaa tatataacta 60
attttcatat ggacaattca tttaaatttt aaaaaaatta ttcaatttta aaatttttat 120
accagttata attttcttaa acaaatgatg actttatggt agttggatga agttcacatt 180
tgtggaaaca taaaaaacag ttaagaaaac acacaaaaaa ggaaaagaca acatgaaaaa 240
taatctatta tttgaatagt gaaaaaaaat aatgaaaaca catttttatt gttctaaaaa 300
aagtgatttt tgaaaacaca aaaaatacaa aaaaaaaaaa aatcatactt cctttctcaa 360
acaagttttt tgtatttttt attttttcaa gaacagaaaa cattgaaaac accaccaaac 420
aaccctttgt ttcttaagag aagggtaata tggtaaactt gaaacgttag gacggttggt 480
ggggtatcta taattgaagt aaacgtcctg aagtgcagtt caccacaaat aaatacatcc 540
tgtattatta tttatatata tatatatata aaaacctgaa ttatgtataa ataattaata 600
gcaaaatttt tgaaccgaca aaaataaaat gatgctccat tgtctcgtat tctttttctt 660
gcttctttat aaacacgcat atgtaatatt tcttttattg aaaaaaaccc ccttagggag 720
agcgtgtctg tacttttgtt tatttaccca tttataaact gtgtggtatt aaaaggatta 780
accattagta ttttgtacta atagaggttt aataattttg taattgtaaa aatatatact 840
tattttatta aaaatatagc tatcatcaca tgaattaata atttaagatt aggggtccca 900
tttttgaaga aaaataaatg gtgagagtac aacagaacag aagtttgaat aataataata 960
agaaaaaata aaatgcgtgg aaaggagtca acgaggcaga gtaaaagcgg tctaaaaatg 1020
ggaaatggga tttattacaa ttgggaacgt gtcgaaatga tgagttgaac ttgcacaagt 1080
gtaaggcagc gtccaaattg cggataaggc cgatcctccc aacttcactc tataaagacc 1140
cccattttgc attcatctcc ccgcagactc actcctcact cttccttctt ctttctcaca 1200
aacaacacag aggagaaaat ccatttagat ttagtggaag aagaggcata cagtaaaaaa 1260
aaataattag cctatg 1276

<210> SEQ ID NO 9
<211> LENGTH: 2908
<212> TYPE: DNA
<213> ORGANISM: V. vinifera
<220> FEATURE:
<221> NAME/KEY: misc_feature -continued
<222> LOCATION: (728)..(739)
<223> OTHER INFORMATION: n is a, c, g, or t

<400> SEQUENCE: 9

```
catggaatgt aaagtaattt ttattttaaa taaatataaa aaaattgaaa aataatattt     60
cattttata ttattttaca aattaaattt aagcatcaca taaaatgtct tattagatat    120
ataataggaa aacataatgg aaaataattt gttttgagta aatatcatcg tcatagaaga    180
cattaaatgg aaagcatttc ttttttatct tcacacattt tcgaggcatg cttggcggat    240
gggaaaattt gaggtggttt tccatgttca aaacgttgag aaactctagg aacaccaaac    300
tatataaaag gcaaaaggtt agaaaatgga ttgaaattcg attcggaaaa aatcaagggg    360
gatttttcta gttttccttg tgataggccc tccaatcaag gaaaatttgt ctagattaag    420
gagaattcat ggaagatgag aaaattatgg tgtttggcta tacgattagc ccacaactta    480
gcctatgttt gtttcttaaa atacttgaaa gaaattacaa aataaaaata aaaaaagact    540
taaaattaat aaaattattt ttatttcaaa ttcattttac ttttttttat ataaaaaatt    600
aataatttaa aatacataat tttaattata tttacctttt tttttatata tttttcata    660
ataaaccaaa tatataaaaa caaaatcagt ttttgaacaa ttttttact taaaaaaatg    720
ataaaaannn nnnnnnnnna gaagtgttta gtatttttac ttaaaataaa tttattttat    780
ttttaaattc atgtattata acttatcaca ttttaaaaaa tgattttttta tttgtatagt    840
atatagtaaa gataatttaa aattgctctt tctttaaaaa ataaaaaaaaa taaaaaaata    900
aaaaataaaa acaataaaaa ttaatgatgc attacaacta actactccaa aaaaaaaaaa    960
aaaaaaaaaa aagtaaagaa taaaaagttc aagcttggtt ccatccatgc tttcgtgcat   1020
gcaccactct ttaaacaagg cgccaccgtt aattcatacc aatttttaaa tccaaaaaaa   1080
aataataata ataaataaat aaagaaggtc aacatgttca ttatttattc gatttataat   1140
agttagagag agagatggcc gattgcatta gtgtttctgg ggcggaggac cacgcctcta   1200
ttattgaaca aaaacaatca cttttaggct gtcaggtaag aaactttact tatttattta   1260
tttaattttt cattattggt gggtcccacc taaaatttaa agtcaatcat tttttaataa   1320
aaaattttat taataattaa agaggtgtgt atttttagcc tttttttatac ccttgacccc   1380
ccacttttca atctgcccct ttttctcctc tctttctttt tttttttttt aaaaatatta   1440
ttttcttttt tttttttttt atttttttta aaaatctttt tatacattca aaatttttaa   1500
aaaatatttt aaaaactatt ctcaaaaaag atttttataa tatttcaaaa gtttgtttaa   1560
aattaaaatt ttttttaatt ttttttttata tttaaatatt tttttatttg tttatatttt   1620
tgtttttaaa aaagaaagtt catttatgaa aatcttaagt agtttttata ctaaacactt   1680
cttttaaatc tatgctcttt aaacctctat atatatatat atatatatat atatatatat   1740
aatatatata tttttttttat catattttaa taaaaatatc tttattcttt ttacaataaa   1800
actaataatt tcttttaaat cataaatata aatgttgaaa taattaaaat atttatgtca   1860
aaaataaatt atttttcaag taaaaatatg aaaaagttta aattcataat tacgaggatt   1920
atttcgtctt tttaagtata cgtggaaagt tcattgtcac gtgacataaa cattatcatt   1980
tatcatataa ttgtaaaaca aaacctcatc ttcaggcgtt aaacttgacg tccatggcaa   2040
gccgttatat tttgcaacgg tccaagacgc gacacgtttg ggacggcgtg aaggtaacag   2100
caaacacaaa ttaaaatttc ctttcacatt gacgtgccgt acccattatt tcttgaattt   2160
tcacataatt aattttcacc gtcaatttag taatttcctt tttattttct tttcattttc   2220
taaaaaaaaa aaaatcatta gtatataaaa acttttatgc aataatccgc tatcttcact   2280
```

cgaatttaaa gtttagtata taataatatt aaattataaa attttcaaaa gctcattaat 2340
tgttaaattt atgattaaaa gtgggtatta attttacaaa acacttttaa tctaaaaaat 2400
tagtttagaa aaaagtcaaa tgtttgataa attttaggaa cgcttttcaa acaaatattt 2460
atgattttac aatttttcta aaaatactag aaaaaataac atttttacta aaaacattaa 2520
tgggcgcagt ctaataaata ttatgacacc tacactaact tttttaaaat ttgttattaa 2580
tttatggtat tcaaagaaaa attgataagt tggtgtggaa atagtgattt cctaaaatga 2640
atgatgaagg ggtggagatt ataactggag tgaagaacat ccggcggaat atggagccca 2700
caggggaggg cgggattgga acggtataaa tgaaggcatt gagggagagg gagagacgcc 2760
ttcctcattg tcgaccttga ttttcttggg agactcaata ctcatacatt gaatgagtgt 2820
ctccactatt ctctgattct tttctggttc ttctttcatc tcttcatctc cttcattgtt 2880
gtactgcgtc cctctgctgc cagatatg 2908

<210> SEQ ID NO 10
<211> LENGTH: 2107
<212> TYPE: DNA
<213> ORGANISM: V. vinifera

<400> SEQUENCE: 10
aataaattta tttaatttaa tattttttaa aaataaattt atttaattta atatttaaaa 60
aaatatttta atttaatatt tttttaaata ctttaattta atttaatatt tttgaaaact 120
acttttattt aatttagtat ttttgaaaaa aaaaatatta aaaaaaaatt atttaactta 180
attttataaa atattttata tgtgttctta aatggtatat ttgtcaatta ctatttcatg 240
tccttcaact caatttgaag agttatatgg atcttttgtt aatttgggac cgtctaaccc 300
taaaagataa ttctcccgat ttttattagg tatattaaga ttttatcaga aaatgtattt 360
gggaatcggg tggaggaggc acacgtgggg tggctataac cgtacgaggg gttcaaggac 420
taagggcgcg aaaacccatc acctttccac gcaatagaaa gatgcgtcaa agacaatggg 480
agccgtagaa aaaaaccagg gcgacaatgg tttcagagga gtaaacccat caaatagtaa 540
ttgaaaaaac aaatggtcat tacaagaaaa aggaattttg gaacaaaaag gaattttgga 600
agaaaaagga agaggagacg gtggatacag gaggagaaaa gatgaataaa attataatgg 660
gggttgggta tagagaaagc ggtgatggtg aaaagcggtt ttgtgaaagg tacagtgaaa 720
ccatgggaag atgcggatgt gtgagccatt atgacatttt cgcggaaaca gaggccccat 780
tctcaaatca aaggacgact aatgaggatt gtgaaggctt tctactggta tataagggta 840
tccaaggctt tcttttacca ccaccccatt tgcgtttgct tctccatttg atctcttcgt 900
tcgttccttc tttcattttg atttctctcc cttgctcggc attcttcttc ttcttcttct 960
tcttggttct cccctcccac cgcaccccat ttcatttttc tagctttgcc tttcaaaggt 1020
atgtgttgtt tctgttactt ttctgcatag catttctgta atacaaatgc gtttttgtcc 1080
aatgcgctca gccgttgaat gtgatcccgt gaaagacagt acctaaaaag tcttgcttgt 1140
tataatgccc accagcaaag gagaaggccc acctttgcct gtacctgcta aattttccaa 1200
atctccaccc accgcctaag ctttcatctt tccatttttc tccttccaaa cggctctacc 1260
tttcttgggt tttacggcta tgtatggggt ttcttaaggg ctacggcctg tccatgcatg 1320
ggttagccta gaattttctt ttatggaaaa gtatttttta ttttatttac ttctgtcttg 1380
gcatgttatt ttggtgcagg ggattttgtc tgtaattaga aaaatcacct cccataagct 1440
ttgatccttt attttgtgcg aggataaggg gaacatattt tcaacttgat ttctcccacc 1500

-continued

```
aaccctgtgt tgcttacatc caccattctg gtctttctat aaatttccca cgtttcttcc   1560

attcctctat ctcctttcat ttttcattct ctagttgatt gtgatcaact cacctcttct   1620

ctaggtactc ctccccctct ctgttttctg aagatctcag tctgatcttc tcttcttctt   1680

ctcttcctcc tcctcctcct cttcttcttc tccttcttct tcttcttctt ccctttttatg   1740

tttgttttca gtgtttcagc ttctgtttca ggtgatattg ctctaaattt tttcatctcc   1800

cagttttggg tttggtagct gtaggtttcc gttgtcaaac agaattagat cttatgatag   1860

cttaatagtc tttgcattat ttattagagt tgattttagt tcaacaacat actagatttt   1920

atattattat tgataagtgt gaggtgtcca attttgaaat ttaaaccttt ctagatggtg   1980

gaatgctggt tggtcttgac tttcttctca ataagaagct ttggatgatt ttgatctgtt   2040

agttacagtt gtttctctta cgttgaaggt tgtctgaaat taggtaagaa cccagagagg   2100

agacatg                                                             2107


<210> SEQ ID NO 11
<211> LENGTH: 9
<212> TYPE: PRT
<213> ORGANISM: Artificial sequence
<220> FEATURE:
<223> OTHER INFORMATION: hemagglutinin epitope tag

<400> SEQUENCE: 11

Tyr Pro Tyr Asp Val Pro Asp Tyr Ala
1               5
```

CLOSTEROVIRUS VECTORS AND METHODS

CROSS REFERENCE TO RELATED APPLICATIONS

This is the U.S. National Stage of International Application No. PCT/US2009/032380, filed Jan. 29, 2009, which was published in English under PCT Article 21(2), which in turn claims the benefit of U.S. Provisional Application No. 61/063,305, filed Jan. 31, 2008, and No. 61/083,504, filed Jul. 24, 2008, both of which provisional applications are incorporated herein by reference in their entirety.

FIELD

The present disclosure relates to the field of closteroviruses and their use as gene delivery vehicles for plants.

BACKGROUND

Grapevines (*Vitis*) are a major global fruit crop with enormous economic and cultural significance, particularly *Vitis vinifera*, which is used for wine cultivation. A relatively small number of *V. vinifera* cultivars are used commercially to maintain consistency in the fruit as the plants are heterozygous and do not breed true. Thus, because so much of the commercial grape crop is dependent on these cultivars, which have limited diversity, disease resistance is of major concern. Classical breeding techniques to increase disease resistance generally erode fruit quality, making grapevines a prime candidate for genetic manipulation for improving disease resistance. However, the production of transgenic grapevines has proven difficult, as woody perennials, such as grapevines, are known to be recalcitrant to transformation, and the selection process required by *Agrobacterium*-mediated transformation is significantly more stringent due to out competition by the untransformed cells, leading to highly variable success rates (Mullins et al., *Meth. Mol. Bio.* 344:273-285, 1990); Bouquet et al., *Methods Mol. Biol.* 344:273-285, 2006). Thus, a need exists for reliable, efficient method for the delivery of genes to grapevines for disease treatments and the modification of grapevines for desired characteristics.

During the last two decades, viral vectors for the transient expression of the proteins in plants and animals became indispensable tools of molecular biology and biomedicine (Pogue et al., *Annu. Rev. Phytopathol.* 40: 45-74, 2002; Gleba et al., *Curr Opin Biotechnol* 18: 134-141, 1007). With the advent of RNA interference (RNAi) or RNA silencing, viral vectors were also developed for virus-induced gene silencing or VIGS (Godge et al., *Plant Cell Rep* 27(2):209-219, 2008; e-pub ahead of print, 2007). Taken together, an ability to rapidly overexpress or silence genes of interest made viral vectors important tools in functional genomics.

A number of plant viruses have been engineered into viral vectors, each with limitations and plant specificity. Most are suitable only for use in dicotyledonous herbaceous plants. By and large, icosahedral viruses are ill suited for accommodating foreign genes mostly due to the limited size of their capsids. In general, the elongated viruses have exhibited a better ability to tolerate recombinant genes and to express them to very high levels. Currently, the most commonly used vectors are those based on the rod-shaped Tobacco mosaic virus (TMV, genus Tobamovirus) (Pogue et al., *Annu. Rev. Phytopathol.* 40: 45-74, 2002; Gleba et al., *Curr Opin Biotechnol* 18: 134-141, 1007). These vectors are characterized by high expression levels but relatively low genetic stability, especially when it comes to large foreign inserts.

Another series of vectors is based on rod-shaped Tobacco rattle virus (TRV, genus Tobravirus) (Godge et al., *Plant Cell Rep* 27(2):209-219, 2008; e-pub ahead of print, 2007). Vectors derived from filamentous viruses are commonly based on Potato virus X (PVX, genus Potexvirus) (Chapman et al., *Plant J* 2: 549-557, 1992) and Tobacco etch virus (TEV, genus Potyvirus) (Dolja et al., *Proc. Natl. Acad. Sci. USA* 89: 10208-10212, 1992). TMV, TRV, and PVX vectors contain an expression cassette with a subgenomic RNA promoter, while TEV vectors use an alternative principle of protein expression based on a polyprotein processing. This latter feature provides the potyviral vectors with much higher genetic stability than that found in promoter-containing vectors (Dolja et al., *Virology* 252: 269-274, 1998).

Gene expression vectors based on Beet yellows virus (BYV, genus Closterovirus) have been developed (Hagiwara et al., *J. Virol.* 73: 7988-7993, 1999; Peremyslov et al., *Proc. Natl. Acad. Sci. USA* 96, 14771-14776, 1999). Although the levels of protein expression achievable for closteroviral vectors may be lower than those for TMV or TRV, these vectors have proved to be very stable genetically and capable of accommodating several expression cassettes based either on additional heterologous subgenomic RNA promoters or polyprotein processing. Such versatility of closteroviral vectors is most likely due to the large size of closteroviral genomes and presence of genes that dramatically increase genome replication and gene expression ability and possibly provide for increased fidelity of RNA copying (Dolja et al., *Virus Res.* 117: 38-51, 2006). Strong suppressors of RNAi (Reed et al., *Virology* 306: 203-209, 2003; Chiba et al., *Virology* 346: 7-14, 2006) and the leader proteinases of closteroviruses (Peng et al., *J. Virol.* 75(24), 12153-12160, 2001) are among the genes that ensure high genetic and evolutionary performance of closteroviruses and precondition their genomes for accommodating additional genes, viral or foreign.

One of the most critical characteristics of the viral vector is its host range that severely limits its potential utility for the desired crop plants. All of the vectors described above are able to infect only dicotyledonous herbaceous plants. In other words, the need to generate a viral vector for monocots or for woody crops such as grapevine dictates the need of using viruses that naturally infect such plants as a platform for vector development.

To date, very few viral vectors potentially suitable for woody plants have been developed, and data showing expression has typically been limited to a narrow range of model plants. One of these vectors is based on Apple latent spherical virus RNA 2 (ALSV, family Sequiviridae) (Li et al., *Arch. Virol.* 149: 1541-1558, 2004). Although the authors claim that ALSV vector was able to express the green fluorescent protein (GFP) by polyprotein processing upon mechanical inoculation to apple seedlings, no convincing experimental proof of such ability was presented in the paper. Similarly, no data is available to support recent claims of a 'universal' vector based on Tomato yellow leaf curl geminivirus, allegedly capable of systemically infecting a vast variety of plants from dicots to monocots to trees and vines (Peretz et al., *Plant Physiol.* 145(4):1251-1263, 2007). Another vector was developed using Grapevine virus A (GVA, a Vitivirus). Its ability to express a foreign protein was demonstrated in tobacco (Haviv et al., *J. Virol. Meth.* 132: 227-231, 2006) and remains unproven for grapevine. Another vector is based on *Citrus tristeza* virus (CTV), a closterovirus closely related to BYV (Folimonov et al., *Virology* 368(1):205-216, 2007). However, CTV is useful only in *Citrus* species, and its propagation involves cumbersome process of cycling in protoplasts prior to slash-inoculation of citrus trees with isolated virions. Accordingly, there exists a strong need for viral vectors suitable for transforming woody plants, particularly grapevines.

SUMMARY

The present disclosure relates to replication-competent plant gene transfer vectors comprising a nucleic acid encoding viral genes from Grapevine leafroll-associated virus-2 (LR-2) selected from the group consisting of methyltransferase, RNA helicase, RNA-dependent RNA polymerase, and p24; leader proteases L1 and L2; and a heterologous polynucleotide operably linked to a promoter, wherein the heterologous polynucleotide is expressed in a plant cell; and wherein the vector is capable of infectious replication in the plant cell.

The present disclosure further encompasses conditionally-replicating plant gene transfer vectors comprising a nucleic acid encoding viral genes from Grapevine leafroll-associated virus-2 (LR-2) selected from the group consisting of methyltransferase, RNA helicase, RNA-dependent RNA polymerase, and p24; leader proteases L1 and L2, wherein at least one leader protease is inactivated such that the vector cannot infectiously replicate independently; and a heterologous polynucleotide operably linked to a promoter, wherein the heterologous polynucleotide is expressed in a plant cell.

Optionally, vectors provided herein may also include one or more viral genes from Grapevine leafroll-associated virus-2 (LR-2) that are involved in virion assembly and/or transport within plants. Such genes include for instance p6, Hsp70h, p63, CPm, CP and p19. In particular embodiments, all of these genes are included in a vector, thereby facilitating systemic infection. Such a vector may be referred to as a full-length vector; examples of such are described herein.

The heterologous polynucleotide in the described vectors may encode one or more of a reporter molecule, a selectable marker, or a therapeutic gene, which may encode a desired protein, such as to improve the nutritional or aesthetic properties of the plant or a disease resistance gene, which may be antifungal, antibacterial or antiviral. The therapeutic gene may be for the treatment of Pierce's Disease, such as a polynucleotide which triggers viral induced gene silencing or encodes a lysozyme polypeptide.

The leader proteases may be L1 and/or L2 from LR-2. The leader proteases (e.g., SEQ ID NOs: 4 or 6) may be encoded by SEQ ID NO: 3 and/or SEQ ID NO: 5. One or both of the leader proteases may be inactivated by substitution, insertion, partial deletion or complete disruption of the coding sequence for the leader protease in the vector.

The vector may further comprise a T DNA sequence for the transformation of a plant cell. The vector may comprise a beet yellows virus or other related closterovirus promoter or a native LR-2 promoter. More than one vector may be introduced into the plant, such as a vector encoding a therapeutic gene and a vector encoding the p24 RNAi suppressor.

A plant cell or plant comprising a vector described herein is also contemplated, such as a grapevine cell or grapevine.

Also provided are methods for producing the described vectors, comprising culturing a cell comprising the vector and recovering vector from the cell or medium in which the cell is grown. The vector may optionally be in a plasmid, such as a plasmid suitable for bacterial amplification and/or a binary plasmid suitable for agroinoculation.

Another embodiment is a method for expressing a heterologous gene in a plant cell comprising introducing the vector of the present invention into the plant cell. In one embodiment, the plant cell is a grapevine cell. In another embodiment, the vector is introduced by agroinoculation.

Another embodiment is a method for expressing a heterologous gene in a plant cell comprising introducing a replication-competent vector into the plant cell such that the vector subsequently replicates and infects at least one additional plant cell. The method further comprises the systemic infection of a plant structure selected from the group consisting of tissue, leaf, steam, root, fruit, seed or entire plant.

Another embodiment is a method for inducing disease resistance comprising introducing the vector of the present invention into a plant cell. The vector may be introduced more than one time. The vector may comprise a heterologous polynucleotide encoding a gene that confers resistance to the disease. Such heterologous polynucleotide may be, for example, a polynucleotide which triggers viral induced gene silencing, a Run1 polynucleotide, or encodes a lysozyme polypeptide.

Another embodiment is a method for treating or preventing Pierce's Disease or powdery mildew in a grapevine comprising introducing into a grapevine cell a vector of the present invention. The vector may be introduced by agroinoculation and may be introduced more than one time.

Another embodiment is a method for modifying the aesthetic properties, such as taste and aroma of the juice, or enhancing the nutritional or other agricultural characteristic of a plant comprising introducing the vector of the present invention into a plant cell.

Another embodiment is a method for making a transgenic plant comprising introducing the vector of the present invention into a plant cell, culturing the plant cell under conditions that promote growth of a plant, wherein the heterologous gene is expressed in the transgenic plant. The transgenic plant may be a grapevine.

The foregoing and other features and advantages will become more apparent from the following detailed description of several embodiments, which proceeds with reference to the accompanying figures.

BRIEF DESCRIPTION OF THE DRAWINGS

(FIG. 1A) Genes are designated in accord with the encoded proteins: (FIG. 1B) LR-2 CP promoter, a natural LR-2 promoter driving expression of CP gene; ER-GFP, endoplasmic reticulum-targeted green fluorescent protein; BYV CP promoter, an engineered heterologous promoter derived from Beet yellows virus where it drives expression of CP gene; Pac I and Fse I, engineered sites for corresponding restriction endonucleases. (FIG. 1C) From left, clockwise: 35S, 35S RNA polymerase II promoter derived from *Cauliflower mosaic* virus (arrow); ~17, 500 nts, the ~17, 500-nucleotide-long, full-length cDNA clone of LR-2 tagged by insertion of ER-GFP (rectangle, labeled ~17, 500 nts); RZ, a custom-designed ribozyme that promotes the autocatalytic release of the 3'-terminus of LR-r RNA upon transcription of the inserted DNA in plant cell nucleus (rectangle with an arrow, labeled RZ); NOS terminator of RNA polymerase II; Right border, recognition sequence where plasmid DNA is cleaved by *Agrobacterium* for transfer to the plant cell (curved arrow); Ori, origin of plasmid replication (arrow); $Kan^R$, gene for kanamycin resistance; Left border, recognition sequence where plasmid DNA is cleaved by *Agrobacterium* for transfer to the plant cell (curved arrow).

FIG. 6 Silencing of the GFP transgene by the viral vector LR-GFP in *N. benthamiana* line 16c. In the control, all cells are brightly fluorescent due to production of transgenic GFP. In the infected plants, bright fluorescent cells are those in which virus makes additional GFP. The areas of background fluorescence contain cells in which transgenic GFP was silenced due to virus-induced RNA interference.

FIG. 7 (FIG. 7A) Maximized expression of GFP using *Agrobacterium* introduced by sonication in a micropropagated Cabernet franc leaf. (FIG. 7B) A less susceptible leaf that, however, shows GFP expression in the vein. GFP is expressed directly from a binary vector engineered as shown in (FIG. 7C).

FIG. 14 Alignment of the nucleotide sequences of the *N. benthamiana*-derived (Nb; top lanes; SEQ ID NO: 1, nucleotides 4064-2163) and *V. vinifera*-derived (Vv, bottom lanes; SEQ ID NO: 7) variants of the GLRaV-2 vector. The nucleotides different in two isolates are shown in bold and underlined.

SEQUENCE LISTING

Figures 1A, 1B, 1C:
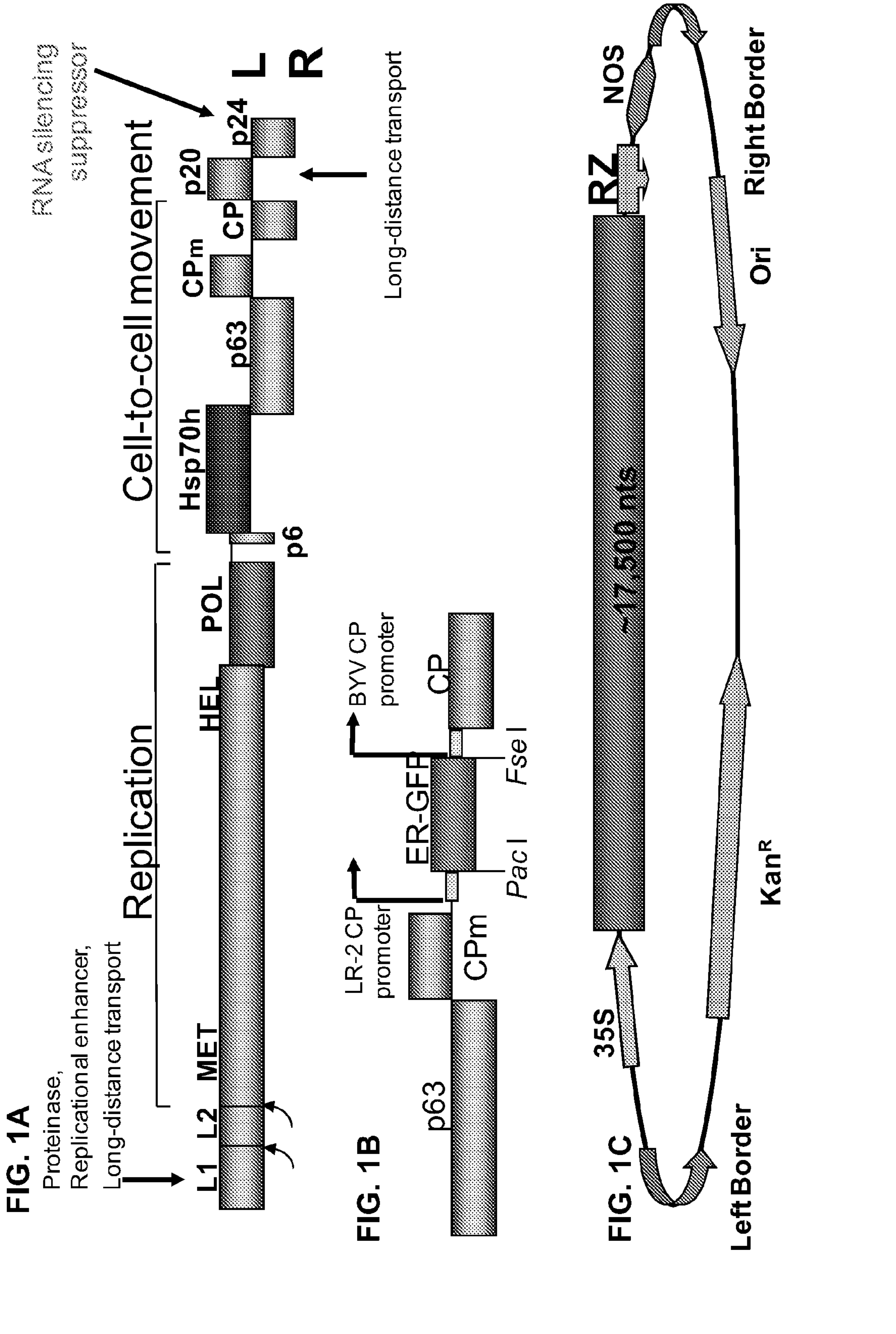
FIGS. 1A-1C are genetic maps of GLRaV-2 genome indicating the functions of the viral genes (FIG. 1A), cassette for recombinant gene expression (FIG. 1B), and binary vector containing the full-length GLRaV-2 genome with ER-GFP insert (FIG. 1C).

The nucleic and/or amino acid sequences listed herein and/or in the accompanying sequence listing are shown using standard letter abbreviations for nucleotide bases, and three letter code for amino acids, as defined in 37 C.F.R. §1.822. Only one strand of each nucleic acid sequence is shown, but the complementary strand is understood as included by any reference to the displayed strand. In the accompanying sequence listing:

SEQ ID NO: 1 is the nucleic acid sequence of p35S-LR-2/ERGFP, a full-length, Grapevine leafroll virus-2-derived gene expression and silencing vector containing a recombinant gene encoding ER-targeted GFP reporter. The sequence includes binary vector pCB301 (1-3305), and the entire viral expression cassette (3306-21957). The following features that are shown in FIG. 1C are also reflected in the sequence: 35S promoter (3306-4063), viral sequence (4064-21643) including GFP-reporter expressing cassette (18648-19439), heterologous BYV CP promoter (18440-19723), ribozyme (21644-21698) and NOS terminator (21705-21957).

SEQ ID NO: 2 is the nucleic acid sequence of MiniLR-GFP/GUS. SEQ ID NOs: 3 and 4 are the nucleotide and amino acid sequences of protease L1.

SEQ ID NOs: 5 and 6 are the nucleotide and amino acid sequences of protease L2.

SEQ ID NO: 7 is the nucleotide sequence of full-length, Grapevine leafroll-associated virus-2-derived gene expression and silencing vector containing a recombinant gene encoding ER-targeted GFP reporter (LR2-*Vitis*). All Grapevine leafroll-associated virus-2 nucleotide sequence corresponds to a consensus sequence of the viral isolate naturally present in Pinot Noir grapevine. Nucleotides distinct from those present in the original, *N. benthamiana*-derived virus (SEQ ID NO: 1) are highlighted in FIG. 14. The nucleotide sequences outside the viral expression cassette are the same as in SEQ ID NO: 1.

SEQ ID NO: 8 is a representative *V. vinifera* chromosome genomic sequence encompassing a putative phloem-specific promoter, AtSUC2 orthologous promoter (GSVIVT00002302001_VvSUC27_AF021810_Genomic), suitable for phloem-specific expression of the LR-2 vectors.

SEQ ID NO: 9 is a representative *V. vinifera* chromosome genomic sequence encompassing a putative phloem-specific promoter, AtAHA3 orthologous promoter (VV78X258876_VITISV_014422_AM487422_CAN64375_Genomic), suitable for phloem-specific expression of the LR-2 vectors.

SEQ ID NO: 10 is a representative *V. vinifera* chromosome genomic sequence encompassing a putative phloem-specific promoter, AtAsus1 orthologous promoter (VV78X051063_CAN82840_VITISV_024563_GI147856448_Genomic), suitable for phloem-specific expression of the LR-2 vectors.

SEQ ID NO: 11 is the amino acid sequence of the hemagglutinin epitope (HA) tag.

DETAILED DESCRIPTION

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). In order to facilitate review of the various embodiments of the invention, explanations of specific terms are provided herein.

The term “grapevine”, “grape plant” or “grapevine plant” refers to any plant of the genus *Vitis*, for example *V. vinifera, V. labrusca, V. riparia, V. rotundifolia, V. aestivalis*, or of the genus *Muscadinia*, and species thereof. The grapevine may be a scion, rootstock, cultivars or a hybrid plant. The term “grape” is the berry or fruit of the grapevine, which may be eaten whole or the juice extracted therefrom for drinking and/or fermentation into wine. Other edible portions of a grapevine include the leaves and the seeds.

Unless otherwise explained, all technical and scientific terms used herein have the same meaning as commonly understood by one of ordinary skill in the art to which this invention belongs. The singular terms “a,” “an,” and “the” include plural referents unless context clearly indicates otherwise. Similarly, the word “or” is intended to include “and” unless the context clearly indicates otherwise. Hence “comprising A or B” means including A, or B, or A and B. It is further to be understood that all base sizes or amino acid sizes, and all molecular weight or molecular mass values, given for nucleic acids or polypeptides are approximate, and provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including any explanations of terms, will control. In addition, the materials, methods, and examples are illustrative only and not intended to be limiting.

Overview of Several Embodiments

The present disclosure provides gene transfer vectors comprising at least the replication genes of grapevine leafroll-associated virus-2 (LR-2). LR-2 has been sequenced (Meng et al., *Virus Genes* 31:31-41, 2005) and functionally compared to other known closteroviruses (Dolja et al, *Virus Res.* 117(1):38-51, 2006). Both references are hereby incorporated by reference. The core viral genes of LR-2 include Met (methyltransferase), Hel (RNA helicase) and Pol (RNA-dependent RNA polymerase), while L1, L2, and p24, by comparison to homologous genes of BYV, play accessory roles in genome replication. Other genes may also be included in the present vector, such as p6, Hsp70h, p63, CPm, CP, and p19 (see, e.g., Peremyslov et al., *J. Virol.* 72:5870-5876, 1998, which is hereby incorporated by reference).

The present disclosure relates to vectors comprising the leader proteases, L1 and L2, and vectors with one or both leader proteases inactivated. One of skill in the art will instantly recognize that there are myriad ways in which a protease could be inactivated, and all such methods are contemplated herein. It has been shown previously that for a related closterovirus, BYV, the corresponding leader protease L-Pro is required for efficient RNA amplification and virus long-distance transport (Peng et al., *J. Virol.* 77, 2843-2849, 2003; Peng & Dolja, *J. Virol.* 74, 9766-9770, 2000). Interestingly, replacement of L-Pro by the proteases from other closteroviruses (Peng et al., *J. Virol.* 75(24), 12153-12160, 2001) or even from an animal arterivirus (Peng et al., *Virology* 294, 75-84, 2002) can rescue the RNA amplification, but not the transport function of the leader protease. The Grapevine leafroll-associated virus-2 (GLRaV-2) is a close BYV relative in the Closterovirus genus whose genetic organization is almost identical to that of BYV (Zhu et al., *J. Gen. Virol.* 79: 1289-1298, 1998). However, unlike BYV that possesses one leader protease, GLRaV-2 codes for two leader proteases, L1 and L2 (Meng et al., *Virus Genes* 31, 31-41, 2005; Peng et al., *J. Virol.* 75(24), 12153-12160, 2001) (FIG. 1A, top diagram). Herein is shown for the first time that L1 and L2 have complementary functions in establishment of the GLRaV-2 infection in the initially inoculated cells and systemic transport. Strikingly, overall contribution of L1 and L2 into virus infection is much more critical in a natural virus host, grapevine, compared to an experimental herbaceous host, *N. benthamiana*. Thus, using the properties of L1 and L2, vectors for the introduction of heterologous genes into grapevines may be constructed as replication-competent (comprising both L1 and L2) or conditionally-replicating (with one or both leader proteases inactivated).

Replication-competent vectors are those vectors that are capable of producing infectious virions without needing additional factors supplied in trans. Such vectors, after inoculation or transduction into a plant cell may produce infectious virions and infect other cells. Such vectors may be useful when systemic infection of a plant is desired, as the vector may spread beyond the originally transduced cell and increase overall transduction. For example, the vector may spread within a tissue, between tissues, throughout the plant or even between plants. For instance, the vector may infect an entire leaf, more than one leaf, one or more leaves and the stem or fruit of the plant, as well as the roots.

Conditionally-replicating vectors lack necessary viral factors for the production of infectious virions independently. The present disclosure encompasses vectors that have one or both leader proteases inactivated such that the vector is not capable of producing infectious virions and cannot infect additional cells after inoculation or transduction. Such vectors may be useful when spread of the vector is not desired, or when limited spread is beneficial. Such vectors may have increased safety as the spread of the vector as well as expression of the heterologous gene does not go beyond the original transduction.

In specific embodiments, the plant transformation vectors provided herein include one or more viral genes from Grapevine leafroll-associated virus-2 (LR-2) that are involved in virion assembly and/or transport within plants. Such genes include for instance p6, Hsp70h, p63, CPm, CP and p19. In particular embodiments, all of these genes are included in the vector, thereby facilitating systemic infection. Such a vector may be referred to as a full-length vector.

The entire LR-2 genome (or essentially all of the genome, or the equivalent thereof) may be included in the vector. The vector may comprise additional heterologous sequences, such as sequences that facilitate propagation or transformation. Such sequences may be control elements for agroinfection, such as a binary vector, which are well known in the art. The vector may have the nucleotide sequence of SEQ ID NO: 1 or SEQ ID NO: 2, either as provided herein or with different heterologous sequences replacing the reporter genes provided as examples (GFP and GUS). The leader proteases of the vector may be L1 (SEQ ID NO: 4) and/or L2 (SEQ ID NO: 6) from LR-2 and may be encoded by SEQ ID NO: 3 and 5, respectively. Further, a suppressor of RNA silencing may also be introduced with the vector. Such suppressors may be LR-2 p24 or p21 from Beet yellows virus (Chiba et al., *Virology* 346: 7-14, 2006).

The vector includes a heterologous polynucleotide operably linked to a promoter. The promoter may be a native LR-2 promoter, e.g. LR-2 CP promoter, or it may be a heterologous promoter, such as a promoter from other viruses that belong to genus Closterovirus, such as Beet yellows virus, e.g. BYV CP promoter, Beet yellow stunt virus, Carnation yellow fleck virus, *Citrus tristeza* virus, Mint virus 1, etc. Although CP promoter of these viruses normally provides highest expression levels, several additional promoters from these viruses might be useful. Many suitable promoters are known in the art. The heterologous polynucleotide may encode a reporter molecule, a selectable marker and/or a therapeutic gene. Examples of reporter molecules include fluorescent proteins, such as green fluorescent protein, luciferase, beta-galactosidase, beta-glucuronidase, and other reporter molecules known in the art. Examples of selectable markers also include antibiotic resistant markers, epitope tags useful for affinity purification and the like. Examples of therapeutic genes include those that confer resistance to a pathology or disease.

The present disclosure encompasses methods for inducing disease resistance in a plant or plant cell by introducing the plant gene expression vector of the present disclosure into the cell. Such diseases of grape plants include, but are not limited to fungal agents, bacterial agents, viral agents, parasites and environmental stress. Examples of fungal diseases include *Guignardia bidwellii* (black rot), *Plasmopara viticola* (downy mildew), *Erysiphe necator* (powdery mildew, formerly *Uncinula necator*), *Botrytis cinerea* (bunch rot), *Sclerotinia sclerotiorum* (Sclerotinia shoot rot), *Eutypia armenicae* (Eutypia dieback), *Elsinoe ampelina* (anthracnose), *Alternaria alternata* (alternia rot), *Pseudopezicula tetraspora, Cercospora brachypus, Sphaceloma ampelinum, Ascochyta* sp. *Aspergillus aculeatus, Cladosporium* spp., *Fusarium* spp., *Helminthosporium* spp., *Monilia* sp., *Stemphylium botryosumv, Pleospora tarda, Torula* sp., *Greeneria uvicola, Botryosphaeria stevensii, Diplodia mutila, Penicillium* spp., *Botryotinia fuckeliana, Anthostomella pullulans, Clostridium* spp., *Libertella blepharis, Lasiodiplodia theobromae, Rosellinia necatrix, Dematophora necatrix, Roesleria subterranea, Mycosphaerella personata, Pseudocercospora vitis, Isariopsis clavispora, Briosia ampelophaga, Phymatotrichopsis omnivora, Dematophora necatrix, Cristulariella moricola, Grovesinia pyramidalis, Cephalosporium spp., Phellinus igniarius, Stereum hirsutum, Physopella ampelopsidis*, and *Phompopsis viticola* (phomopsis leaf and cane spot disease).

Examples of bacterial diseases include *Xylella fastidiosa* (Pierce's disease), *Agrobacterium tumefaciens* (crown gall), *Pseudomonas syringae*, and *Xylophilus ampelinus* (bacterial blight).

Examples of viral diseases include grapevine leafroll-associated viruses, grapevine fanleaf virus, grapevine virus A, grapevine virus B, tomato ringspot, Rupestris stem pitting associated virus, tobacco ringspot, Arabis mosaic virus, Artichoke Italian latent virus, Alfalfa mosaic virus, Bratislava mosaic virus, Broad bean wilt virus, grapevine strawberry latent ringspot virus, tobacco necrosis virus, tobacco mosaic virus, grapevine chrome mosaic virus, petunia asteroid mosaic virus, and Tomato black ring virus.

Examples of pests include *Daktulosphaira vitifoliae, Lepidoptera, Otiorhynchus sulcatus, Tylenchulus semipenetrans, Xiphinema* spp., *Pratylenchus* spp., *Longidorus* spp., *Paratylenchus hamatus, Paratylenchus hamatus, Rotylenchulus* spp., *Criconemella xenoplax, Meloidogyne* spp., *Helicotylenchus* spp., *Paratrichodorus christiei*, and *Tylenchorhynchus* spp.

Examples of environmental stress include drought, heat stress, salt stress, iron deficiency, zinc deficiency, ozone, and environmental toxins. Alternatively, the present vector may be used to confer resistance to herbicides, fungicides, pesticides and viricides.

Pierce's disease (PD), caused by an infection by the bacterium *Xylella fastidiosa*, is of particular importance to growers of grape cultivars. The bacteria multiply in the plant xylem, causing blockage of water movement and the characteristic leaf blight or necrosis, particularly during heat or water stress. Management presently focuses on prevention of infection by targeting the insect carrier which transmits the bacteria from plant to plant during feeding. A number of insect vectors are known, including a variety of sharpshooters, such as the glassy winged sharpshooter. Many commercially important cultivars are susceptible to PD, thereby making control of this disease urgently needed.

Treatments for such diseases can include the expression of therapeutic proteins, such as the genes of pathogenic or infectious organisms or repression of host genes to mitigate an undesired response. Examples of therapeutic proteins include proteins that target the pathogenic organism or agent directly, such as chitinases, which degrade the protective fungal walls (e.g., Adams, *Microbiology* 150: 2029-2035, 2004), replicases, which inhibit replication (e.g. WO 98/052964), lysozymes, which attack bacterial walls, or genes that have been found in disease resistant plants. Lysozymes have been shown to have antibacterial properties, and may be effective against *Xyllela*. U.S. Appl. No. 20020104126, which is hereby incorporated by reference, shows that bovine lysozyme, which is active at a very low pH, may be expressed in tobacco plants and retain activity in in vitro tests. However, the feasibility of expressing lysozyme in woody plants, namely grapevines, or its effectiveness against *Xyllela* or treating PD was untested. The grapevine powdery mildew resistance gene, Run1, has been shown to confer resistance to susceptible *V. vinifera* when transferred through a pseudo-backcross strategy and delivery using a bacterial artificial chromosome (Barker et al., *Theor. Appl. Genet.* 111:370-377, 2005). Therefore, Run1 and other genes associated with disease resistance are suitable for use in the methods and constructs/vectors described herein.

Alternatively, the present vector can be used to induce RNA silencing (virus-induced gene silencing or VIGS) to repress undesired gene expression, such as expression of genes from pathogenic organisms or undesired host genes. VIGS is a phenomenon well known in the art as a mechanism used to examine the functions of plant genes (Godge et al., *Plant Cell Rep* 27(2):209-219, 2008; e-pub ahead of print, 2007). To induce VIGS, the vector may encode a portion of a nucleotide sequence from the targeted gene. The nucleotide sequence may be from any portion of the transcript expressed from the gene, including a protein coding region or untranslated sequences.

Another embodiment of the present disclosure is the use of the inventive vector to introduce genes that are involved in aesthetic modification of the edible portions of the transduced or transgenic plant, such as taste or aroma of the juice. Such edible portions include the roots, stems, leaves, flowers, seeds and/or fruit of the plant, or any edible substance derived therefrom. In particular, grapes, or the juice derived therefrom, may be modified such that agents that interact with the taste receptors to block or enhance certain tastes, such as bitterness, sweetness, sourness and the like. Alternatively, the agents enhance the aromatic compounds found in the grapes or juice. Such agents may be proteins, such as monellin, thaumatins, gustducin, terpenoids and other such proteins known in the art. For aesthetic modification, the vector of the present disclosure may be engineered to encode an aesthetic modifying molecule, such as a protein, and the vector is then used to transform a plant cell, which then expresses the molecule.

The methods and vectors of the present disclosure may also be used to introduce genes that are involved with the metabolic pathways of grapes (metabolomics) for the improvement of nutritional characteristics. For example, resveratrol, a polyphenolic compound (3,4',5-trihydroxystilbene) found in grapes, has been found to have certain health benefits, such as anti-cancer properties and association with a reduction in cardiovascular disease. Other compounds found in grapes with potential health benefits include phytonutrients such as quercetin, catechins, anthocyanins and proanthocyanidins. The sequencing of the pinot noir grape varietal as well as development of metabolic profiling techniques, such as nuclear magnetic resonance spectroscopic techniques, provide valuable information for developing genes suitable for use with the vectors and expression systems described herein. Additional genes of interest are involved in ripening, such the fib gene, as well as any aspect of plant growth, development, and agricultural production that may be desired.

The present disclosure encompasses methods for expressing a heterologous gene in a plant cell by introducing a described plant gene expression vector of into the cell. The plant gene transfer vector may be introduced into the plant cell by any of the methods known in the art, for example by vacuum infiltration, sonication, ballistically, calcium phosphate precipitation, electroporation, polyethylene glycol fusion, direct transformation (Lorz et al, *Mol. Genet.* 199: 179-182, 1985) and other methods. The vector may be introduced as an infectious viral particle or as a noninfectious nucleotide. One method is agroinoculation, for example, incorporating the vector into a binary plasmid with suitable control elements for expressing the vector in an *Agrobacterium* species, such as *A. tumefaciens, A. rhizogenes*, and *A. vitis*. Such methods are known in the art, such as those described in Leiser et al., *Proc. Natl. Acad. Sci. USA* 89:9136-9140, 1992 and Bouquet et al, *Methods in Mol. Bio.* 344: 273-285, *Agrobacterium Protocols*, $2^{nd}$ ed. vol. 2, Wang ed (2006), both of which are incorporated by reference. *Agrobacterium* may be introduced into entire micropropagated grapevine plants by means of vacuum infiltration or sonication. *Agrobacterial* strains engineered to express viral vector may be mixed with another strain engineered to express viral suppressor of RNAi in order to increase vector infectivity (Chiba et al., *Virology* 346: 7-14, 2006).

The vector may be introduced for stable expression or transient expression. Stable expression may be achieved by a variety of known methods, such as co-culturing embryonic grape tissue with *Agrobacterium* containing the vector using the methods of Bouquet et al. (*Methods Mol. Biol.* 344:273-285, 2006). Transient expression can also be achieved by known methods, such as the methods described in the Examples of the present application. Other methods include, but are not limited to, leaf infiltration, vacuum infiltration and bombardment of target tissues with DNA-coated particles.

The vector may also be applied to the grapevine or any part thereof through application of a solution containing the vector, such as by spraying. Such solutions contain the vector as DNA, DNA coated particles or contained with *Agrobacterium*, as well as salts and buffers. The solution may contain, for example, a phosphate buffer at 0.1 M, pH 7 or it may contain nicotine. Such formulations are well known in the art and may be used as suitable for the present methods. The solution may further contain an abrasive, such as carborundum, for example 500-mesh carborundum, kaolin or Celite® diatomaceous earth. The solution may also comprise a surfactant, such as Triton or Tween, which are well known in the art. The solution may be applied to the plant via swabbing, dripping, immersion, spraying or other means. See, e.g., *Graft transmissible diseases of grapevines*. Martelli ed. 1993, Rome, Italy, Food and Agriculture Organization of the United Nations publ.

The present disclosure further includes compositions comprising the vector(s) described herein. In addition to the vector and optionally other functional ingredients such as abrasives and/or surfactant, such compositions may include excipients suitable for introducing the vector into a plant cell, such as salts, e.g., magnesium chloride, and buffers, such as MES or phosphate, and are typically aqueous solutions. See, e.g., *Graft transmissible diseases of grapevines*. Martelli ed. 1993, Rome, Italy, Food and Agriculture Organization of the United Nations publ.

The vector may be applied, daily, monthly, seasonally, or annually. The vector may be applied during or prior to the onset of disease or the infestation of the disease carriers. For example, symptoms of disease may be read twice a year: late spring for leaf and cane deformations and necrosis and autumn for abnormal pigmentation and other deformities (*Graft transmissible diseases of grapevines*. Martelli ed. 1993, Rome, Italy, Food and Agriculture Organization of the United Nations publ). Upon identification of symptoms, the vector can by applied, such as by spraying with an abrasive-containing solution. Alternatively, the plants may be sprayed upon infestation with a known carrier of a disease, such as certain nematodes or grapevine leafhoppers, or upon certain weather conditions or seasons known to induce conditions favorable to a disease, such as wet weather and powdery mildew. Guidelines and indices for such conditions are well known in the art, such as the University of California Pest Management Guidelines, Statewide Integrated Pest Management Systems, available on the World Wide Web at.ipm.ucdavis.edu/PMG/r302101211.html (last accessed Jan. 27, 2008), which is hereby incorporated by reference. Further, the present vector may be applied with other known anti-disease agents, such as oils, fungicides and the like.

The present disclosure includes a method for transforming a plant comprising introducing the described plant gene transfer into the plant once or more than once. The vector may be introduced two, three, four, five, six, seven, eight, nine, ten or more than ten times to the plant. The plant may express the heterologous polynucleotide systemically or locally.

The plant cell may be grown into a transgenic plant, such as using the methods of Bouquet et al. (*Methods Mol. Biol.* 344:273-285, 2006). Alternatively, the plant cell may be part of a multicellular plant such that only a portion of the plant is transformed. For example, the root stock, the stem or the leaves may be transformed. The vector may be introduced prior to onset of disease to confer resistance, or it may be introduced after disease is observed to reduce or ameliorate the disease, to protect the remaining uninfected portions of the plant or to prevent the spread of the disease to other plants.

ADDITIONAL REFERENCES

Agranovsky et al., *Proc. Natl. Acad. Sci. U S A* 92(7), 2470-2473, 1995

Alzhanova et al., *Virology* 268(1), 192-200, 2000

Alzhanova, *EMBO J.* 20, 6997-7007, 2001

Alzhanova et al., *Virology* 359, 220-226, 2007

Barrett & Rawlings, *Biol. Chem.* 382, 727-733, 2001

Boyko et al., *Proc. Natl. Acad. Sci. U S A* 89, 9156-9160, 1992 de los Santos et al., *J. Virol.* 80, 1906-1914, 2006

Ding & Voinnet, *Cell* 130, 413-426, 2007

Donson et al., *Proc Natl Acad Sci U S A* 88: 7204-7208, 1991

Dougherty & Semler, *Microbiol. Rev.* 57(4), 781-822, 1993

Gabrenaite-Verkhovskaya et al., *J. Gen. Virol.* 89, 829-838, 2008

Gorbalenya et al., *FEBS Lett* 243, 103-114, 1989

Gorbalenya et al., *Virus Res.,* 117(1):17-37, 2006

Gorbalenya et al., *FEBS Lett.* 288(1-2), 201-5, 1991

Karasev, Annu. *Rev. Phytopathol.* 38, 293-324, 2000

Kasschau et al., *Virology* 228(2), 251-62, 1997

Koonin & Dolja, *Crit. Rev. Biochem. Mol. Biol.* 28(5), 375-430, 1993

Koonin & Dolja, *Virus Res* 117, 1-4, 2006

Lakatos et al., *EMBO J.* 25, 2768-2780, 2006

Lu et al., *Proc. Natl. Acad. Sci. U S A* 101, 15742-15747, 2004

Marillonnet et al., *Nat. Biotechnol.* 23: 718-723, 2005

Napuli et al., *J. Virol.* 77, 2377-2384, 2003

Ng & Falk, *Annu. Rev. Phytopathol.* 44, 183-212, 2006

Satyanarayana et al., *Proc. Natl. Acad. Sci. U S A* 101, 799-804, 2004

Satyanarayana et al., *Virology* 278(1), 253-265, 2000

Segers et al., *Eukaryot. Cell* 5, 896-904, 2006

Susaimuthu et al., *Virus Res.* 131, 145-151, 2008

Tian et al., *J. Gen. Virol.* 80, 1111-1117, 1999

Tijms et al., *J. Virol.* 81, 10496-10505, 2007

Torrance et al., *J. Mol. Biol.* 357, 1-8, 2005

Valli et al., *J. Virol.* 80, 10055-10063, 2006

Ziebuhr et al., *J. Virol.* 81, 3922-3932, 2007

Ziebuhr et al., *J. Gen. Virol.* 81, 853-879, 2000

The following examples are provided to illustrate certain particular features and/or embodiments. These examples should not be construed to limit the invention to the particular features or embodiments described.

EXAMPLES

Search for a local virus isolate. A survey of local vineyards was performed to determine if LR-2 is naturally present in Oregon, and vines were found that exhibited LR-2-like symptoms of early leaf reddening Immunoblot analysis was performed with the commercially-available LR-2 immunodetection kit (Bioreba AG, Reinach, Switzerland; Cat. No 120775) and custom antibodies generated using the LR-2 virions isolated from *N. benthamiana* as described below. RT-PCR analysis using the primers designed to amplify ~2 kb region of LR-2 genome containing viral capsid protein gene also demonstrated that the vines indeed contained the virus.

Molecular cloning and nucleotide sequencing. To facilitate accumulation and isolation of LR-2, material from infected vines was used to mechanically inoculate *N. benthamiana*. Purified virus particles were used to obtain viral RNA, amplify it by RT-PCR and clone the cDNA products into pBlueScript vector plasmid. The terminal sequences of the viral genome were cloned using RLM-RACE. A large number of the independent clones were sequenced to provide multiple coverage of the viral genome. The resulting consensus nucleotide sequence for the first time included the entire viral genome and contained exact 5'-terminal and 3'-terminal regions. Comparative analysis of this sequence revealed 99.9% identity with the previously published incomplete sequence of the New York LR-2 isolate over the regions of overlap (Zhu et al., *J. Gen. Virol.* 79: 1289-1298, 1998). A functional map of the ~16,500 nucleotides-long LR-2 genome is shown in FIG. 1A.

The initial inoculation of *N. benthamiana* with LR-2 was performed as described by Goszczynski et al. (*Vitis* 35:133-135, 1996). Subsequently, infected leaves of *N. benthamiana* were used for making inoculum for virus propagation on this experimental virus host. Routinely, 1 g of infected tissue was ground in 5 ml of 0.05 Na-phosphate buffer, pH 7.0, and used for manual inoculation of the new plants with the aid of carborundum.

RT-PCR amplification, cloning, and assembly of the full-length cDNA clone were performed as described in Peremyslov and Dolja (*Curr. Protocols Microbiol., "Cloning of Large Positive-Strand RNA Viruses" Suppl.* 7., Coico, ed., November, 2007), which is hereby incorporated by reference.

Insertion of the gene expression cassette. A strong subgenomic RNA promoter that drives expression of the major capsid protein in LR-2 relative, Beet yellows virus (BYV), was cloned and inserted downstream from analogous LR-2 promoter along with unique restriction sites Pac I and Fse I into one of the partial LR-2 cDNA clones. A reporter gene encoding green fluorescent protein targeted to endoplasmic reticulum (ER-GFP) was inserted between the two promoters (FIG. 1B). This design was expected to result in a high-level production of ER-GFP from authentic LR-2 promoter and LR-2 capsid protein from a recombinant BYV promoter described in (Agranovsky et al., *J. Gen. Virol.* 72:15-23, 1991) and illustrated in SEQ ID NO: 1.

Generation of a full-length cDNA clone of LR-2. Using overlapping partial cDNA clones, several prototype full-length LR-2 clones containing expression cassette were assembled in pBlueScript® (Stratagene, La Jolla, Calif.) under control of phage SP6 RNA polymerase promoter. Corresponding capped RNA transcripts were obtained in vitro and used to transfect tobacco suspension culture protoplasts and inoculate *N. benthamiana* plants. Because none of these experiments resulted in virus multiplication and infection, the cloned viral genome was re-sequenced. Multiple detrimental mutations throughout the genome were detected suggesting that errors were introduced during RT-PCR amplification of genome fragments. To overcome this major obstacle, the entire LR-2 genome was reassembled from the cDNA fragments obtained using reverse transcription and Klenow DNA polymerase instead of PCR. Although this approach resulted in a dramatic reduction in the number of lethal mutations, none of the resulting clones were entirely free of them. These results indicated that LR-2 cDNA in functional, mutation-free form was likely toxic to *E. coli* used for cloning.

One of the approaches that may alleviate the toxicity of recombinant DNA is to use a low-copy number plasmid for the cloning. To test this possibility, pCB-302 (Xiang et al., *Plant Mol. Biol.* 40: 711-717, 1999), a mini-binary vector suitable for cloning in both *E. coli* and *A. tumefaciens* was used. This vector has been modified to accommodate all control elements required for subsequent expression of LR-2 genome in plants using agroinoculation. These elements included 35S RNA polymerase promoter, NOS terminator, and a ribozyme custom designed for a release of an authentic 3'-terminus of LR-2 RNA upon its transcription. The latter processing event is critical for the ability of viral RNA to replicate in the plant. Following these modifications, the full-length LR-2 cDNA was cloned into pCB-302 and designated plasmid pCB-LR-GFP (SEQ ID NO: 1).

The LR-2 cDNA was cloned between the right and left T-DNA borders of plasmid pCB-302. A map of the resulting plasmid is shown in FIG. 1C. Nucleotide sequencing of the entire cloned viral genome revealed no detrimental mutations.

Figure 2:
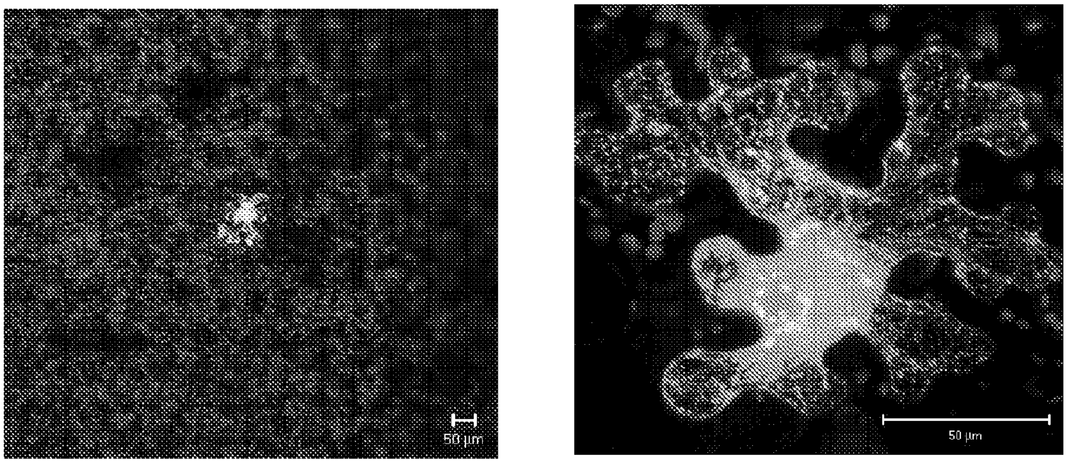
FIG. 2 shows *N. benthamiana* cells infected with GLRaV-2/ER-GFP upon agroinoculation at two different scales using confocal laser scanning microscopy. Bright fluorescence marks endoplasmic reticulum of the virus-infected cell due to expression of ER-GFP marker by virus. Background fluorescence is due to autofluorescence of chloroplasts. Bars, 50 μm.
Figure 3:
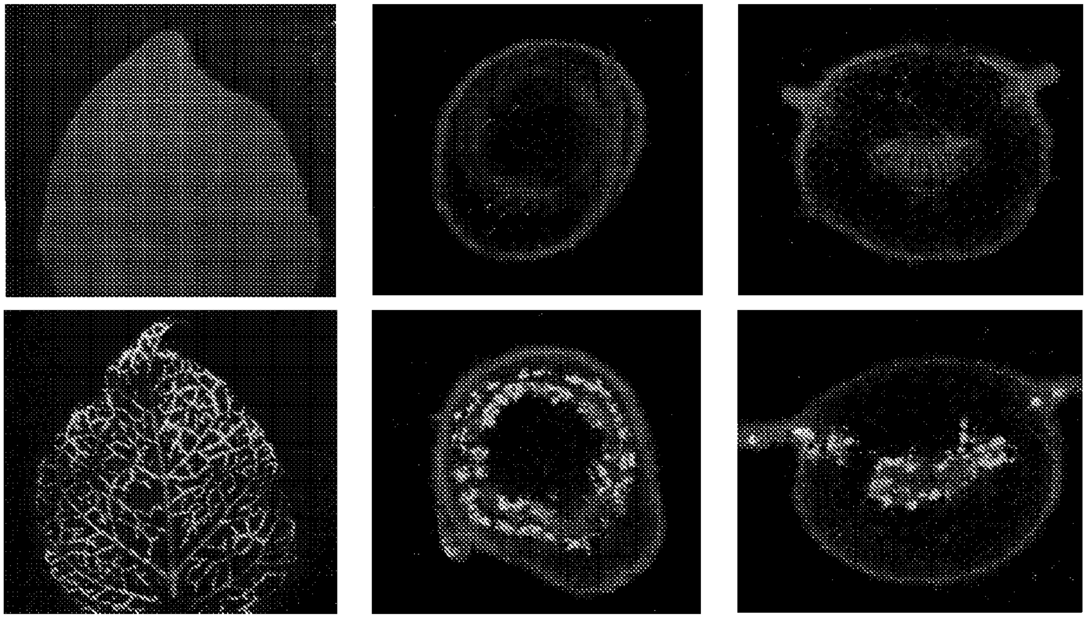
FIG. 3 shows images taken by epifluorescent microscopy of tissues from plants of *N. benthamiana* systemically infected with GLRaV-2/ER-GFP upon agroinoculation (bottom row) compared to control, uninfected plants (top row). Bright fluorescence highlights predominantly phloem cells infected by virus and expressing ER-GFP. Stems and petioles were manually cross sectioned prior to microscopic imaging. Background fluorescence is due to autofluorescence of chloroplasts.
Figure 4A:
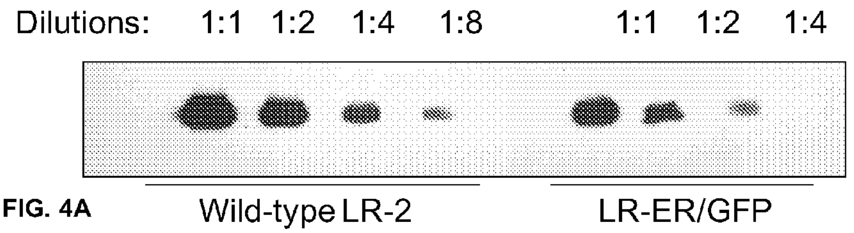
FIG. 4 (FIG. 4A) Immunoblot analysis of the extracts from plants infected with the wild type virus and virus modified to express ER-GFP using CP-specific antibodies as shown below the image. Dilutions of the original leaf extracts are shown at the top.
(FIG. 4B) RT-PCR analysis of the RNAs isolated from *N. benthamiana* plants infected with the wild type virus and virus modified to express ER-GFP. The products of RT-PCR were separated in 1% agarose gel and stained with ethidium bromide. M, DNA size markers; bands corresponding to 1- and 2-kb DNAs are marked by arrows.

Infectivity assays in *N. benthamiana*. pCB-LR-GFP was transformed into *agrobacterium* and the resulting strain was grown, induced, and used for agroinfiltration of the *N. benthamiana* plants. On average at 2-3 weeks post inoculation, some of the plants exhibited typical infection symptoms. Confocal laser scanning microscopy detected strong GFP expression in the epidermal cells of the infiltrated leaves. As expected, GFP fluorescence was confined to a characteristic network of endoplasmic reticulum (ER) and ER-derived viral replication complexes (FIG. 2). Examination of the upper leaves, stems, and petioles of the symptomatic plants revealed high levels of ER-GFP accumulation in the phloem tissues throughout the plant that is typical of LR-2 and other closteroviruses (FIG. 3). Ultra-structural analysis of the infected tissue confirmed accumulation of the vast amounts of filamentous LR-2 virions in the phloem cells, especially in the bundle sheath cells that surround xylem and sieve elements. Furthermore, immunoblot analysis confirmed efficient accumulation of LR-2 capsid protein (FIG. 4A). These experiments demonstrate that the cloned, recombinant LR-2 is highly infectious, is able to spread systemically, and express a recombinant protein in an experimental host *N. benthamiana.*

Figure 5:
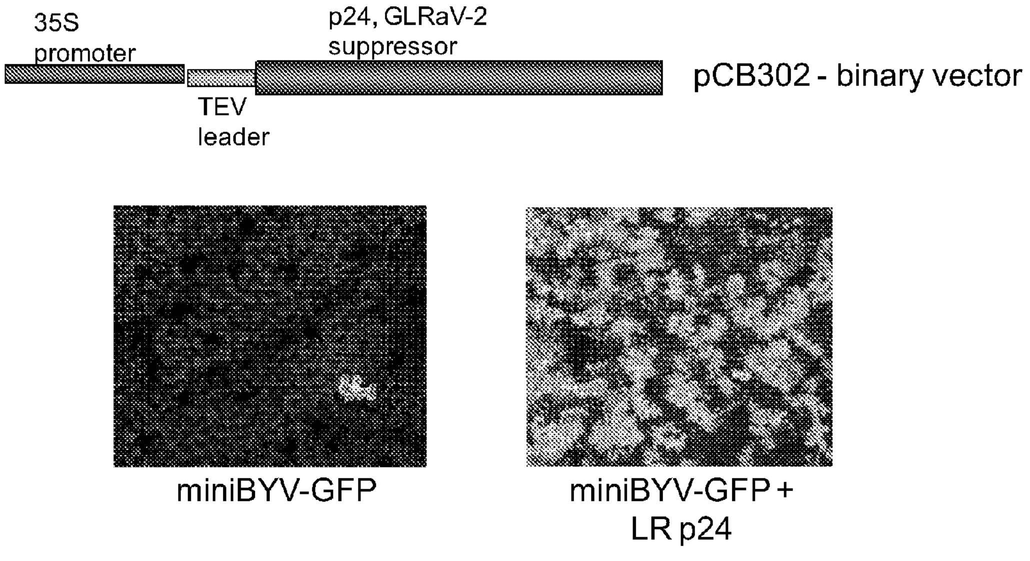
FIG. 5 Top, a diagram showing the design of a binary vector that expresses p24, a 24-kDa LR-2 suppressor of RNA silencing cloned to a binary vector pCB302. TEV leader, cDNA sequence corresponding to the 5'-untranslated region of the Tobacco etch virus and used to enhance translation of the p24. Bottom, confocal images of the rare cell infected by miniBYV-GFP alone (left panel) and miniBYV-GFP with p24 co-expression (right panel). Images are from Chiba et al. (*Virology* 346: 7-14, 2006).

Improvement of the agroinfection efficiency. Although LR-2 infection consistently occurred upon agroinoculation, the number of primarily-infected cells in the inoculated leaves was low and only fraction of the inoculated plants developed systemic infection. To enhance the ability of recombinant virus to establish infection, a method based on the expression of viral suppressors of RNAi at the time of inoculation was used (Chiba et al., *Virology* 346: 7-14, 2006). Furthermore, it was demonstrated that LR-2 encodes a very potent suppressor of RNAi, p24. Therefore, *agrobacterium* that was engineered to express p24 was added to inoculum. This technique resulted in a ~5,000-fold increase in the specific infectivity of the virus launched by *agrobacterium* (FIG. 5) (Chiba et al., *Virology* 346: 7-14, 2006). Now 100% infection of the agroinoculated *N. benthamiana* plants is routinely obtained.

Figure 4B:
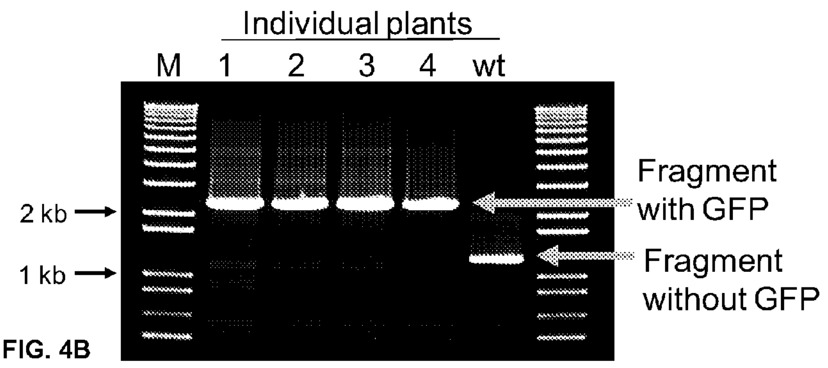

Genetic stability of the LR-2 gene expression vector. To test if the LR-2 vector is able to retain an intact foreign insert encoding reporter protein, RNAs have been isolated from the top leaves of the four individual infected *N. benthamiana* plants. RT-PCR has been done using these RNAs and primers located downstream and upstream from the ER-GFP expression cassette. The resulting PCR products were of expected size indicating retention of the entire cassette in each of the tested plants (FIG. 4B) Importantly, no shorter products that could originate from partial or complete loss of the cassette were detected. These data confirmed that the engineered vector is genetically stable and can be used for efficient expression of the recombinant proteins.

Development of gene silencing vector for functional genomics and virus control. To test a potential of LR-2 vector for virus-induced gene silencing (VIGS), GFP-transgenic *N. benthamiana* line 16c and GFP-expressing LR-2 was used. Strong GFP silencing was observed in the systemically infected leaves of 16c plants following inoculation with LR-2-GFP (FIG. 6). This experiment demonstrated that LR-2-GFP acts similarly to known VIGS vectors by inducing RNAi of the transgene in response to overexpression of the cognate gene by virus, providing proof of concept for the utility of LR-2 vector for VIGS.

Micropropagation of grapevine and transfer to soil. A reliable supply of experimental grapevine plants year round was developed for testing the new vectors using a technique for micropropagation of grapevine under sterile conditions in plastic boxes using agar-based growth medium. Such plants can be used for infectivity assays directly. Furthermore, there are anecdotal reports indicating that micropropagated plants have increased susceptibility to viral infection. Alternatively, micropropagated plants can be transferred to soil and grow in the greenhouse to obtain woody plants that are more similar in their susceptibility to plants grown in the open soil. Conditions were optimized for such transfer and obtained constant supply of the micropropagated and greenhouse grapevine plants.

Briefly, 12 inch cuttings with at least two buds were bundled into groups of 20-30 and soaked in a 10% bleach solution for 10 minutes, rinsed three times in water, then immersed in water for 12-24 hours. The bundles were then dipped in rooting solution (Dip'N Grow, Dip'N Grow Inc., Clackamas, Oreg.) and planted in moist vermiculite warmed to 85° F. Rooting occurred in 3-4 weeks. The cuttings were then planted 4-6 inches deep in potting soil under a misting bed set for three seconds every eight solar units (daytime) and 3 seconds every 2 hours (nighttime). Once leaves appeared in approximately two weeks, misting was decreased to prevent mold and mildew growth.

To establish grapevines in tissue culture, new shoots were removed and all but one leaf was removed from the shoot tip. The shoots were incubated in 0.05% Ivory liquid soap (Proctor and Gamble, Cincinnati, Ohio) for 10 minutes, rinsed in water for one hour, then sonicated for ten minutes in a sonicating water bath. The shoots were surface sterilized in a 5% bleach solution for six minutes and moved to a laminar flow hood for sterile handling. The shoots were rinsed in sterile deionized water, trimmed at the base and planted in OH agar medium. The shoots were incubated in a growth chamber for two weeks; GS 1 liquid was added, incubated for another two weeks, and then transferred to GS 1 agar medium. Every two weeks, fresh medium was added, then after a month, the shoots were switched to the next stage medium (GS2, GS3). Roots developed in GS3 medium.

Grape OH Medium

| Ingredient | Concentration g/L |
|---|---|
| M & S salts | 3.22 g |
| Thiamine | 0.8 ml stock ( ) |
| Inositol | 0.100 g 0.5 mg/ml |
| Sucrose | 7 g |
| $NaH_2PO_4$ | 0.170 g |
| Adenine sulfate | 0.08 g |
| Adjust pH to 5.7 | |
| Agar | 3 g |

Autoclave for 20 minutes, cool in water bath at 50° C. for 30 minutes then add antibiotic: Cefotaxime 0.2 g. Filter sterilize into cooled medium and mix. Dispense to sterile test tubes.

| Grape Stage 1 (GS1) Medium | |
|---|---|
| Ingredient | Concentration g/L |
| M & S salts | 3.22 g |
| Thiamine | 0.8 ml stock (0.5 mg/ml) |
| Inositol | 0.1 g |
| Sucrose | 20 g |
| BAP | 2 mls stock (0.5 mg/ml) |

Autoclave for 20 minutes, cool in water bath at 50° C. for 30 minutes then add antibiotic: Cefotaxime 0.2 g. Filter sterilize into cooled medium and mix. Dispense to 24 sterile Magenta boxes.

| Grape Stage 2 Medium | |
|---|---|
| Ingredient | Concentration g/L |
| M & S salts | 3.22 g |
| Thiamine | 0.8 ml stock (0.5 mg/ml) |
| Inositol | .025 g |
| Sucrose | 15 g |
| $NaH_2PO_4$ | 0.05 g |
| BAP | 4 mls stock (0.5 mg/ml) |
| IAA | 0.5 mls IAA stock (1 mg/ml) |
| Adjust pH to 5.3 | |
| Agar | 2 g |
| Gelrite ® gellan gum | 1.2 g |

Autoclave for 20 minutes, cool in water bath at 50° C. for 30 minutes then add antibiotic: Cefotaxime 0.2 g. Filter sterilize into cooled medium and mix. Dispense to 24 sterile Magenta boxes.

| Grape Stage 3 (GS3) Medium | |
|---|---|
| Ingredient | Concentration g/L |
| M & S salts | 3.22 g |
| Thiamine | 0.8 ml stock (0.5 mg/ml) |
| Inositol | .025 g |
| Sucrose | 12.5 g |
| $NaH_2PO_4$ | 0.05 |
| IAA | 1 ml stock (1 mg/ml) |
| Adjust pH to 5.3 | |
| Agar | 1 g |
| Gelrite ® gellan gum | 1 g |

Autoclave for 20 minutes, cool in water bath at 50° C. for 30 minutes then add antibiotic: Cefotaxime 0.2 g. Filter sterilize into cooled medium and mix. Dispense to 24 sterile Magenta boxes or 12 Double-Decker Magenta boxes.

Numerous grape varieties are being micropropagated and examined for their susceptibility to agroinfiltration and foreign protein expression. Cabernet franc and Sirah varieties have demonstrated desirable properties. Further, sterile plants transferred to antibiotic-free medium have been preliminarily found to be more susceptible to agroinfiltration.

*Agrobacterium* preparation. To prepare the *Agrobacterium*, the agro construct was streaked onto LB Kan (50 µg/ml) agar plate and incubated at 28° C. for three days. Single colonies were selected and added to a 5 ml culture on LB Kan (50 µg/ml), MES (10 mM) and acetosyringone (20 µM), and shaken at 220 rpm and 28° C. Rifampicin (50 µg/ml) was added if Agro strain C58 GV2260 was used. The starting cultures were transferred to 500 ml LB Kan (50 µg/ml), MES (10 mM) and acetosyringone (20 µM) and shaken overnight (1-20 hours) at 28° C. The culture was centrifuged at 6000 rpm for 10 minutes at room temp and the cell pellet suspended in 20 ml induction buffer for a final concentration of 2.0 $OD_{600}$ for full virus constructs or 0.7 $OD_{600}$ for GFP marker only constructs by combining with 0.1-0.14 $OD_{600}$ for suppressor p24 and adding additional induction buffer.

To prepare the suppressor p24 construct, the Agro stock was prepared as above, then suspended in 20 ml induction buffer at a final concentration 0.1 $OD_{600}$ to be combined with full virus construct suspension or 0.14 $OD_{600}$ to combined with GFP marker only suspension.

Induction Buffer 10 mM $MgCl_2$=2 ml of 0.5 $MgCl_2$ 10 mM MES pH 5.85=2 ml of 0.5 M MES pH 5.85 per 100 ml 150 µM acetosyringone=100 µl of 150 mM acetosyringone

*Agrobacterium* Infiltration of Micropropagated Grapevine Leaves or Entire Plants. Healthy leaves from micropropagated plants were wounded with 31 g needle by poking the large veins and leaf surface. Single leaves were placed in tubes with 5-10 ml of induction suspension, or the full plant was loosely in large beaker with 200 ml induction suspension. The grapevine/agro suspensions were sonicated for 10 minutes in a Branson 3510 sonicating water bath, the soaked in induction suspension for 2-3 hrs after sonication. The grapevine leaves or plants were blotted on sterile paper towels, then leaves were placed on water agar plates (7 g agar/1 L water) and whole plants potted in 4 inch pots containing potting mix and watered liberally. Plastic cups were placed tightly over the plants to reduce transpiration in the growth chamber. Ambient air was gradually introduced to potted plants by tilting the angle of the cups over a two week period until eventually removing plastic cups.

Leaves were monitored for GFP expression by microscope after day 4 for GFP marker only constructs and after day 12-14 for full viral/GFP constructs.

Similar techniques may be used with other portions of the plant, such as the rootstock.

Expression of GFP in grapevine using *agrobacterium*. In parallel with the efforts to generate infectious clone of LR-2, experiments aimed at developing technologies for *agrobacterium*-mediated transient expression of recombinant genes in grapevine were conducted. These experiments were designed to facilitate future infectivity tests in grapevine. Using *agrobacterium* engineered to express free GFP reporter (FIG. 7C) and a technique of vacuum infiltration of bacterial suspension into leaves or entire plants, accumulation of GFP in micropropagated plants was demonstrated. To this end, detached agroinfiltrated leaves were kept in Petri dishes over water agar in a plant growth chamber at 22° C. for 4 days and screened for GFP expression using epifluorescent stereoscope Leica MZ 16F equipped with GFP2 filter and digital camera (as shown in FIGS. 7A and B) or confocal laser microscope. Confocal laser scanning microscopy was done using Zeiss LSM 510 META (Zeiss, Germany) microscope fitted with the 488 nm excitation and 508 nm emission filters. The software package provided by manufacturer was used for image processing.

An alternative technique of agroinoculation using immersion of the plants into ultrasonic bath with bacterial suspension was also tested as described above. This approach proved to be as successful as infiltration with additional benefit of simplicity (FIG. 7A). Moreover, sonication resulted in a frequent expression of GFP in the vascular leaf tissue (FIG. 7B). Because LR-2 is preferentially associated with the phloem, this technique is expected to facilitate infection.

Additional testing utilizing *Agrobacterium* vitis and *A. rhizogenes* isolates is being conducted to determine if these bacteria may provide better efficiency of agroinoculation in grapes compared to traditional *A. tumefaciens*. Further, optimization of the protocols for agroinfiltration and sonication, testing of the utility of agroinfection combined with grafting (Omega-grafted cuttings treated with bacterial suspension) and a peel-heal agroinoculation technique whereby bacterial suspension is applied to the phloem exposed by peeling the bark is ongoing to improve transformation.

Figure 8:
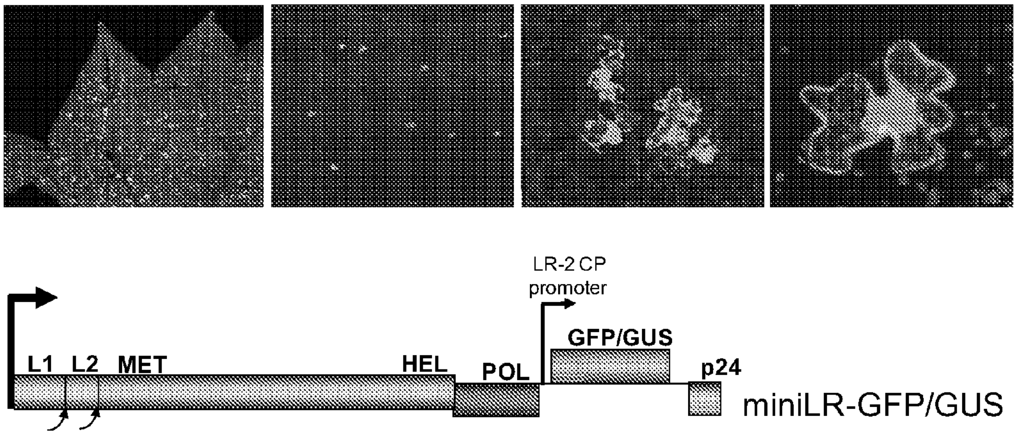
FIG. 8 Grapevine infection with miniLR-2-GFP launched by agroinfiltration showing images of the inoculated leaf and individual GFP-expressing fluorescent cells (top row) and a genetic map of the miniLR-GFP replicon. L1 and L2, leader proteinases; MET, methyltransferase domain; HEL, RNA helicase domain; POL, RNA-dependent RNA polymerase; GFP, green fluorescent protein; p24, a 24-kDa protein.

Infectivity assays in grapevine. Two different LR-2 clones were used for agroinoculation: i) miniLR-GFP/GUS (this mini-genome includes only the genes required for replication plus a reporter GFP/GUS gene and lacks genes required for virion assembly and transport in plants; SEQ ID NO: 2). The GFP/GUS reporter represents a fusion of GFP that can be detected by epifluorescent microscopy and GUS (β-glucuronidase) that possesses enzymatic activity providing sensitive in situ and in vitro assays. The map of miniLR-GFP/GUS is shown in FIG. 8; the corresponding nucleotide sequence is provided as SEQ ID NO: 2; and ii) full-length LR-2-GFP (SEQ ID NO: 1). When the micropropagated plants agroinoculated with miniLR2-GFP/GUS mixed with p24-expressing plasmid were screened, large numbers of infected cells that expressed ER-GFP reporter in the ER were observed (FIG. 8) demonstrating an ability of the mini-vector to replicate and express reporter protein in the grapevine leaf cells. Therefore, each GFP-positive cell detected by epifluorescent or confocal laser scanning microscopy represents a successful event of launching the viral vector and obtaining expression of the reporter by the viral vector in this case presented by the mini-replicon.

Figure 9:
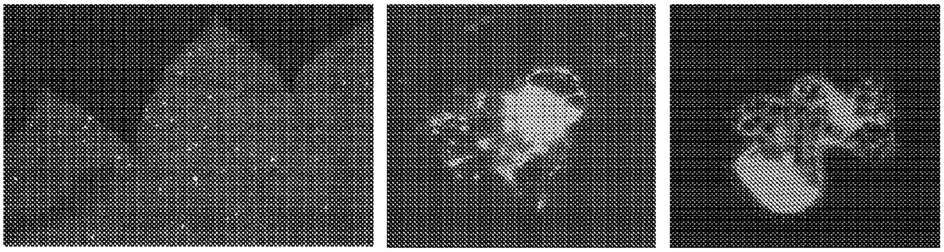
FIG. 9 Grapevine infection with the full-length LR-2-GFP GFP launched by agroinfiltration showing images of the inoculated leaf and individual GFP-expressing fluorescent cells.

However, similar experiments with the full-length vector resulted in infection of the limited number of cells (FIG. 9). In fact, in previous work with BYV, it was found the mini-genome had much higher infectivity upon agroinfection (Chiba et al., *Virology* 346: 7-14, 2006).

Further development of the full-length LR-2 vector. The original full-length LR-2 clone was generated using LR-2 genomic RNA isolated from the virus that was propagated in *N. benthamiana*. To improve grapevine infectivity and decrease possible mutation due to virus adaptation to an experimental host, the full-length clone was reassembled from cDNA fragments derived directly from LR-2 infected vine of Pinot Noir obtained from a local Oregonian vineyard.

Total RNA was purified from leaves using a Plant RNeasy kit (QIAGEN) and used as a template for random-primed cDNA construction. 2 to 4 kb contiguous fragments were then PCR amplified from this cDNA. Oligonucleotides for the PCRs were designed based on the published sequence of the GRLaV-2 and overlapped unique cloning sites present in the cDNA of this virus. The amplified PCR fragments were then cloned into a binary plasmid carrying the original variant of the LR-2 cDNA to replace existing parts with the ones derived from a virus present in grapevine. For each of the fragments at least 4 clones were sequenced to deduce consensus sequences that correspond to predominant and fully biologically active variant of LR2 genome present in grapevine. The complete genomic cDNA comprised of the consensus pieces was reassembled de novo. The new binary plasmid carrying the cDNA for the grapevine-derived virus derived from the Pinot Noir and never passed through *N. benthamiana* was designated LR2-*Vitis*.

The entire nucleotide sequence of this grapevine-derived LR2-*Vitis* expression cassette is shown in SEQ ID NO: 7). This sequence contains 74 nucleotide differences from an original, *N. benthamiana*-derived viral cassette (FIG. 14). It seems likely that these differences reflect adaptations of the virus to the systemic infection of either natural (grapevine) or experimental (*N. benthamiana*) host plant. Therefore, it is expected that the grapevine-derived LR2-*Vitis* vector will possess an increased ability of propagation in the grapevine.

Utilization of the phloem-specific promoters of *V. vinifera*. The LR-2 and LR2-*Vitis* vectors are launched using the CaMV 35S RNA polymerase II (POL II) promoter that drives the transcription of viral RNA upon agroinoculation. Although 35S promoter is routinely used for such purposes, it could be suboptimal for grapevine infection using LR-2 vectors. Indeed, LR-2 is naturally infects grapevine and is limited to the phloem tissue, whereas 35S promoter is not specific to either grapevine or phloem. Therefore, we used bioinformatics to identify the candidate grapevine phloem-specific promoters that can be used for replacement of the 35S promoter in order to improve grapevine infection by LR2-*Vitis*.

Three highly-expressed, phloem-specific *A. thaliana* genes were identified, and the corresponding protein sequences and BLASTP search were used to identify apparent *V. vinifera* orthologs. The *V. vinifera* genomic sequences upstream from corresponding protein-coding sequences (SEQ ID NOs: 8-10) are proposed to be useful as phloem-specific promoters in place of the exemplified 35S promoter in a LR2-*Vitis* cassette. The specific nature and properties of the *V. vinifera* promoters are outlined below.

1. The promoter of the *A. thaliana* SUCROSE TRANSPORTER 2 (SUC2 sucrose-$H^+$ symporter) gene (At1g22710) was first characterized by Truernit and Sauer (*Planta* 196: 564-570, 1995). In *Arabidopsis*, this promoter regulates expression of the phloem companion cell—specific AtSUC2 sucrose—$H^+$ symporter gene in the entire veinal network of fully developed leaves (Imlau et al., *Plant Cell* 11:309-322, 1999). Imlau et al. was also found that a 939 nt 3' fragment of this promoter is sufficient to drive phloem-specific, high-level expression of a reporter gene 2. *Arabidopsis* gene At5g57350 codes for a plasma membrane $H(^+)$-ATPase 3 (proton pump) and is expressed in phloem throughout the plant (DeWit et al., *Plant J.* 1, 121-128, 1991). The 2,467-kb promoter fragment of this ORF was sufficient to drive gene expression in phloem companion cells present in leaves, stems, and roots (HongYu et al., *Chinese Science Bulletin,* 52: 1949-1956, 2007).

3. *Arabidopsis* Sucrose synthase 1 gene (At5g20830). A 2 kb promoter region of this ORF fused to a reporter gene directs its expression in the phloem of mature leaves (Bieniawska et al., *The Plant Journal* 49, 810-828, 2007). The mRNA 5'-end begins with ATCTTA (Martin et al., *Plant J* 4: 367-377. 1993) which is very close to the 5'-terminal sequence of LR-2 making this promoter a very attractive candidate for improvement of infectivity of LR2-*Vitis* in grapevine.

The nucleotide sequences of the grapevine promoters located upstream from the grapevine ORFs encoding apparent orthologs of the *Arabidopsis* genes At1g22710, At5g57350, and At5g57350 are shown in SEQ ID NOs: 8-10 (respectively), along with database identifiers providing their respective positions in the *V. vitis* genome.

Characterization of the Effects of Leader Proteases on Replication.

Generation of GLRaV-2 Replicons Tagged by Insertion of the Fluorescent, Enzymatic, and Epitope Reporters Clones for GLRaV-2 were generated to determine functional profiles of L1 and L2. The entire, 16,486 nt-long GLRaV-2 genome was sequenced (GenBank accession number FJ436234; gene ID is: gi:213958313; incorporated herein by reference as of Jan. 26, 2009) and compared to the other isolates of this virus to reveal the closest relationship (99.6% nt identity) to the isolate 94/970 (Meng et al., *Virus Genes* 31, 31-41, 2005). The initial full-length clone was assembled using a binary vector and primarily conventional cDNA cloning to avoid introduction of the PCR-generated mutations, and sequenced to confirm its correspondence to the consensus nucleotide sequence of the viral genome. To facilitate launching of viral infection by agroinoculation, 35S RNA polymerase promoter of *Cauliflower mosaic* virus (CaMV) and a ribozyme sequence were inserted upstream and downstream of the GLRaV-2 sequence, respectively.

The resulting full-length GLRaV-2 clone was further modified to accommodate a reporter gene expression cassette immediately upstream of the CP open reading frame. This cassette contained GFP open reading frame followed by the BYV CP sub-genomic RNA promoter. As a result, the latter promoter directed expression of the GLRaV-2 CP, while the authentic GLRaV-2 CP promoter expressed the GFP reporter. This tagged full-length GLRaV-2 replicon was designated LR-GFP (FIG. 10A, middle diagram).

Deletion of the genes that are not required for the viral RNA amplification in the individual cells facilitates experimentation with the remaining genes that code for the leader protease, RNA replicase and RNAi suppressor. In the case of GLRaV-2, such minireplicon was generated by deletion of the gene block spanning genome region from p6 to p19 open reading frames and retention of the reporter gene. The reporter expression cassette was further modified to express a fusion of GFP with b-glucuronidase to result in the tagged GLRaV-2 minireplicon designated mLR-GFP/GUS (FIG. 10A, bottom diagram).

Figure 10A:
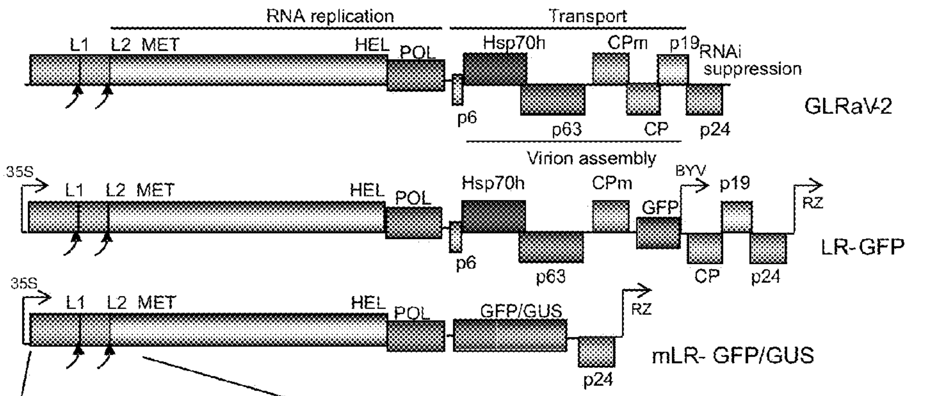
FIG. 10 (FIG. 10A) Schematic of the GLRaV-2 virus, the full-length vector (LR_GFP) and minivector (mLR-GFP/GUS).
(FIG. 10B) Domains of the leader proteases L1 and L2 with proteolytic processing, gene expression and infection results in *N. benthamiana* indicated.
Figure 10B:
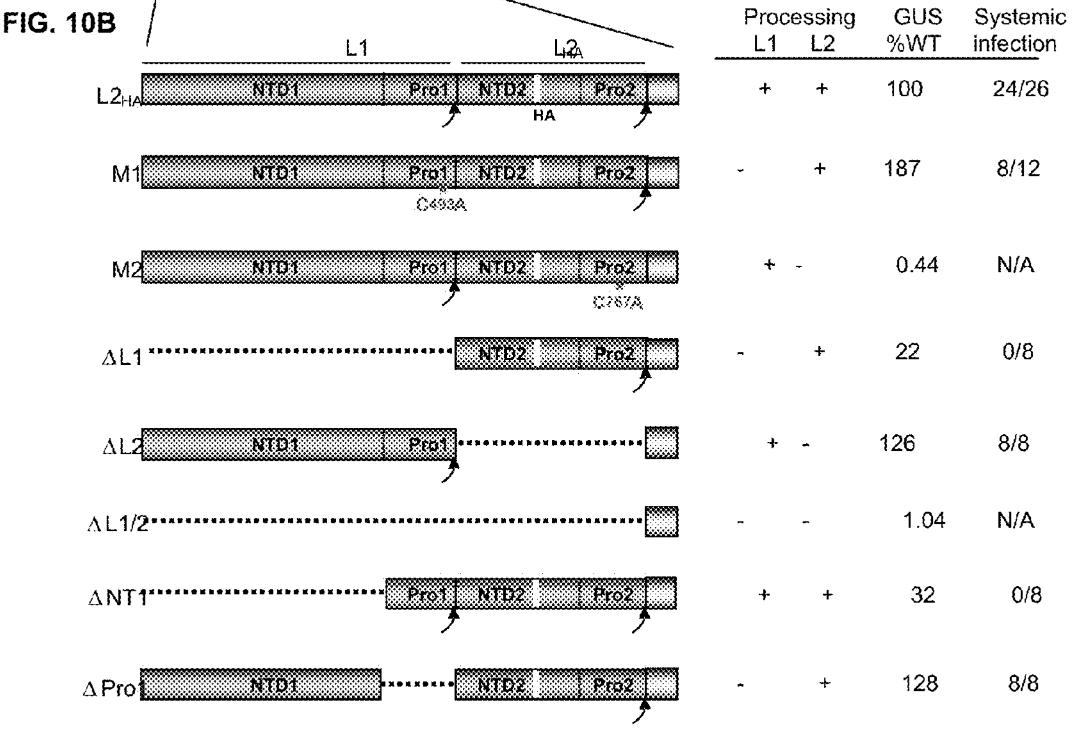
Figure 11A:
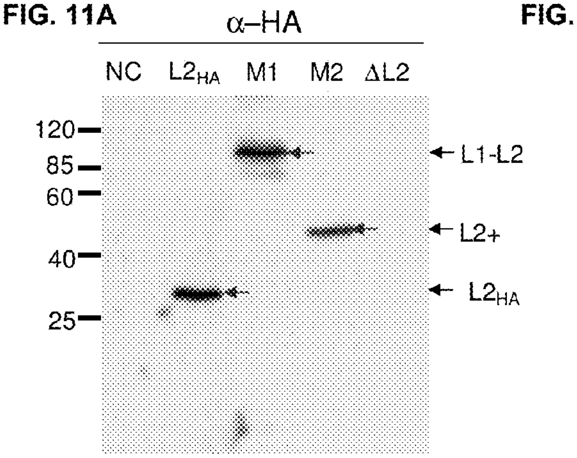
FIG. 11 Processing of vectors as shown by HA-tagging (FIG. 11A) and radiolabeling (FIG. 11B).

To permit immunochemical detection of $L2_{HA}$ using commercial HA-specific monoclonal antibody, both LR-GFP and mLR-GFP/GUS were modified by an insertion of the triple hemagglutinin epitope (HA) tag into the N-terminal domain of L2 (FIGS. 10B and 11A). Infectivity of the full-length and minireplicon variants was tested using leaf agroinfiltration of *N. benthamiana*, a systemic experimental host of GLRaV-2 (Goszczynski et al., *Vitis* 35, 133-133, 1996). For mLR-GFP/GUS, such agroinfiltration resulted in minireplicon RNA accumulation and efficient expression of the fluorescent and enzymatically-active GFP/GUS reporter in the initially inoculated cells (FIG. 10B). Importantly, the level of GUS activity in a HA-tagged variant was ~85% of that in the original mLR-GFP/GUS. Because this modest reduction was only marginally statistically significant (p value ~0.001), it was concluded that the insertion of HA tag into L2 did not significantly affect viral genome amplification. Attempts to insert an HA tag into L1 resulted in non-infectious replicons and were abandoned.

Both the original and HA-tagged variants of the full-length LR-GFP were systemically infectious in *N. benthamiana*; typical symptoms of the viral infection and GFP fluorescence were detected in the upper non-inoculated leaves by 3 weeks post agroinfiltration of the bottom leaves (FIG. 10A). Therefore, a series of the infectious tagged GLRaV-2 replicons were generated that can be launched to *N. benthamiana* and used to address L1 and L2 functions in the viral infection cycle.

Mutation Analysis of the L1 and L2 Functions in Protein Processing and RNA Accumulation in the Initially Inoculated Cells of *N. benthamiana*

Figure 11B:
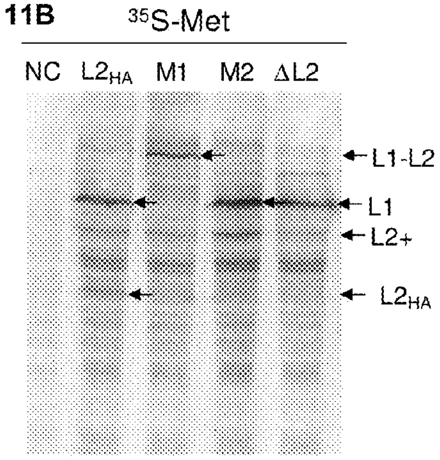

To address L1 and L2 functions, seven point mutations and deletions were introduced into corresponding coding region (FIG. 10B). In particular, to determine the requirements for the self-processing at the respective C-termini of L1 and L2, the predicted catalytic cysteine residues of the each protease ($Cys_{493}$ and $Cys_{767}$) were replaced by alanine residues to result in M1 and M2 variants, respectively (FIG. 10B). The processing competence of each variant was investigated using in vitro translation of the capped mRNAs encompassing the 5'-terminal untranslated region, the entire L1-L2 open reading frame and a short downstream region that encodes a part of the methyltransferase domain (FIG. 10B). The resulting translation products were analyzed using either immunoblotting and HA-specific antibody (FIG. 11A), or $^{35}$S-methionine labeling (FIG. 11B). As expected, a tagged non-mutant variant produced single HA-positive band corresponding to the fully-processed, HA-tagged L2 (FIG. 10B and FIG. 11A, lane $L2_{HA}$) and, in addition, isotope-labeled, fully processed L1 (FIG. 10B and FIG. 11B, lane $L2_{HA}$).

In contrast, translation of the M1 variant resulted in accumulation of a single major product corresponding to a L1-L2 fusion (FIG. 1B; FIGS. 2A and 2B, lanes M1). Analogously, mutational replacement of the predicted catalytic cysteine in L2 resulted in a lack of L2 self-processing, but did not affect the autocatalytic release of L1 (FIG. 10B; FIGS. 11A and 11B, lanes M2). Because mutation of the predicted active site residues did inactivate autoproteolysis by each leader protease, it was concluded that L1 and L2 are indeed the catalytically active, papain-like proteases.

To determine if the processing by L1 and L2 is required for viral RNA amplification, M1 and M2 variants of mLR-GFP/GUS were used to agroinfiltrate *N. benthamiana* leaves and to determine the resulting GUS activity. As shown previously for BYV minireplicon, GUS activity provides a reliable surrogate marker for measuring accumulation of the viral RNAs in the infected cells (Peng & Dolja, *J. Virol.* 74, 9766-9770, 2000). Using this marker, it was found that, unexpectedly, inactivation of the L1 cleavage resulted in more efficient GUS expression; almost 2-fold increase in GUS activity was detected in three independent experiments (FIG. 10B). In contrast, inactivation of L2 cleavage virtually abolished minireplicon infectivity: the corresponding GUS expression level was less than 0.5% of that of the parental mLR-GFP/GUS (FIG. 10B). This result is in agreement with the strict requirement for the cleavage by L-Pro for BYV minireplicon infectivity (Peremyslov et al., *J. Virol.* 72, 5870-5876, 1998); indeed fusion of either L-Pro or L2 with the replicase is likely to interfere with the synthesis of viral RNAs.

To determine the individual roles of L1 and L2 in RNA accumulation, the mutants were generated in which the coding regions of L1, L2, or both, were deleted. Interestingly, the L1 null mutant DL1 was capable of replication, although a corresponding level of GUS activity was ~5-fold lower than that in the parental mLR-GFP/GUS variant (FIG. 10B). Unexpectedly, deletion of L2 in the DL2 variant resulted in a slight increase in GUS expression suggesting that L2 is not essential for minireplicon accumulation in the isolated *N. benthamiana* cells (FIG. 10B). However, simultaneous deletion of L1 and L2 yielded the minireplicon DL1/2 that expressed only ~1% of the GUS activity observed in a parental mLR-GFP/GUS variant (FIG. 10B). Taken together, these results indicated that although the role of L1 in viral RNA amplification is more prominent than that of L2, the latter protease can rescue RNA accumulation of the L1-deficient mutant, and therefore L1 and L2 have partially overlapping functions in this process.

Both L1 and L2 possess the C-terminal papain-like protease domains (Pro1 and 2, respectively) and the N-terminal domains (NTD1 and NTD2, respectively; FIG. 10B). To determine the relative contributions of NTD1 and Pro1 in the L1 function, DNTD1 and DPro1 variants were generated in which these domains were deleted (FIG. 10B). The former of these minireplicon variants exhibited ~3-fold reduction in accumulation of GUS, while the latter produced even more GUS than the parental variant (FIG. 10B). These data indicated that the non-proteolytic rather than the protease domain of L1 provided a major contribution to viral RNA accumulation in *N. benthamiana* cells. It should be emphasized that the observed requirement for NTD1 for optimal RNA accumulation can reflect either a role of a protein domain, or of a corresponding coding region at the RNA level, or both.

Roles of L1 and L2 in the Virion Infectivity and Systemic Spread of GLRaV-2 in *N. benthamiana*

To define the potential functions of L1 and L2 in the viral cell-to-cell movement and long-distance transport, the DL1 and DL2 deletions were introduced into the background of the full-length LR-GFP variant. Following agroinfiltration, virions were isolated from the inoculated leaves and the virion suspensions of the equal concentrations were used to manually inoculate *N. benthamiana* leaves and to characterize the resulting infection foci using GFP fluorescence at 8 days post inoculation. For the parental LR-GFP variant, inoculation yielded 9.9±5.6 infection foci per leaf with the mean diameter of 4.3±1.4 cells. Very similar results (8.2±4.8 foci per leaf; mean diameter of 4.1±1.3 cells) were obtained for the LR-GFPDL2 variant indicating that L2 is dispensable for both the infectivity and cell-to-cell movement of the GLRaV-2 in *N. benthamiana*. Strikingly, deletion of L1 resulted in a dramatic, 25-fold reduction in the specific infectivity of the LR-GFPDL1 variant (0.4 cells per leaf). Furthermore, the very few detected GFP-positive foci were unicellular suggesting that either L1 or the corresponding coding region is essential for the virion ability to establish infection in the initially inoculated cells and to move to the neighboring cells.

Figure 12A:
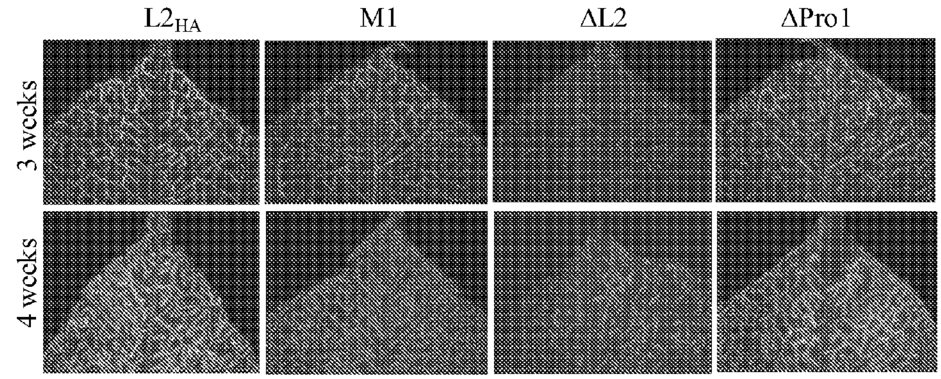
FIG. 12 (FIG. 12A) Long distance transport and systemic infection of *N. benthamiana* leaves with vectors.
(FIG. 12B) GFP accumulation in *N. benthamiana* leaves.
(FIG. 12C and FIG. 12D) Absence of gene expression in upper leaves of *N. benthamiana* after inoculation.

To determine if L1 and L2 are involved in the systemic transport of GLRaV-2, six replication-competent variants were tested in a context of the full-length LR-GFP launched to *N. benthamiana* plants using agroinfiltration. The inoculated plants were screened for the symptom, GFP, and CP expression at 3, 4, and 5 weeks post inoculation. Interestingly, most or all of the plants inoculated with M1 and DL2 variants became systemically infected indicating that neither L2 not the cleavage between L1 and L2 is required for the long-distance transport of the virus in *N. benthamiana* (FIG. 10B and FIG. 12A). Similar competence for the systemic spread was found in the case of DPro1 mutant. However, deletion of the L1 or its N-terminal domain resulted in complete loss of the replicon ability to establish systemic infection (FIGS. 10B and 12A).

Figure 12B:
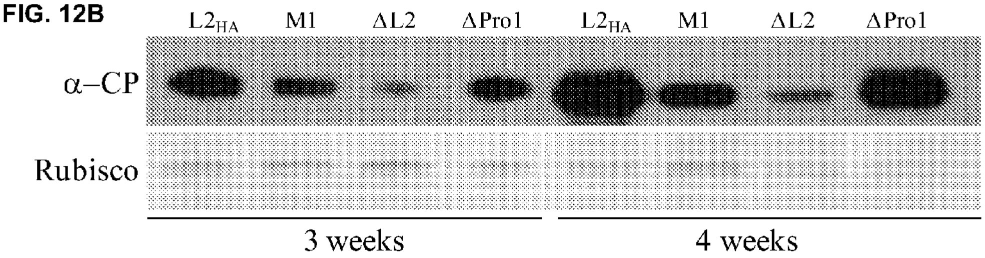
Figure 12C:
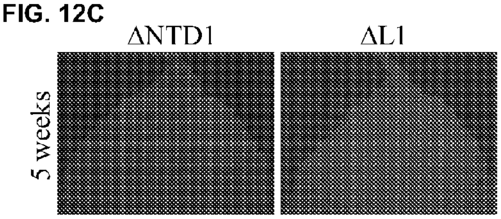
Figure 12D:
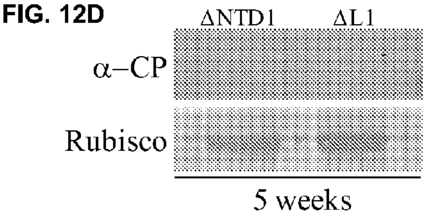

Observation of the systemically infected leaves revealed apparent differences in the GFP accumulation between the experimental variants (FIG. 10A). To further assess these differences, GLRaV-2 CP accumulation in the non-inoculated upper leaves was evaluated. Conspicuously, it was found that only the DPro1 mutant accumulated to the levels comparable to those of the parental variant (FIG. 12B). The remaining two mutant variants, M1, and especially DL2, each accumulated to the significantly lower levels than that of the parental LR-GFP variant both at 3 and 4 weeks post inoculation (FIG. 3B). Collectively, these results demonstrated that the L2 per se, and the cleavage between L1 and L2 are required for optimal systemic spread of GLRaV-2 in *N. benthamiana*. In addition, L1 and its N-terminal non-proteolytic domain or the corresponding coding regions are essential for the ability of GLRaV-2 to establish systemic infection since neither GFP nor viral CP were detectable in the upper leaves of the plants inoculated with the DNTD1 or DL1 variants even at five weeks post inoculation (FIGS. 12C and 12D).

Figure 13:
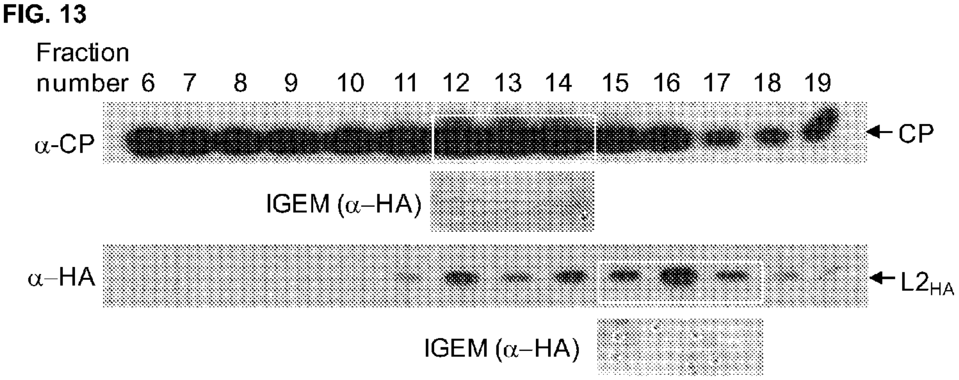
FIG. 13 Immunoblot analysis of gradient from sucrose fractionation of virions isolated from infected *N. benthamiana* leaves.

In BYV, both p20 and L-Pro are involved into viral systemic spread (Peng et al., *J. Virol.* 77, 2843-2849, 2003; Prokhnevsky et al., *J. Virol.* 76, 11003-11011, 2002). Of these, p20 is an integral component of the virion tail (Peremyslov et al., *Proc. Natl. Acad. Sci. U S A* 101, 5030-5035, 2004), while it is not known if L-Pro is present in the virions due to unavailability of the L-Pro-specific antibody. Because functional, HA-tagged variant of L2, were generated, it was used to determine if this protease is associated with the virions. The GLRaV-2 virions were isolated from systemically infected leaves and fractionated using sucrose density gradient. The peak of virions was detected in fractions 12-14 using CP-specific antibody (FIG. 13). However, the immunoblot analysis of the same gradient fractions using HA-specific antibodies showed the peak of L2 in fractions 15-17, suggesting that L2 present in the virion suspension is not physically associated with the virions (FIG. 13). This conclusion was further supported by the immunogold-specific electron microscopy used to detect HA epitopes present in L2. Indeed, only very weak gold labeling was found in the fractions 12-14 that contained bulk of the virions. Furthermore, a few gold microspheres detected in these fractions were not directly associated with the virions (FIG. 13, upper inset). The L2 peak fractions 15-17 contained much larger numbers of gold microspheres, but virtually no virions (FIG. 13, bottom inset) suggesting that L2 is not directly associated with GLRaV-2 virions.

L1 and L2 are Critical for Minireplicon Infection of the *V. vinifera*

It is generally accepted that *N. benthamiana* is, perhaps, the most promiscuous host for a great variety of plant viruses. To determine if the seemingly non-essential and largely redundant roles played by L1 and L2 in GLRaV-2 infection in this experimental host do faithfully reflect their roles in a grapevine infection, four minireplicon variants were agroinfiltrated to *V. vinifera* (Grenache) leaves (Table 1). At 8 days post inoculation with the parental mLR-GFP/GUS variant, ~300 unicellular, GFP-fluorescent infection foci per leaf were observed. Strikingly, infiltration using DL1 and DL2 variants resulted in a ~100-fold and ~7-fold reduction in the foci numbers, respectively, indicating that each of the leader proteases is required for the ability of minireplicon to establish infection in grapevine cells (Table 1). However, similar to what was observed in *N. benthamiana*, infectivity of the M1 variant was not significantly different from that of the parental variant.

Remarkably, measurements of GUS activity in the infiltrated leaves correlated well with the data on the numbers of the infected cells (Table 1) suggesting that the principal function of the leader proteases is to aid the establishment of viral infection rather than to increase accumulation of viral RNA in the infected cells. Because the effects of L1 and L2 deletion in *V. vinifera* were much more dramatic compared to those in *N. benthamiana*, it was concluded that each protease provides a significant and specific contribution into GLRaV-2 infection in its natural host plant.

TABLE 1

| Infectivity and GUS expression by mLR-GFP/GUS minireplicon variants in *V. vinifera* | | | |
|---|---|---|---|
| Experiment | Variant | Mean number of the infection foci (% of that in parental variant) | Mean GUS activity (% of the level in parental variant) |
| 1 | mLR-GFP/GUS | 100.00 | 100.00 |
| 1 | ΔL1 | 1.03 | 4.16 |
| 1 | ΔL2 | 14.96 | 10.03 |
| 1 | M1 | 104.44 | 103.11 |
| 2 | mLR-GFP/GUS | 100.00 | 100.00 |
| 2 | ΔL1 | 1.58 | 2.93 |
| 2 | ΔL2 | 10.44 | 10.87 |
| 2 | M1 | 133.43 | 118.08 |

Discussion

Without being bounded by any particular theory, the following discussion is provided. The instant disclosure allowed delineation of three major functions of L1 and L2 in the GLRaV-2 infection cycle: i) polyprotein processing; ii) virus accumulation in the initially infected cells; and iii) systemic transport of the infection.

In particular, it was found that both L1 and L2 are the active proteases with the conserved catalytic cysteines (FIGS. 10B and 11). The cleavage upstream from the methyltransferase domain of the viral RNA replicase polyprotein is essential for GLRaV-2 viability (FIG. 10B). Surprisingly, although L1 does cleave at its own C-terminus both in vitro (FIG. 11) and in vivo (FIG. 13), neither this cleavage nor the L1 protease domain per se are essential for systemic infection in *N. benthamiana* as evident from the phenotypes of M1 and DPro1 variants (FIGS. 10B and 12). However, slower virus accumulation in the non-inoculated leaves in these mutants (FIGS. 12A and 12B) suggests that the L1-mediated cleavage is required for the optimal development of systemic infection.

The deletion analysis indicated that L1 and L2 play partially overlapping roles in the viral RNA accumulation in the initially inoculated cells. When viral minireplicon was launched by agroinfiltration, complete deletion of L1 resulted in a ~5-fold reduction of RNA accumulation and expression. Similar effect was observed upon deletion of the non-proteolytic N-terminal domain of L1 indicating its principal role in L1 function (FIG. 10B). Although the deletion of L2 did not affect RNA accumulation, combined deletion of L1 and L2 resulted in a virtually nonviable minireplicon indicating that L2 provided a significant contribution into viral infectivity in the absence of L1.

Interestingly, when isolated virions containing full-length genome were used for plant inoculation, the infectivity and cell-to-cell movement of the DL2 variant were indistinguishable from those of the parental variant, while the virions of DL1 variant have lost their infectivity. The deletion of L1 but not L2 coding region could affect virion structure, stability, and infectivity. Therefore, it is possible that in addition to L1 function in RNA accumulation revealed by minireplicon agroinoculation, the corresponding coding region also functions at the RNA level to facilitate formation of the tailed virions capable of the local and systemic transport.

In accord with the latter assumption, DL1 and DNTD1 mutants were unable to establish a systemic infection upon agroinfiltration using full-length replicons (FIG. 12C). In contrast, deletion of the protease domain in DPro1 variant did not affect systemic infectivity indicating that virion tail formation was likely unaffected. The deletion of L2 resulted in a systemically infectious DL2 variant, which, however, exhibited much slower accumulation in the upper leaves (FIGS. 11A and 11B). This result indicated that L2 is required for the efficient systemic spread of GLRaV-2 in *N. benthamiana.*

Perhaps the most significant results of this study were obtained when the minireplicon variants were agroinoculated to the leaves of the GLRaV-2's natural host, grapevine. In a sharp contrast to a permissive experimental host *N. benthamiana* where L2 was superfluous for minireplicon infectivity, DL2 variant exhibited a ~10-fold reduction in RNA accumulation upon agroinfiltration into *V. vinifera* leaves (Table 1). The specific infectivity of the DL2 variant measured as a mean number of the GFP-fluorescent infected cells per leaf was also reduced ~10-fold. This correlation in the accumulation of the minireplicon RNA and the numbers of infected cells clearly points to the critical role of L2 in the virus invasiveness, i.e. the ability to establish infection in the inoculated cells. A role in GLRaV-2 invasiveness in grapevine is even more dramatic in the case of L1. Indeed, L1 deletion resulted in ~100-fold reduction in the RNA accumulation and specific infectivity of DL1 variant (Table 1). It was concluded that both L1 and L2 are essential for the optimal GLRaV-2 infection of the grapevine.

What is a specific functional significance of duplication and diversification of the leader proteases in GLRaV-2? It seems that the answer, at least in part, lies in the host-specific effects of L1 and L2 whose functional cooperation is required for the infection of grapevine but not *N. benthamiana*. In other words, a tandem of viral proteases could have evolved to boost the function of a single protease in order to subvert a perennial woody host potentially recalcitrant to virus infection. This hypothesis is compatible with the fact that in addition to GLRaV-2, protease duplication is found in CTV (Karasev et al., *Virology* 208, 511-520, 1995), Raspberry mottle virus (Tzanetakis et al., *Virus Res.* 127, 26-33, 2007), and Strawberry chlorotic fleck virus (Tzanetakis & Martin, *Virus Res.* 124, 88-94, 2007), each of which infects woody and/or perennial hosts, but not in BYV, Mint virus 1 (Tzanetakis et al., *Virus Res.* 127, 26-33, 2007), or Carnation yellow fleck virus that infect herbaceous annual hosts.

What is the possible mechanism by which L1 and L2 facilitate GLRaV-2 infection? The fact that each of these leader proteases acts in a host-specific manner to boost viral infectivity suggests that L1 and L2 could be involved in suppression of antiviral defense response. One possibility is that L1 and L2 are involved in suppression of RNA interference (RNAi) either independently from or in cooperation with the RNAi suppressor p24 (FIG. 1A) (Chiba et al., *Virology* 346: 7-14, 2006). However, efforts to identify effects of GLRaV-2 L1 and L2 or BYV L-Pro on the RNAi response in several model systems invariably failed. Moreover, it was found that the ectopic co-expression of L-Pro with the reporter reduced accumulation of the latter, suggesting possible involvement of the leader proteases in gene regulation at the RNA or protein level.

By analogy to papain-like proteases of coronaviruses (Lindner, *Virology* 362, 245-256, 2007), it can be hypothesized that closteroviral proteases act as deubiquitination enzymes (DUBs) whereby affecting regulation of the plant defense. The only fact that it is in a disagreement with DUB hypothesis is that inactivation of the L1 proteolytic activity in M1 variant has little effect on the viral infection. This apparent discrepancy can be explained if the L1-mediated binding rather than cleavage of the host defense-related proteins is sufficient to exert L1 function.

The generation of the full-size and minireplicons of GLRaV-2 tagged via insertion of the reporter genes or epitopes highlights a potential of this virus as a gene expression vector for the grapevine. In general, closterovirus-derived vectors provide strong advantages of relatively large genetic capacity and stability (Dolja et al., *Virus Res.* 117: 38-51, 2006; Folimonov et al., *Virology* 368(1):205-216, 2007). Utility of closteroviral vectors is further enhanced by a dramatic increase in the vector infectivity by co-expression of the homologous RNAi suppressors of which p24 of GLRaV-2 appears to be the strongest (Chiba et al., *Virology* 346: 7-14, 2006). Full realization of the GLRaV-2 vector potential requires development of the efficient inoculation technique for the grapevine.

Materials and Methods

Generation of the GFP-Tagged, Full-Length cDNA Clone of GLRaV-2

The GLRaV-2 isolate obtained from a local Oregonian vineyard was propagated on *N. benthamiana* plants as described earlier (Goszczynski et al., *Vitis* 35, 133-133, 1996). Virions were isolated (Napuli et al., *Virology* 274(1), 232-239, 2000) and the viral RNA was obtained using TRIzol reagent (Invitrogen) according to the manufacturer's protocol. A strategy for nucleotide sequencing of the viral genome and the generation of the intermediate and full-length viral cDNA clones was as described for BYV (Peremyslov & Dolja, *Curr. Protocols Microbiol.* (Suppl. 7), 16F.1.1-16F.1.26, 2007). The resulting sequence of GLRaV-2 RNA was deposited to GenBank (Accession No. FJ436234; incorporated herein by reference as of Jan. 26, 2009). The sequences of the numerous primers used in cloning procedures are available upon request.

In brief, a full-length cDNA clone of GLRaV-2 was assembled using pCB301 mini-binary vector (Xiang et al., *Plant Mol. Biol.* 40: 711-717. 1999), while the cDNA cloning was done using reverse transcription and either conventional synthesis of a double-stranded (ds) cDNA or PCR amplification. The NOS terminator was added to the pCB301 by using unique sites Sac I and Kpn I and a polylinker containing restriction sites Sac I, Barn HI, AatI I, Bbvc I, Rsr II, Bst EII, and SmaI was inserted between Sad site and NOS terminator to produce pCB301-NOS-PL. To add a CaMV 35S RNA polymerase promoter fused to the 5'-fragment of the viral cDNA (nts 1-2,034), a PCR-mediated DNA splicing technique was used. Separate PCRs were done to amplify the 35S promoter and the 5'end of GLRaV2 cDNA and to generate products with overlapping ends. These products were combined and used as templates for another round of PCR using primers complementary to the 5'- and 3'-ends of the full-length product. The latter product was cloned into pCB301-NOS-PL using Sac I (added to the 5'-end of 35S promoter) and BamH I (nt 2034) to produce p35S5'LR.

To add a ribozyme to the 3'-end of the viral cDNA, a megaprimer with a virus-specific part complementary to the 3'-end of the viral cDNA followed by a ribozyme sequence designed as described (Prokhnevsky et al., *J. Virol.* 76, 11003-11011, 2002) and a Sma I site was used in combination with a regular primer to amplify the 3'-terminal region of the GLRaV-2 cDNA (nts 14,842-16,486). Resulting PCR product was cloned into p35S5'LR using restriction sites BstE II (nt 14,842) and Sma I (added at the 3'-terminus of the megaprimer) to produce a p35S5'3'LR-Rib.

For cloning the internal region of viral cDNA (nts 2,029-10,827), three partially overlapping fragments of ds cDNA were obtained using conventional cDNA cloning and Gibco-BRL protocol for SuperScript II reverse transcriptase. These fragments were inserted into p35S5'3'LR-Rib using restriction sites Bam HI (nt 2,029), Aat II (nt 3,394), Bbv CI (nt 6,281), and Rsr II (nt 10,821) to generate p35S-5'BR3'LR-Rib. The remaining part of the viral cDNA (nts 10,821-14,848) was PCR-amplified and cloned into an intermediate vector pGEM-3Zf(+) (Promega). A nucleotide sequence encoding an endoplasmic reticulum-targeted GFP (Haseloff et al., *Proc Natl Acad Sci USA* 94(6), 2122-2127, 1997) followed by a BYV CP promoter was inserted upstream from the 5'-end of GLRaV-2 CP ORF. The resulting cDNA fragment was cloned into p35S5'-BR-3'LR-Rib using Rsr II (nt 10,821) and Bst EII (nt 14,842) sites to generate the full-length GLRaV-2 cDNA clone p35S-LR-GFP or LR-GFP for the brevity.

Generation of the Modified and Mutant GLRaV-2 Variants

The minireplicon variant mLR-GFP/GUS was engineered by modifying the LR-GFP cDNA via deletion of the cDNA fragments from the start codon of the p6 ORF (FIG. 1A) to nt 14,185 and from the Fse I site at the 3'-end of the GFP ORF to nt 15,285 (nt numbers correspond to the original GLRaV-2 cDNA). As a result, GLRaV-2 ORFs encoding p6, Hsp70h, p63, CPm, CP and p19 were deleted (FIG. 1A). The GFP ORF was then replaced with a hybrid GFP/GUS ORF described earlier (Peng et al., *Virology* 294, 75-84, 2002) using Pac I at the 5'-terminus of the GFP ORF and Fse I at the 3'-terminus of the GUS ORF.

Two plasmids, pGEM-35SLR-Pro and pGEM-SP6LR-Pro, containing the whole L1 and L2 coding region and a fragment of the methyltranferase coding region (nts 1-3,071) were generated by cloning the corresponding PCR-amplified fragments (FIG. 1B) into pGEM-3Zf(+). Both pGEM-35SLR-Pro and pGEM-SP6LR-Pro were used to generate pGEM-35SLR-$L2_{HA}$ and pGEM-SP635SLR-$L2_{HA}$ by inserting three copies of the hemagglutinin epitope (HA) tag (YPYDVPDYA; SEQ ID NO: 11) coding sequence downstream from codon 663 within L2 coding region. Each of these plasmids was used to introduce the following mutations into the L1 or L2.

Mutation 1 (M1) was generated by replacing the catalytic $Cys_{493}$ residue of L1 with Ala using site-directed mutagenesis. Analogously, mutation 2 (M2) was obtained via substitution of Ala for $Cys_{767}$ of L2. In DL2 mutation, the entire L2-coding region was deleted and $Lys_{848}$ residue downstream from L2 scissile bond was replaced with Gly to regenerate an authentic L1 cleavage site. Mutation DL1 was made by deleting the entire L1 coding region except for the 5'-terminal start codon. In mutation DNTD1, the entire N-terminal, non-proteolytic region of L1 was deleted, again except for the start codon. In mutation DPro1, the C-terminal proteinase domain of L1 was deleted while the N-terminal region of L1 was fused to the N-terminal region of L2. In the last mutation DL1/2, both L1 and L2 were deleted except for the start codon that was fused with the first Lys codon of the GLRaV-2 replicase, resulting in the formation of a replicase that differed from the proteolytically processed, wild-type replicase only by the presence of the N-terminal Met. The diagrams of all mutations are shown in FIG. 1B.

The pGEM-SP6LR-$L2_{HA}$ variants were used to analyze the proteolytic activity of the mutated proteases in vitro. The DNA fragments from the mutant derivatives of pGEM-35SLR-$L2_{HA}$ were cloned into mLR-GFP/GUS using Sbf I (located in the vector part of the plasmid) and Stu I (nt 3,063) sites. The DNA fragments from mutant derivatives of p35S-miniV94-GFPGUS were also cloned into the full-length cDNA clone LR-GFP using Sfi I (located in the vector part of the plasmid) and Bbv CI (nt 6,282).

Mutation Analysis of the Proteolytic Activity of L1 and L2

The pGEM-SP6LR-$L2_{HA}$ variants were linearized using Sma I and the corresponding in vitro RNA transcripts were generated using mMessage Machine kit (Ambion). To assay the proteolytic activity of the leader proteases, the resulting capped RNA transcripts were translated using the wheat germ extracts (Promega) and [$^{35}$S]-Met (Amersham/Pharmacia Biotech) or a non-labeled amino acid mixture. After 1 hr of incubation at 25° C., the products were separated by PAGE, electroblotted onto a PROTRAN nitrocellulose membrane and used for autoradiography or for immunoblotting using anti-HA rat monoclonal antibody (Roche) as first antibody and goat anti rat-peroxidase as secondary antibody.

Mutation Analysis of the L1 and L2 Roles in RNA Accumulation

*Agrobacterium tumefaciens* strain C58 GV2260 was transformed by each of the mLR-GFP/GUS variants by electroporation. Corresponding cultures were grown overnight at 28° C. with shaking, spun down and resuspended in a buffer containing 10 mM MES-KOH (pH 5.85), 10 mM $MgCl_2$, and 150 mM acetosyringone. Bacterial suspensions of each variant were mixed with corresponding cultures transformed to express an RNAi suppressor P1/HC-Pro from Turnip mosaic virus to enhance minireplicon infectivity (Chiba et al., *Virology* 346: 7-14, 2006). The final bacterial concentrations were 1.0 $OD_{600}$ for minireplicon-expressing variants and 0.1 $OD_{600}$ for the P1/HC-Pro-expressing variant. The induced bacterial cultures were infiltrated into lower surface of the *N. benthamiana* leaves using a syringe without a needle or vacuum infiltrated into the grapevine leaves. The GFP-fluorescent leaf cells were visualized using epifluorescent stereomicroscope Leica MZ 16F (Deerfield, Ill.) at 8 days post infiltration. Samples for GUS assays were prepared and GUS activity was measured using Hoefer TKO100 DNA fluorimeter (Hoefer Scientific Instruments) as previously described (Dolja et al., *Proc. Natl. Acad. Sci. USA* 89: 10208-10212, 1992).

Analysis of the Local and Systemic Virus Transport

To assay the cell-to-cell movement of the GFP-tagged virus variants, virions were isolated from the agroinfiltrated leaves of *N. benthamiana* at 2 weeks post inoculation (Napuli et al., *Virology* 274(1), 232-239, 2000), resuspended in a buffer containing 20 mM sodium phosphate (pH 7.4) and 1 mM $Na_2$-EDTA and inoculated manually to leaves of *N. benthamiana*. The fluorescent infection foci were analyzed using the epifluorescent stereomicroscope at 8 days post inoculation.

To investigate the systemic spread in *N. benthamiana*, plasmids carrying the corresponding variants in a context of the LR-GFP were mobilized into *A. tumefaciens*, the resulting bacterial suspensions were mixed with those engineered to express P1/HC-Pro as described above, and infiltrated into leaves of young *N. benthamiana* (6-8 leaf stage) plants. After 3, 4, or 5 weeks, the upper leaves of these plants were screened for the symptom development, whereas epifluorescence microscopy and a spot camera MicroPublisher3.3 RTV (QImaging) were used to document accumulation of the virus-expressed GFP Immunoblotting and custom-made GLRaV-2-specific antiserum in 1:5,000 dilution were used to document accumulation of CP.

Virion Analyses

To determine if HA-tagged L2 was associated with the virions, the sucrose gradient fractionation followed by immunoblotting was used. Virions isolated as described above were resuspended in a buffer containing 20 mM Na-phosphate (pH 7.4) and 1 mM $Na_2$-EDTA, loaded to the top of 10-40% sucrose gradients prepared in the same buffer, and centrifuged at 25,000 RPM for 4 hours in a Beckman SW40 rotor at 4° C. Gradients were separated into 25 fractions and the immunoblot analysis was done using anti-HA rat monoclonal antibody (Roche) and GLRaV-2-specific antibody to detect $L2_{HA}$ and CP, respectively. The immunogold-specific electron microscopy to detect $L2_{HA}$ was done essentially as described (Medina et al., *Virology* 260(1), 173-181, 1999).

It will be apparent that the precise details of the methods and compositions described may be varied or modified without departing from the spirit of the described invention. We claim all such modifications and variations that fall within the scope and spirit of the claims below.

What is claimed is:

1. A replication-competent plant gene transfer vector comprising a nucleic acid encoding:

a) viral genes from Grapevine leafroll-associated virus-2 (LR-2) comprising a methyltransferase, RNA helicase, and RNA-dependent RNA polymerase;

b) an RNAi suppressor selected from the group consisting of LR-2 p24 and Beet yellows virus p21;

c) LR-2 leader proteases L1 and L2; and d) a heterologous polynucleotide operably linked to a promoter, wherein the heterologous polynucleotide is expressed in a plant cell, and wherein the vector is capable of infectious replication in the plant cell, wherein the L1 protease has the amino acid sequence shown in SEQ ID NO: 4, and wherein the vector is adapted for virus-induced gene silencing.

2. The vector of claim 1, further comprising viral genes from Grapevine leafroll-associated virus-2 (LR-2) that are involved in virion assembly, transport within plants, or both.

3. The vector of claim 2, wherein the viral genes are selected from the group consisting of p6, Hsp70h, p63, CPm, CP and p19 from Grapevine leafroll-associated virus-2 (LR-2).

4. The vector of claim 1, wherein the heterologous polynucleotide encodes at least one polypeptide selected from the group consisting of a reporter molecule, a selectable marker, and a therapeutic gene.

5. The vector of claim 4, wherein the therapeutic gene is antifungal, antibacterial, antiviral or a taste modifier.

6. The vector of claim 4, wherein the therapeutic gene is for the treatment of Pierce's Disease or powdery mildew.

7. The vector of claim 6, wherein the therapeutic gene is a polynucleotide which triggers viral induced gene silencing, a Run1 polynucleotide, or encodes a lysozyme polypeptide.

8. The vector of claim 1, wherein the L2 protease has the amino acid sequence shown in SEQ ID NO: 6.

9. A plant cell comprising the vector of claim 1.

10. A plant comprising the vector of claim 1.

11. A method for virus-induced gene silencing in a plant cell, comprising introducing into the plant cell the vector of claim 1.

12. The method of claim 11, wherein introducing the vector into the plant cell comprises agroinoculation.

13. The method of claim 11, wherein the vector is a replication-competent vector, wherein the vector is introduced into a plant cell and subsequently replicates and infects at least one additional plant cell.

14. The method of claim 13, wherein the vector is a replication-competent vector, wherein the vector systemically infects a plant structure selected from the group consisting of tissue, leaf, stem, root, fruit, seed or entire plant.

15. The method of claim 11, wherein introducing the vector into the plant cell comprises grafting a plant part comprising the vector to a plant part that does not comprise the vector.

16. The method of claim 12, further comprising grafting a plant part comprising the plant cell comprising the vector to a plant part that does not comprise the vector.

17. The vector of claim 1, wherein the RNAi suppressor is p24.

* * * * *

UNITED STATES PATENT AND TRADEMARK OFFICE

CERTIFICATE OF CORRECTION

PATENT NO. : 8,415,147 B2
APPLICATION NO. : 12/865708
DATED : April 9, 2013
INVENTOR(S) : Dolja et al.

It is certified that error appears in the above-identified patent and that said Letters Patent is hereby corrected as shown below:

In the Specification:

Column 1, line 47, "1007" should read --2007--.

Column 1, line 65, "1007" should read --2007--.

Column 20, line 56, "and At5g57350" should read --and At5g20830--.

Column 21, line 29, "b-glucuronidase" should read --β-glucuronidase--.

Column 27, line 37, "Barn HI," should read --Bam HI--.

Signed and Sealed this
Sixth Day of May, 2014

Michelle K. Lee

*Deputy Director of the United States Patent and Trademark Office*